US006008046A

United States Patent [19]
Ffrench-Constant et al.

[11] Patent Number: 6,008,046
[45] Date of Patent: Dec. 28, 1999

[54] DRUG AND PESTICIDE SCREENING

[75] Inventors: Richard H. Ffrench-Constant; Meyer B. Jackson, both of Madison, Wis.

[73] Assignee: Ophidian Pharmaceuticals, Inc., Madison, Wis.

[21] Appl. No.: 08/072,064

[22] Filed: Jun. 2, 1993

Related U.S. Application Data

[63] Continuation-in-part of application No. 07/770,881, Oct. 4, 1991, abandoned.
[51] Int. Cl.$^6$ .............................. C12N 15/12; C12N 1/19; C12N 5/10
[52] U.S. Cl. ...................... 435/361; 435/325; 435/320.1; 435/348; 435/352; 435/252.3; 536/23.1; 536/23.5
[58] Field of Search ................................ 435/172.3, 69.1, 435/69.3, 6, 240.2, 254.11, 252.3, 810, 325, 348, 352, 361, 320.1; 935/9, 19, 23; 536/23.1, 23.5, 25.3

[56] References Cited

U.S. PATENT DOCUMENTS

| 4,683,195 | 7/1987 | Mullis et al. | 435/6 |
|---|---|---|---|
| 4,683,202 | 7/1987 | Mullis | 435/91 |

FOREIGN PATENT DOCUMENTS

PCT/US92/
  07613   4/1993  WIPO .

OTHER PUBLICATIONS ffrench–Constant et al., "A Single Amino Acid Substitution in a γ–Aminobutyric Acid Subtype A Receptor Locus is Associated with Cyclodiene Insecticide Resistance in Drosophila Populations," Proc. Natl. Acad. Sci. USA 90:1957 (1993).
Metcalf and Flint, *Destructive and Useful Insects, Their Habits & Control*, 4th ed., (McGraw–Hill, New York, 1962)(p. 397).
ffrench–Constant et al., "Drosophila as a Tool for Investigating the Molecular Genetics of Insecticide Resistance," in *Molecular Approaches to Fundamental and Applied Entomology*, (Springer–Verlag, New York, 1992)(pp. 1–37).
Kuffler and Edwards, "Mechanism of Gamma Aminobutyric Acids (GABA) Action and Its Relation to Synaptic Inhibition," J. Neurophysiol., 21:589 (1965).
Otsuka et al., "Release of Gamma–Aminobutyric Acid From Inhibitory Nerves of Lobster," Proc. Natl. Acad. Sci. USA 56:1110 (1966).
Usherwood and Grundfest, "Peripheral Inhibition in Skeletal Muscle of Insects," *J. Neurophysiol.*, 28:497 (1965).
Olsen and Tobin, "Molecular Biology of GABA$_A$ Receptors," FASEB J., 4:1469 (1990).
Harvey et al., Sequence of a Functional Invertebrate GABA$_A$ Receptor Subunit Which Can Form a Chimeric Receptor With a Vertebrate α Subunit, EMBO J., 10:3239 (1991).

ffrench–Constant, "A Point Mutation in a Drosophila GABA Receptor Confers Insecticide Resistance," Nature, 363:449 (1993).
Budavari et al., (eds.), *Merck Index,* Merck & Co., Rahway, New Jersey, 1989)(p. 1177).
Wallace et al., "Hybridization of Synthetic Oligodeoxyribonucleotides to φX174 DNA: The Effect of Single Base Pair Mismatch," Nucleic Acids Res., 6:3543 (1979).
Wallace et al., "The Use of Synthetic Oligonucleotides as Hybridization Probes. II. Hybridization of Oligonucleotides of Mixed Sequence to Rabbit β–globin DNA," Nucleic Acids Res., 9:879 (1981).
Britten and Davidson, in *Nucleic Acid Hybridisation,* (B.D. Hames and S.J. Higgins, eds.) (IRL Press, Washington, 1985)(pp. 3–15).
Mullis et al., "Specific Enzymatic Amplification of DNA In Vitro: The Polymerase Chain Reaction," Cold Spring Harbor Symposia, vol. LI, pp. 263 (1986).
Olsen and Venter (eds.), Benzodiazepine/GABA Receptor and Chloride Channels: Structural and Functional Properties, vol. 5 in *Receptor Biochemistry and Methodology Series* (Alan R. Liss, New York, 1986).
Covey et al., "Modulation of GABA$_A$ Receptor Function by Benz[e]indienes and Phenanthrenes," J. Med. Chem., 36:627 (1993).
Tanaka et al., "Picrotoxinin Receptor in the Central Nervous System of the American Cockroach: Its Role in the Action of Cyclodiene–Type Insecticides," Pestic. Biochem. Physiol., 22:117 (1990).
Matsumura et al., "GABA–Related Systems as Targets for Insecticides," in Sites of Action of Neurotoxic Pesticides, ACS Symposium Series 356 (Hollingworth and Green, eds.)(Am. Chem. Soc., Wash., 1987)(pp. 44–70).
Moss et al., "Cloned GABA Receptors are Maintained in a Stable Cell Line: Allosteric and Channel Properties," Eur. J. Pharmacol., 189.77 (1990).
Sambrook et al., (eds.), *Molecular Cloning,* 2d ed., (Cold Spring Harbor Laboratory, 1989).
Bender et al., "Chromosomal Walking and Jumping to Isolate DNA from the Ace and Rosy Loci and Biothorax Complex in *Drosophila melanogaster,*" J. Mol. Biol., 168:17 (1983).
Pardue, "In Situ Hybridization to DNA of Chromosomes and Nuclei," in *Drosophila: A Practical Approach,* Roberts (ed.), (IRL Press Lt., Oxford, 1986).
Sanger et al., "DNA Sequencing with Chain–Terminating Inhibitors," Proc. Natl. Acad. Sci. USA 74:5463 (1977).
Ymer et al., "GABA$_A$ Receptor β Subunit Heterogeneity: Functional Expression of Cloned cDNAs," EMBO J., 8:1665 (1989).

(List continued on next page.)

*Primary Examiner*—Laurie A. Scheiner
*Attorney, Agent, or Firm*—Medlen & Carroll, LLP

[57] ABSTRACT

The present invention relates to methods and reagents for drug and pesticide screening. Screening methods are disclosed employing normal and mutant receptors, allowing for the testing of large numbers of potentially useful compounds.

10 Claims, 18 Drawing Sheets

OTHER PUBLICATIONS

Schofield et al., "Sequence and Functional Expression of the $GABA_A$ Receptor Shows a Ligand–Gated Receptor Super Family," Nature 328:221 (1987).

ffrench–Constant et al., "Isolation of Dieldrin Resistance From Field Populations of Drosophila melanogaster (Diptera: Drosophilidae)," Econ. Entomol., 83:1733 (1990).

Mertz and Gurdon, "Purified DNAs are Transcribed After Microinjection into Xenopus Oocytes," Proc. Natl. Acad. Sci. USA 74:1502 (1977).

Garguilo and Worcel, "Analysis of the Chromatin Assembled in Germinal Vesicles of Xenopus Oocytes," J. Mol. Biol., 170:699 (1983).

Ryoji and Worcel, "Chromatin Assembly in Xenopus Oocytes: In Vivo Studies," Cell 37:21 (1984).

Kreig and Melton, "Developmental Regulation of a Gastrula–Specific Gene Injected Into Fertilized Xenopus Eggs," EMBO J., 4:3464 (1985).

Masu et al., "cDNA Cloning of Bovine Substance–K Receptor Through Oocyte Expression System," Nature 329:836 (1987).

Wilson et al., "Tissue–Specific Expression of Actin Genes Injected Into Xenopus Embryos," Cell 47:589 (1986).

Old and Primrose, Principles of Gene Manipulation, 4th ed., (Blackwell Scientific Publications, Oxford, 1989)(pp. 296–302).

Lummis, "GABA Receptors in Insects," Comp. Biochem. Physiol., 95:1 (1990).

Feigenspan et al., "Pharmacology of GABA Receptor Cl Channels in Rat Retinal Bipolar Cells," Nature 361:159 (1993).

Qian and Dowling, "Novel GABA Responses from Rod–Driven Retinal Horizontal Cells," Nature 361:162 (1993).

Bloomquist et al., "Excitation of Central Neurons by Dieldrin and Picrotoxinin in Susceptible and Resistant Drosophila melanogaster (Meigen)," Pestic. Sci., 32:463 (1991).

Pribilla et al., "The Atypical M2 Segment of the β Subunit Confers Picrotoxinin Resistance to Inhibitory Glycine Receptor Channels," EMBO J., 11:4305 (1992).

Beeman and Stuart, "A Gene for Lindane + Cyclodiene Resistance in the Red Flour Beetle (Coleoptera: Tenebrionidae)," J. Econ. Entomol., 83:1745 (1990).

Thompson et al., "Cloning and Sequencing of the Cyclodiene Insecticide Resistance Gene from the Yellow Fever Mosquito, Aedes aegypti: Conservation of the Gene and Resistance Associated Mutation with Drosophila," FEBS Lett., accepted for publication.

ffrench–Constant et al., "Molecular Cloning and Transformation of Cyclodiene Resistance in Drosophila: An Ivertebrate γ–Aminobutyric Acid Subtype A Receptor Locus," Proc. Natl. Acad. Sci. USA 88:7209 (1991).

Chen and Hodgetts, "Functional Analysis of a Naturally Occurring Variant Dopa Decarboxylase Gene in Drosophila melanogaster using P element Mediated Germ Line Transformation," Mol. Gen. Genet. 207:441 (1987).

Shotkoski and Fallon, "Genetic Changes in Methotrexate–Resistant Mosquito Cells," Arch. Insect Biochem. Physiol., 15:79 (1990).

Robertson et al., "A Stable Genomic Source of P Element Transposase in Drosophila melanogaster," Genetics 118:461 (1988).

Di Nocera and Dawid, "Transient Expression of Genes Introduced into Cultured Cells of Drosophila," Proc. Natl. Acad. Sci., 80:7095 (1983).

Hoch et al., "Primary Cultures of Mouse Spinal Cord Express the Neonatal Isoform of the Inhibitory Glycine Receptor," Neuron 3:339 (1989).

Andersen et al., "The Synthesis of Novel GABA Uptake Inhibitors. 1. Elucidation of the Structure–Activity Studies Leading to the Choice of (R)–1–[4, 4–Bis(3–methyl–2–thienyl)–3–butenyl]–3–piperidinecarboxylic Acid (Tiagabine) as an Anticonvulsant Drug Candidate," J. Med. Chem., 36:1716 (1993).

ffrench–Constant and Rocheleau, "Drosophila γ–Aminobutyric Acid Receptor Gene Rdl Shows Extensive Alternative Splicing," J. Neurochem., 60:2323 (1993).

Thompson et al., "Conservation of Cyclodiene Resistance––Associated Mutations in Insects," Insect Mol. Biol., In press.

Steichen and ffrench–Constant, "Amplification of Specific Cyclodiene Insecticide Resistance Alleles by the Polymerase Chain Reaction," Pesticide Biochem. Physiol., In press.

FIG. 10
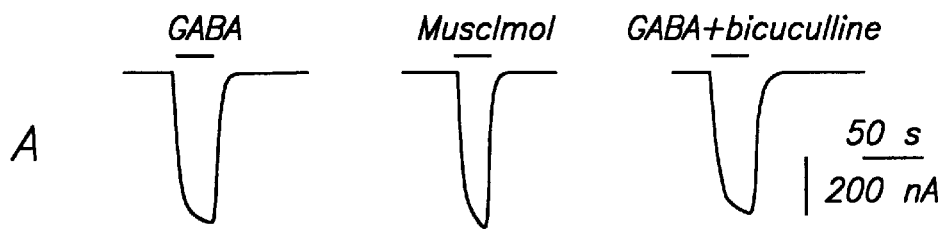
A — Wild-type: GABA, Muscimol, GABA+bicuculline (50 s, 200 nA)
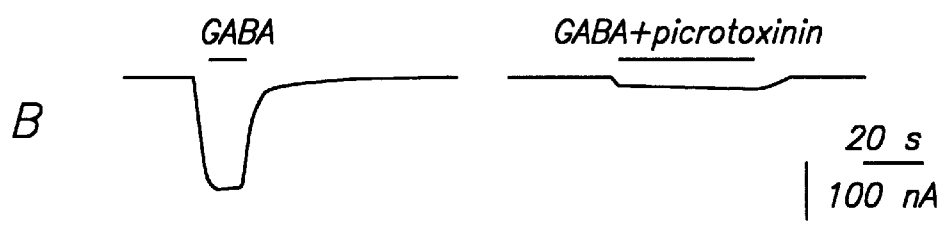
B — GABA, GABA+picrotoxinin (20 s, 100 nA)
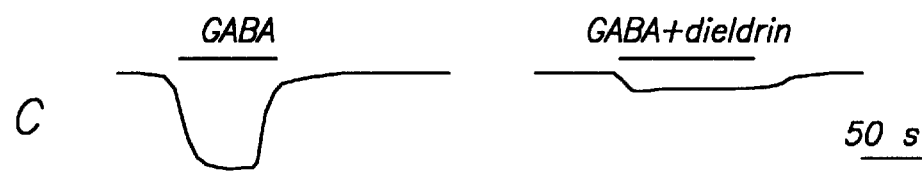
C — GABA, GABA+dieldrin (50 s)
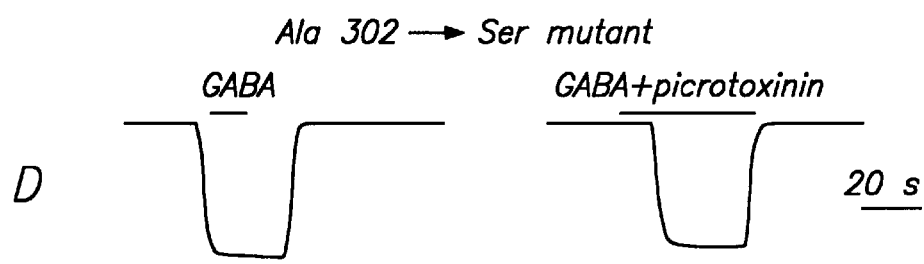
D — Ala 302 → Ser mutant: GABA, GABA+picrotoxinin (20 s)
E — GABA, GABA+dieldrin (20 s)

```
Aedes       1 ......MSLEIEVPHVRCPSLGVLILTLNLALFLPQTINRTPPYVLAGTG 44
              ,|,  .: ,|,| |,:: |,:|:|| ,:| ::  , | |:||
Drosophila  1 MSDSKMDKLARMAPLPRTPLLTIW,LAINMALIAQETGHKRIHTVQAATG 49

Aedes      45 GGSMLGDVNISAILDSFSVGYDKRVRPNYGGPPVEVGVTMYVLSISSVSE 94
              |||||||||||||||||||:||||||||||||||||||||||||||||||
Drosophila 50 GGSMLGDVNISAILDSFSVSYDKRVRPNYGGPPVEVGVTMYVLSISSVSE 99

Aedes      95 VLMDFTLDFYFRQFWTDPRLAYRKRPGVETLSVGSEFIKNIWVPDTFFVN 144
              ||||||||||||||||||||||||||||||||||||||||||||||||||
Drosophila 100 VLMDFTLDFYFRQFWTDPRLAYRKRPGVETLSVGSEFIKNIWVPDTFFVN 149

Aedes     145 EKQSYFHIATTSNEFIRVHHSGSITRSIRLTITASCPMGLQYFPMDRQLC 194
              ||||||||||||||||||||||||||||||||||||||.|||||||||||
Drosophila 150 EKQSYFHIATTSNEFIRVHHSGSITRSIRLTITASCPMNLQYFPMDRQLC 199

Aedes     195 HIEIESFGYTMRDIRYFWKDGLSSVGMSSEVELPQFRVLGHRQRATEINL 244
              |||||||||||||||||:||||||||||||||||||||||||||||||||
Drosophila 200 HIEIESFGYTMRDIRYFWRDGLSSVGMSSEVELPQFRVLGHRQRATEINL 249

Aedes     245 TTGNYSRLACEIQFVRSMGYYLIQIYIPSGLIVIISWVSFWLNRDATPAR 294
              |||||||||||||||||||||||||||||||||:||||||||||:|||||
Drosophila 250 TTGNYSRLACEIQFVRSMGYYLIQIYIPSGLIVVISWVSFWLNRNATPAR 299

Aedes     295 VALGVTTVLTMTTLMSSTNAALPKISYVKSIDVYLGTCFVMVFASLLEYA 344
              |||||||||||||||||||||||||||||||||||||||||||||||||||
Drosophila 300 VALGVTTVLTMTTLMSSTNAALPKISYVKSIDVYLGTCFVMVFASLLEYA 349

Aedes     345 TVGYMAKRIQIGKQRFMAIQKIAEQKKQQAADANHPPPPPP......... 385
              |||||||||:| ||||||||||||||||| ,:||:,,: |
Drosophila 350 TVGYMAKRIQMRKQRFMAIQKIAEQKKQQLDGANQQQANPNPNANVGGPG 399

Aedes     386 .....................VSDHSHGHG,HGHSHGHQHTPKQQMG 410
                                    ..:|:|||| |:|||||,|,||| ::
Drosophila 400 GVGVGPGGPGGPGGGVNVGVGMGMGPEHGHGHGHHAHSHGHPHAPKQTVS 449

Aedes     411 SRS.................GPLFQEVRFKVHDPKAHSKGGTLENTING 442
              ,|,.              |||||||||||||||||||||||||:||
Drosophila 450 NRPIGFSNIQQNVGTRGCSIVGPLFQEVRFKVHDPKAHSKGGTLENTVNG 499

Aedes     443 GRG..........GGGPPGGGGGPPGGGG...GGPDEESGAPQHLIHPG 478
              |||          |||||||||..||||    ||.|.|.:.|.||:|||
Drosophila 500 GRGGPQSHGPGPGQGGGPPGGGGGGGGGGPPEGGGDPEAAVPAHLLHPG 549

Aedes     479 ...KDINKLLGITPSDIDKYSRIVFPVCFVCFNLMYWIIYLHVSDVVADD 525
                 ||||||||||||||||||||||||||||||||||||||||||||||
Drosophila 550 KVKKDINKLLGITPSDIDKYSRIVFPVCFVCFNLMYWIIYLHVSDVVADD 599

Aedes     526 LVLLGEEK* 534
              |||||||
Drosophila 600 LVLLGEE*, 607
```

FIG. 19

| AMINO ACID: | | L | N | R | N | A | T | P | A | R | V | S/G | L | G | V | T | T |
|---|---|---|---|---|---|---|---|---|---|---|---|---|---|---|---|---|---|
| | | | | | | | | | | | | A→ | ↓S | | | | | |
| D. melanogaster | S | CTC | AAT | CGC | AAT | GCA | ACG | CCG | GCG | CGT | GTG | GCG | CTC | GGT | GTG | ACA | ACC |
| & D. simulans allele 1 | R | CTC | AAT | CGC | AAT | GCA | ACG | CCG | GCG | CGT | GTG | TCG | CTC | GGT | GTG | ACA | ACC |
| | | | | | | | | | | | | ↓S | | | | | |
| D. simulans allele 2 | S | CTC | AAT | CGC | AAT | GCA | ACG | CCG | GCG | CGT | GTG | GCG | CTC | GGT | GTG | ACA | ACC |
| | R | CTC | AAT | CGC | AAT | GCA | ACG | CCG | GCG | CGT | GTG | GGG | CTC | GGT | GTG | ACA | ACC |
| | | | | | | | | | | | | ↓G | | | | | |
| P. americana | S | CTG | AAC | CGC | AAY | GCG | ACG | CCC | GCC | CGA | GTC | GCC | CTC | GGG | GTT | ACC | ACT |
| | R | CTS | AAC | CGC | AAT | GCG | ACG | CCC | GCC | CGA | GTC | TCC | CTC | GGG | GTT | ACC | ACC |
| | | | | | | | | | | | | ↓S | | | | | |
| M. domestica | S | CTT | AAT | CGT | AAT | GCT | ACA | CCA | GCC | CGT | GTA | GCT | TTA | GGT | GTC | ACC | ACT |
| | R | CTT | AAT | CGT | AAT | GCT | ACA | CCA | GCC | CGT | GTA | TCT | TTA | GGT | GTC | ACC | ACC |
| | | | | | | | | | | | | ↓S | | | | | |
| T. castaneum | S | CTG | AAT | CGT | AAC | GCT | ACT | CTC | GCC | AGA | GTG | GCT | CTG | GGG | GTC | ACC | ACT |
| | R | CTT | AAT | CGT | AAT | GCT | ACA | CCA | GCC | CGT | GTR | TCT | TTA | GGT | GTC | ACC | ACT |
| | | | | | | | | | | | | ↓S | | | | | |

FIG. 23

DRUG AND PESTICIDE SCREENING

The present application is a continuation-in-part of application Ser. No. 07/770,881, filed Oct. 4, 1991, now abandoned.

FIELD OF THE INVENTION

The present invention relates to methods and reagents for drug and pesticide screening.

BACKGROUND

The continuous and intensive use of insecticides against insect pests has resulted in the development of resistant strains. Resistance to cyclodiene insecticides accounts for more than 60% of reported cases of insecticide resistance, and has been documented in at least 277 species. ffrench-Constant et al., Proc. Natl. Acad. Sci. USA 90:1957 (1993). For example, several years of selection by dieldrin residual spraying for malaria control resulted in the resistance factor becoming a predominant characteristic of the *Anopheles gambiae* population, with a frequency of 90%. Metcalf and Flint, *Destructive and Useful Insects, Their Habits & Control*, 4th ed., (McGraw-Hill, New York, 1962)(p. 397).

Studies of insecticide resistance in more than 30 species indicate that only a limited number of independent mechanisms are involved. Many different classes of insecticides either attack the same target site, and/or are metabolized by the same degradative enzymes. ffrench-Constant et al., in: *Molecular Approaches to Fundamental and Applied Entomology*, (Springer-Verlag, New York, 1992) (pp. 1–37).

Despite this apparent conservatism in resistance mechanisms, and the continued design of many insecticides around targets in the insect nervous system, resistance is still poorly understood at the molecular level. This is due at least in part to the fact that most of the toxicological and biochemical studies on resistance have been done in pest species where comprehensive genetic and molecular studies are difficult to perform.

Current strategies to combat resistance often rely on the use of alternative compounds. However, the lack of understanding of the basis of resistance results in this strategy being one of trial and error. Compound analogs are simply put to the test in the field, without any significant prescreening for efficacy.

Thus, what is needed is an easy, reliable method to determine the safety and efficacy of newly developed insecticides. The method should be amenable to screening insecticides in an in vitro assay prior to any field testing. Since large numbers of compounds (e.g., compound libraries) need to be evaluated, this method should be such that automation is feasible.

DEFINITIONS

The term "pesticide" as used herein refers to any type of chemical compound which has lethal or sub-lethal effects on eukaryotic cells. Encompassed within "pesticide" are such compounds as insecticides, vermicides, mutagens, carcinogens, and any other compound useful for killing, mutating, or debilitating organisms such as insects. "Pesticides" include, but are not limited to polychlorinated hydrocarbons (such as DDT [dichlorodiphenyltrichloroethane] dieldrin, aldrin, chlordane and lindane) organophosphorous compounds, carbamates, and any other compound useful in the killing of pests.

The term "cyclodiene" refers to any chemical compound comprised of a cyclic member which contains two double bonds. "Cyclodiene" includes, but is not limited to aldrin, endrin, endossulfan, lindane and derivatives or metabolites thereof (e.g., dieldrin).

The term "drug" as used herein, refers to any medicinal substance used in humans or other animals. Encompassed within this definition are compound analogs, naturally occurring, synthetic and recombinant pharmaceuticals, hormones, antimicrobials, neurotransmitters, etc.

As used herein, the term "neurotransmitter" includes any compound which functions in the nervous system to result in the transmission of chemical signals between cells. Encompassed within this definition are substances released from the axon terminal of a presynaptic neuron on excitation, which diffuses across the synaptic cleft to either excite or inhibit the synaptic cleft to either excite or inhibit the target cell. False neurotransmitters are also included (e.g., a compound that can be released from presynaptic vesicles but that has little effect on postsynaptic receptors). Examples of neurotransmitters include, but are not limited to neuropeptides, acetocholine, and amino acids (e.g., GABA). Other compounds are also contemplated, including dopamine, norepinephrine, etc.

The term "permeant" refers to molecules which are capable of entering cells by means of ion channels or other mechanisms. "Permeant" includes, but is not limited to ions such as chloride, potassium, sodium, and thiocyanate.

The term "toxin" refers to any compound or molecule which is capable of causing cell death upon entering cells by means such as ion channels or other mechanisms. "Toxins" include, but are not limited to such compounds as thiocyanates.

The term "GABA" refers to γ-aminobutyric acid, a major inhibitory neurotransmitter in both vertebrates and invertebrates. Kuffler and Edwards, J. Neurophysiol., 21:589 (1965) Otsuka et al., Proc. Natl. Acad. Sci USA 56:1110 (1966); Usherwood and Grundfest, J. Neurophysiol., 28:497 (1965).

The term "GABA receptors" thus refers to structures expressed by cells and which recognize GABA. In vertebrates, several subunits of different types ($\alpha$, $\beta$, $\gamma$, $\delta$, or $\rho$) are assembled in an unknown stoichiometry to form a GABA-gated Cl$^-$ channel termed the GABA receptor. Olsen and Tobin, FASEB J. 4:1469 (1990). In invertebrates, only two GABA receptor subunits have been identified to date—a GABA$_A$ $\beta$ subunit homologue from the mollusc (*Lymnaea stagnalis*) (Harvey et al., EMBO J. 10:3239 (1991), and a novel subunit termed Rdl (from a mutant, resistant to dieldrin) from *Drosophila melanogaster*. In the fly, the Rdl subunit forms functional channels as a homomultimer. ffrench-Constant, Nature, in press.

The term "agonist" refers to molecules or compounds which mimic the action of a "native" or "natural" compound. Agonists may be homologous to these natural compounds in respect to conformation, charge or other characteristics. Thus, agonists may be recognized by receptors expressed on cell surfaces. This recognition may result in physiologic and/or biochemical changes within the cell, such that the cell reacts to the presence of the agonist in the same manner as if the natural compound was present.

The term "antagonist" refers to molecules or compounds which inhibit the action of a "native" or "natural" compound. Antagonists may or may not be homologous to these natural compounds in respect to conformation, charge or other characteristics. Thus, antagonists may be recognized by the same or different receptors that are recognized by an agonist (e.g., GABA). Antagonists may have allosteric effects which prevent the action of an agonist (e.g., prevent opening of the chloride ion channel). Or, antagonists may prevent the function of the agonist (e.g., by blocking the passage of chloride ions in the channels). In contrast to the agonists, antagonistic compounds do not result in physiologic and/or biochemical changes within the cell such that the cell reacts to the presence of the antagonist in the same manner as if the natural compound was present.

Picrotoxinin (PTX) is an example of a GABA antagonist which is recognized by the GABA receptor. "Picrotoxinin" is defined as the toxin component within "picrotoxin" (cocculin), an intensely bitter and very poisonous alkaloid isolated from the seed of *Anamirta cocculus*. Picrotoxin is a central nervous and respiratory system stimulant which may be used as a veterinary antidote to barbiturates. Budavari et al., (eds.), *Merck Index* (Merck & Co., Rahway, N.J., 1989) (p. 1177).

The term "host cell" or "cell" refers to any cell which is used in any of the screening assays for detection of resistance. "Host cell" or "cell" also refers to any cell which either naturally expresses particular receptors of interest or is genetically altered so as to produce these normal or mutated receptors.

As used herein, the term "diagnosis" refers to the determination of whether an insect or other organism is susceptible or resistant to a particular pesticide or other compound.

The term "hybridization" as used herein refers to the formation of sequence-specific, base-paired duplexes from any combination of nucleic acid fragments. Hybridization, regardless of the method used, requires some complementarity between the sequence of interest (the target sequence) and the fragment of nucleic acid used to detect the target sequence and/or perform the test (e.g., the probe). Thus, these duplexes may be completely complementary or may include mismatched sequences.

For example, where it is desired to detect simply the presence or absence of insect DNA or RNA, it is only important that the hybridization method ensures hybridization when the relevant sequence is present; conditions can be selected where both partially complementary probes and completely complementary probes will hybridize. However, other diagnostic applications may require that the method of hybridization distinguish between variant target sequences. For example, it may be of interest that a particular allelic variant is present.

Methods have been devised to enable discrimination between partial and complete complementarity. One approach is to take advantage of the temperature requirements of the specific hybridization under study. In typical melting curve experiments, such as those described by Wallace et al., Nucl. Acids Res., 6:35632 (1979) and Nucl. Acids Res. 9:879 (1981), it is observed that partially complementary probe-target duplexes display a lower thermal stability than do completely complementary probe-target duplexes. The best estimate is that a 1% mismatch causes a reduction in the thermal stability of duplexes, as measured by the duplex melting temperature ($T_m$), by 1° C. See R. J. Britten and E. H. Davidson, in: *Nucleic Acid Hybridisation,* (B. D. Hames and S. J. Higgins, eds) (IRL Press, Washington, 1985)(pp. 3–15). The $T_m$ is also affected by the length of the base-paired region of a duplex, according to the equation D=500/L, wherein D is the reduction in $T_m$ (0° C.) and L is the length of the base-paired duplex. The base composition of the duplex is another factor which affects its stability. In normal salt solutions, GC base pairs are more stable than AT pairs, thus the $T_m$ of a particular duplex is related to its GC content according to the equation $T_m$=0.41(% GC)+69.3. As used herein, the terms "substantial complementarity" or "substantially complementary" refer to a nucleic acid duplex in which the $T_m$ is within (plus or minus) 10° C. of the $T_m$ of a completely complementary duplex.

There are various applications that may require that the hybridization method distinguish between partial and complete complementarity. For example, it may be of interest to detect genetic polymorphisms. As used herein, the term "genetic polymorphisms" refers to the condition in which two or more different nucleotide sequences coexist in the same interbreeding population in a DNA sequence. In many instances, it is desirable to combine hybridization with other techniques (such as restriction enzyme analysis).

The term "probe" as used herein refers to a nucleic acid sequence which is used to detect the presence of a complementary sequence by hybridization.

The term "primer" as used herein refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "target" refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or DATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

As used herein, the term "PCR product" refers to the resultant mixture of compounds after two or more cycles of the PCR steps of denaturation, annealing and extension are complete. "PCR product" encompasses the case where there has been amplification of one or more segments of one or more target sequences.

As used herein, the term "nested primers" refers to primers that anneal to the target sequence in an area that is inside the annealing boundaries used to start PCR. K. B. Mullis, et al., Cold Spring Harbor Symposia, Vol. LI, pp. 263–273 (1986). Because the nested primers anneal to the target inside the annealing boundaries of the starting primers, the predominant PCR-amplified product of the starting primers is necessarily a longer sequence, than that defined by the annealing boundaries of the nested primers. The PCR-amplified product of the nested primers is an amplified segment of the target sequence that cannot, therefore, anneal with the starting primers.

As used herein, the term "amplification reagents" refers to those reagents (deoxyribonucleoside triphosphates, buffer, etc.), needed for amplification except for primers, nucleic acid template and the amplification enzyme.

As used herein, the terms "restriction endonucleases" and "restriction enzymes" refer to bacterial enzymes, each of which cut double-stranded DNA at or near a specific nucleotide sequence.

As used in the present invention, the term "transformation" refers to the introduction of foreign genetic material into a cell or organism. Transformation may be accomplished by any method known which permits the successful introduction of nucleic acids into cells and which results in the expression of the introduced nucleic acid. For example, transformation may be used to introduce cloned DNA encoding a normal or mutant GABA receptor into a cell which normally does not express this receptor.

"Transformation" includes but is not limited to such methods as transfection, microinjection, electroporation, and lipofection (liposome-mediated gene transfer). Transformation may be accomplished through use of any expression vector. For example, the use of baculovirus to introduce foreign nucleic acid into insect cells is contemplated. The term "transformation" also includes methods such as P-element mediated germline transformation of whole insects.

"Field organisms" are insects or other organisms collected from their natural or an artificial habitat. For example, mosquitoes may be collected from bodies of water, near agricultural areas, or from insect traps. Such organisms may also be collected from the bodies of other animals (e.g., mosquitoes removed from the skin of chickens used as viral encephalitis sentinel animals) or from vegetation. Field organisms include any organisms collected and isolated from an environment other than the laboratory setting.

As used in the present invention, the term "beneficial organisms" refers to insects or other animals which provide benefits to successful agriculture. These insects may act as predators of insects which are known to be harmful to crops. In this case, the predatory beneficial insects use the harmful insects as a food source. The term also encompasses organisms which kill harmful insects but do not utilize the harmful insects as a food source.

As used in the present invention, the term "harmful insects" refers to insect species or varieties which are destructive to agriculture (e.g., farming), are vectors or hosts of disease-causing microorganisms (including parasites), or cause harm to flora or fauna. The term encompasses "pest" insects including, but not limited to such insects as cockroaches, flies, spiders, etc. It also encompasses insects such as mosquitoes, beetles, sandflies, ticks and any other members of the insect family which cause harm to animals or plants.

The term "sample" as used herein refers to any type of material obtained from any organism, including humans, insects or other animals (e.g., any bodily fluid or tissue), cell or tissue cultures, cell lines, primary cell cultures. "Sample" also encompasses any of these cells which naturally express normal or mutant GABA receptors, and cells which have been transformed to express normal or mutant GABA receptors. Such transformed cells may transiently or permanently express normal or mutant GABA receptors.

SUMMARY OF THE INVENTION

The present invention relates to methods of expression of GABA receptors for use in drug and pesticide screening. In particular, the present invention provides purified and isolated nucleic acid sequences encoding invertebrate GABA receptors. While it is not intended that the invention be limited by specific embodiments, the preferred sequences are selected from the group comprising SEQ ID NOS:2, 3, 5, 7, and 9. The nucleic acid sequences are particularly useful in host cells. Such sequences render host cells capable of expressing the GABA receptor protein, or portions thereof. The present invention contemplates GABA receptor proteins having amino acid sequence selected from the group comprising SEQ ID NOS:1, 4, 6, and 8.

It is not intended that the present invention be limited by the nature of the host cell. It is preferred that the host cell is eukaryotic. In one embodiment, the host cell is mammalian. In another embodiment, the host cell is an insect cell. In still another embodiment, the host cell is within a living insect.

The present invention contemplates the use of cells expressing GABA receptors in compound screening assays. In one embodiment, the present invention contemplates a compound screening method comprising: a) providing, in any order: i) a reaction vessel; ii) a plurality of cells having a plurality of closed ion channels; iii) a compound which is capable of opening said ion channels; iv) a toxin capable of entering said cells through open ion channels so as to bring about cell death; and v) a potential antagonist suspected of being able to prevent the opening of said ion channels and thereby prevent said toxin from entering said cells; b) combining said cells, said compound, said toxin, and said potential antagonist within said reaction vessel under conditions such that said compound is free to interact with said cells; and c) detecting said interaction. The compound used for opening said ion channels may be a neurotransmitter, such as GABA.

In another embodiment, the present invention contemplates a compound screening method comprising: a) providing, in any order: i) a reaction vessel; ii) a plurality of cells having a plurality of closed ion channels; iii) a potential agonist suspected of being able to open said ion channels; and iv) a toxin capable of entering said cells through open ion channels so as to bring about cell death; b) combining said cells, said potential agonist, and said toxin within said reaction vessel under conditions such that said natural agonist is free to interact with said cells; and c) detecting said interaction. The potential agonist may be a drug that, if found to act appropriately in the screening assay of the present invention, could be useful as a therapeutic.

In either embodiment, the ion channel may be an integral portion of a GABA receptor complex, or for that matter, an integral portion of a mutated GABA receptor complex. In a preferred embodiment, the toxin comprises a thiocyanate salt, such as sodium thiocyanate or potassium thiocyanate.

In both embodiments, it is preferred that the detecting step involve determining the viability of the cells, which can be done in a microwell of a microtiter plate. Again, it is not intended that this be limited by the nature of the cells.

In a preferred embodiment, the cells are insect cells having a functional DNA sequence selected from the group comprising SEQ ID NOS:2, 3, 5, 7, and 9, or a portion thereof, which renders them capable of expressing an invertebrate GABA receptor or portion thereof.

The present invention also contemplates a method for detecting a nucleic acid sequence in a sample, comprising: a) providing, in any order: i) a sample suspected of containing nucleic acid encoding a GABA receptor; ii) amplification reagents; iii) one or more amplification enzymes; iv) primers capable of initiating amplification of a portion of said nucleic acid sequences; and v) means for containing a reaction; b) adding to said reaction containing means, in any order, said nucleic acid, said one or more primers, and said amplification reagents, to make a reaction mixture; and c) adding said one or more amplification enzymes to said reaction mixture, so as to initiate amplification of at least a portion of said nucleic acid; and d) detecting said nucleic acid. This assay is useful for, among other things, diagnosing pesticide resistance and genotyping insects.

While it is not intended that the present invention be limited by specific embodiments, a preferred embodiment of the present invention contemplates primers selected from the group comprising SEQ ID NOS:10–20. For ease of detection, it is preferred that the primers used in the detection assay have a detectable label, whether a radioisotope, enzyme and flurogenic substance or other type of molecule (e.g. biotin, etc.).

It is not intended that the present invention be limited by the nature of the sample. In a preferred embodiment, the sample comprises a cell lysate (e.g. a lysate of insect cells).

DESCRIPTION OF THE DRAWINGS

FIG. 3(A) of FIG. 3 shows the hydropathy profile for rat $\beta_1$.

FIG. 3(B) of FIG. 3 shows the hydropathy profile for rat $\beta_2$.

FIG. 3(C) of FIG. 3 shows the hydropathy profile for rat $\beta_3$.

FIG. 3(D) of FIG. 3 shows the hydropathy profile for Drosophila $\beta$.

FIG. 10 shows the currents recorded under voltage-clamp conditions from Xenopus oocytes injected with normal and mutant GABA receptor cDNA.

FIG. 10(A) of FIG. 10 shows the results for Xenopus oocytes injected with normal GABA receptor cDNA and exposed to GABA, muscimol, and GABA plus bicuculline.

FIG. 10(B) of FIG. 10 shows the results for Xenopus oocytes injected with normal GABA receptor cDNA and exposed to GABA, and GABA plus PTX.

FIG. 10(C) of FIG. 10 shows the results for Xenopus oocytes injected with mutant GABA receptor cDNA and exposed to GABA, and GABA plus PTX.

FIG. 10(D) of FIG. 10 shows the results for Xenopus oocytes injected with mutant GABA receptor cDNA and exposed to GABA, and GABA plus dieldrin.

FIG. 10(E) of FIG. 10 shows the results for Xenopus oocytes injected with mutant GABA cDNA and exposed to GABA, and GABA plus dieldrin.

FIG. 14(A) of FIG. 14 shows the PASA PCR products for homozygous susceptible (SS) and homozygous resistant (RR; allele 2) D. simulans with the forward primer at a range of $MgCl_2$ concentrations.

FIG. 14(B) of FIG. 14 shows the PASA PCR products for homozygous susceptible (SS) and homozygous resistant (RR; allele 2) D. simulans with the reverse primer at a range of $MgCl_2$ concentrations.

FIG. 14(C) of FIG. 14 shows the PASA PCR products for homozygous susceptible (SS) and homozygous resistant *D. melanogaster* with the forward primer at a range of $MgCl_2$ concentrations.

FIG. 14(D) of FIG. 14 shows the PASA PCR products for homozygous susceptible (SS) and homozygous resistant (RR; allele 1) *D. simulans* with the reverse primer at a range of $MgCl_2$ concentrations.

FIG. 15(A) of FIG. 15 shows the PASA PCR products from homozygous resistant *D. melanogaster* strains 1–23.

FIG. 15(B) of FIG. 15 shows the PASA PCR products from homozygous resistant *D. melanogaster* strains 24–46.

FIG. 16(A) of FIG. 16 shows the amplification of cyclodiene resistance allele 1 from homozygous resistant *D. simulans* strains.

FIG. 16(B) of FIG. 16 shows the amplification of cyclodiene resistance allele 2 from homozygous resistant *D. simulans* strains.

FIG. 19 compares the predicted amino acid sequence of Drosophila cyclodiene resistance gene Rdl with its homolog from the *A. aegypti* clone 2.1.3.

FIG. 23 shows the nucleotide sequence and deduced amino acid sequence of the 80 bp Rdl product from cyclodiene and resistant insects.

DESCRIPTION OF THE INVENTION

Figure 1:
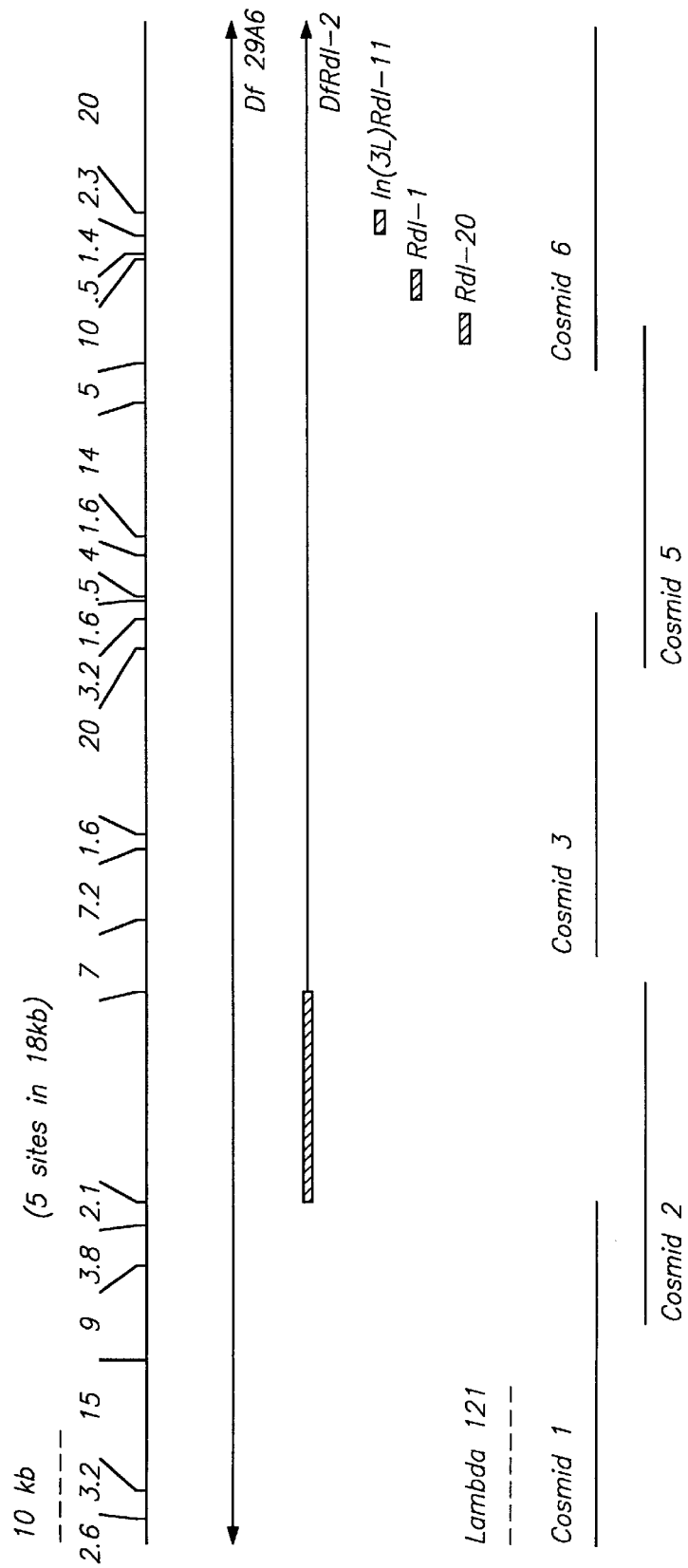
FIG. 1 depicts the EcoR1 restriction map of the polytene subregion 66F of D. melanogaster.

The present invention relates to methods and reagents for drug and pesticide screening. In particular, the present invention relates to 1) nucleic acid sequences encoding normal and mutant GABA receptors, 2) cells (from any organism, including humans) used to express these normal and mutant forms of the receptor, including transformed cells as well as cells transiently expressing the receptor, 3) screening methods to detect resistance and susceptibility of cells to test compounds such as pesticides, including methods to detect differential toxicity, in which exposure of different cell types are compared with exposures to different test compounds, 4) methods to create insect resistance to pesticides, as well as methods to preserve insect susceptibility to pesticides, and 5) methods to "diagnose" pesticide resistance in field samples, including methods to genotype field and laboratory insects for detection of resistance to various pesticides.

GABA is known to mediate neuronal inhibition by opening a chloride channel which is integral to the GABA receptor. This receptor is also the target of a variety of therapeutic compounds. Olsen and Venter (eds.), Benzodiazepine/GABA Receptor and Chloride Channels: Structural and Functional Properties, (Alan R. Liss, New York, 1986). Thus, modulation, activation, or inhibition of the GABA receptor may have pronounced effects on nervous system function.

In addition to the GABA binding site of the GABA receptor/chloride channel complex, there are additional binding sites for ligands that may either allosterically modulate the gating actions of GABA or initiate the influx of chloride in the absence of GABA. Covey et al., J. Med. Chem., 36:627 (1993). These additional sites have been pharmacologically defined as benzodiazepine, barbiturate, picrotoxin, and steroid binding sites. Drugs which bind to these allosteric sites have proven to be useful anxiolytics, sedative hypnotics, anticonvulsants and anesthetics.

Cyclodiene insecticides (e.g., dieldrin) inhibit chloride ion transport regulated by the GABA receptor, thereby blocking functional insect neuronal GABA receptors. Cyclodienes are thought to act at the picrotoxinin (PTX) binding site within the GABA receptor/chloride ionophore complex. Tanaka et al., Pestic. Biochem. Physiol., 22:117 (1990). Picrotoxinin (PTX) and cyclodiene insecticides are GABA receptor antagonists which competitively displace each other from the same binding site. Insects and vertebrates showing resistance to cyclodienes also show cross-resistance to PTX. Ligand binding studies in strains of the German cockroach (*Blatella genmanica*) have shown that PTX binding sites on the GABA receptor of resistant strains possess only one tenth of the affinity for PTX of those in susceptibles; resistant strains may also show a reduction in the number of receptors. Matsumura et al., in: *Sites of Action of Neurotoxic Pesticides*, ACS Symposium Series 356 (Am. Chem. Soc., Wash., 1987)(pp. 44–70). However, the insect GABA receptor shows critical pharmacological differences from the vertebrate receptor, which may lead to development of insect-specific insecticides with greater safety for vertebrate exposure.

As described herein, resistance to cyclodiene insecticides in Drosophila is caused by single base pair mutations within the same codon of a GABA receptor subtype A gene Rdl. The amino acid which is substituted by these mutations is within the second membrane spanning region of the receptor which is thought to line the chloride ion channel pore.

Normal and Mutant Nucleic Acid Sequences

Because this invention includes methods to detect and genotype insects which may be resistant to insecticides which affect the GABA receptor, the nucleic acid sequences of normal and mutated GABA receptors are included. These sequences may be isolated, purified and cloned from normal and mutant insects. Thus, the naturally occurring gene which is responsible for the expression of the GABA receptor or one of its subunits may be used in this invention. In addition to the naturally occurring gene, mutated genes are also included. Expression of these mutated genes result in the production of GABA receptors on cells or by whole organisms which may or may not confer resistance to insecticides or other GABA receptor antagonists.

The cDNA's of these sequences are also included as they may be used to transform cells to express normal or mutated GABA receptors. Transformation may be accomplished by any method known (e.g., microinjection, transfection, etc.) which permits the introduction of nucleic acid into a cell.

These nucleic acid sequences may be used to detect mutants by the polymerase chain reaction (PCR) and/or hybridization. PCR may be used to produce multiple copies of these normal and mutant sequences for use in various diagnostic tests, including development of a PCR-based kit for research, laboratory or field use. Normal and mutant sequences may also be used for in situ hybridization methods to detect the presence of normal or mutant GABA receptors in tissue sections or other samples.

Cells Which Express Normal or Mutant GABA Receptors

In order to determine the susceptibility of cells to insecticides or other compounds which affect the GABA receptor complex, cells must be utilized which express this receptor. Transformation results in the production of cells which express the receptor of interest, whether it be a normal or mutated version.

Cells may be obtained from a variety of sources and may either naturally express the GABA receptor or be transformed so that this complex is expressed. These cells may be obtained from any animal, including humans or other mammals, insects, or amphibians. In addition to cells obtained from field specimens, transformed cells and cell lines which express these receptors are also contemplated. Transformed cells and cell lines may be manipulated so that they express mutated GABA receptors. Transformed cells which express the GABA receptor may or may not be established as stable cell cultures. Where stable, this allows for use in repetitive tests. Where the receptors are only transiently expressed, the cells may be transformed, utilized in a screening assay, and then discarded (e.g., cells isolated from laboratory or field organisms).

Screening Assay Systems

The screening assays are contemplated as utilizing various host cell systems (e.g., cells naturally expressing natural or mutant GABA receptors or transformed cells so as to express these receptors). Two assay formats are contemplated by the present invention. In the first format, "GABA agonists" are identified by employing a cell toxin which permeates the open channel (preferably a chloride ion channel) and thus kills the cells. GABA agonists act by mimicking the action of GABA on GABA receptors. In the absence of GABA or a GABA agonist, the ion channel remains closed and impermeable to the toxin. An agonist is thereby detected if the channels are opened and there is cell death. Thus, if the compound to be tested does not signal the cells to open their chloride ion channels, it is not a GABA agonist.

In the second format, "GABA antagonists" are identified. GABA and the suspected GABA antagonist are tested in combination on GABA receptor-expressing cells, in the presence of a toxin. In the presence of GABA only, the GABA will stimulate the cells to open their Cl⁻ channels and the cells will die. In the test system, the action of GABA may be countered by the action of an antagonist. If the compound is a GABA antagonist, the channel will be blocked and the cells will remain viable.

It is also contemplated that the cells used in these screening assays will express mutant GABA receptors. These cells may either naturally express the mutant receptor, or transformation may be used to cause the cells to express the receptor. These mutated receptors may or may not confer resistance to the pesticide used in the assay. If the mutated receptor does not recognize the pesticide as a GABA agonist, the cells in the first screening assay format will live. If the compound acts on a mutated receptor as a GABA antagonist in the second assay format, the cells will remain viable. Thus, the function of the mutated receptors may be observed in either assay system.

Importantly, the use of potential agonists or antagonists in these assay systems should allow for the detection of new compounds (e.g., pesticides or drugs) which overcome existing or potential resistance mechanisms. That is to say, despite the presence of a mutated GABA receptor resistant to channel block by cyclodienes, screening of compound libraries should result in the detection of other pesticides which will block GABA-gated chloride channels resistant to cyclodienes.

Thus, in both assay systems, the action of the compound on the cells is determined by comparing the percentages of live and dead cells (e.g., in a fluorescence-based live/dead detection kit). Also, both assay systems may be used to screen many compounds. Importantly, the method is very amenable to automation, providing many benefits such as high throughput and reducing the amount of personnel time necessary to perform the assay. The present invention offers a radical change from the cumbersome methods previously used to screen for pesticides.

Either screening assay system may be modified so as to permit observations of differential toxicity. Differential toxicity may be observed when one cell type is resistant to the tested pesticide and another cell type is susceptible to the same pesticide. For example, a particular insect cell type may be susceptible to the action of a pesticide while a particular mammalian cell type or receptor expressed within the cell is resistant. Such an observation indicates that the tested pesticide will be toxic for the insect but safe for use on or around mammals. Should the opposite results be observed (the insect is resistant while the mammal is susceptible), this indicates that the pesticide is not optimum for mammalian safety.

Differential toxicity is also demonstrated when a receptor from a specific harmful insect pest is susceptible to the pesticide, while a beneficial insect is resistant to the pesticide. For example, a mosquito (e.g., Aedes sp.) cell expressing GABA receptors may be susceptible to the action of a test compound while cells expressing GABA receptors from insects used in biological pest control (e.g., ladybugs, etc.) are resistant. If the opposite results are observed (the harmful insect is resistant while the beneficial insect is susceptible), the scope of use will be more limited.

These assays may be used in any combination appropriate for the field situation involved. For example, the results for harmful and beneficial insects may be compared with those obtained for livestock which are maintained near the location of pesticide application.

Creation of Pesticide Resistance/Susceptibility in Insects

The present invention also contemplates the creation of resistance or susceptibility to pesticides. These methods include the introduction of multiple copies of the genes encoding either mutant or normal GABA receptors into cells or whole insects. Upon introduction of the gene coding a resistant GABA receptor into a beneficial insect, the insect may be rendered resistant to the effects of the pesticide. Sufficient copy numbers of the nucleic acid must be incorporated into the cell in order to achieve successful expression of the normal or mutant GABA receptor.

Insects with the inserted nucleic acid which renders their GABA receptors unable to recognize the pesticide may then be used in combination with the pesticide in the field to help reduce or eliminate the presence of harmful insects.

In contrast, introduction of the gene coding for the normal GABA receptor may render an insect susceptible to the action of a pesticide. Thus, an insect which may previously have been resistant to the pesticide will be killed. Thus, this invention contemplates the introduction of mutant or susceptible gene copies into field populations of insects in order to improve control via pesticides.

"Diagnosis" of Pesticide Resistance and Genotyping of Field Specimens The present invention also contemplates methods which permit "diagnosis" of pesticide resistance or susceptibility in field collected insects. This is accomplished by using DNA obtained from field insects in the screening assay described above.

Genotyping of field collected insects is also contemplated. Genotyping of insect resistance and susceptibility based on the use of the GABA receptor necessitated cloning of normal GABA and mutated GABA receptor genes in the present invention. By using the polymerase chain reaction (PCR) in conjunction with restriction endonucleases, the genotype of field insects may be observed. This permits the molecular diagnosis and determination of resistance frequencies useful in monitoring field organisms which may be harmful or helpful to agriculture.

DESCRIPTION OF PREFERRED EMBODIMENTS

As indicated in the general description, the present invention contemplates the use of nucleic acid sequences of normal and mutated GABA receptors. The amino acid sequence of the normal Drosophila GABA receptor predicted from the sequenced DNA is shown in SEQ ID NO:1. The DNA sequence is shown in SEQ ID NO:2. Nucleic acid sequences of known mutated receptors are shown in SEQ ID NO:3, SEQ ID NO:5 and SEQ ID NO:7. The corresponding amino acid sequences are shown in SEQ ID NO:4, SEQ ID NO:6, and SEQ ID NO:8, respectively.

As discussed further below, these sequences may be naturally present in the cells in the assay system. Or, these sequences may be inserted into the cells through such means as microinjection (e.g., Xenopus oocytes used in an expression system), transformation, transfection, etc. These transformed cells may or may not be comprised of stable cell cultures or lines.

Host cells used in the screening assay may be comprised of stable, transformed cell lines developed from insects or vertebrates and available through such sources as the American Type Culture Collection (ATCC). Examples of these cells include, but are not limited to human neuroblastoma cell lines such as SK-N-SH (ATCC HTB 11), SK-N-MC (ATCC HTB 10) and IMR-32 (ATCC CCL 127); murine neuroblastoma cell lines such as NB41A3 (ATCC CCL 147) Neuro-2a (ATCC CCL 131); the mouse brain tumor cell line $BC_3H1$ (ATCC CRL 1443); Drosophila cell lines, mosquito cell lines such as ATCC CCL 126 (*A. albopictus* larvae), ATCC CRL 1660 (*A. albopictus,* clone C6/36 larvae), ATCC CCL 125 (*A. aegypti* larvae), and TRA-171 (ATCC CRL 1591, *Toxorhynchites amboinensis* larvae); and other insects such as the fall armyworm ovarian cell line Sf9 (ATCC CRL 1711), the moth (*Antheraea eucalypti*) ovarian cell line (ATCC CCL 80); and other cells. Host cells may also be comprised of cells transformed to produce GABA receptors, such as the Chinese hamster ovary cells of Moss et al. which express bovine $\alpha_1$ and $\beta_1$. Moss et al., Eur. J. Pharmacol., 189:77 (1990).

In order to screen large libraries of compounds (e.g., drugs, new pesticides, etc.), the screening assays of the present invention are preferably conducted in a microplate format. These assays are based on the observation that permeant ions such as thiocyanate readily enter cells through the chloride ion channels. As thiocyanate ions are seven times more permeant than chloride and are highly toxic upon entering cells, it is a useful toxin for use in these assays.

When GABA (the natural agonist) and thiocyanate (sodium or potassium) are added to cells present in the wells of microtiter plates, the cells will bind GABA, opening the chloride ion channels and permitting intake of thiocyanate, which results in cell death.

In the first screening assay, cultured cells which express GABA receptors are placed in reaction tubes such as the wells of a microtiter plate. In the test wells, the compound suspected of being a GABA agonist and thiocyanate are co-applied to the cells. As GABA is responsible for opening the $Cl^-$ channel, if the suspected agonist permits the opening of the channel, thiocyanate will enter the cells and kill them. Compounds which do not act as GABA agonists will not open the $Cl^-$ channel, thiocyanate is prevented from entering the cells, and the cells remain viable.

In the second format, "GABA antagonists" are identified. GABA and the suspected GABA antagonist are tested in combination with a toxin. In the control wells with GABA only, the GABA will stimulate the cells to open their $Cl^-$ channels and the cells will die due to the entrance of the permeant toxin. In the test wells, the action of GABA may be countered by the action of an antagonist. If the compound is a GABA antagonist, the channel will be blocked and the cells will remain viable.

In the second screening assay, cultured cells which express GABA receptors are placed in reaction tubes such as the wells of a microtiter plate. In the test wells, the compound to be tested (e.g., dieldrin, etc.), GABA, and thiocyanate are co-applied to the cells. As binding of GABA results in the opening of the $Cl^-$ channel, if the test compound does not block entry of thiocyanate within the cells, the cells will die. If the compound blocks the ion channel, thiocyanate is prevented from entering the cells, and the cells remain viable.

Detection and differentiation of live and dead cells is preferably based on the presence of ubiquitous intracellular esterase activity, as demonstrated by the "live-dead" kit produced by Molecular Probes (Eugene, Oreg.). In this system, two dyes, calcein AM and ethidium homodimer (EthD-1) are used to detect cell viability by testing both intracellular esterase activity and plasma membrane integrity. Cell esterase activity is determined by the enzymatic conversion of cell permeant calcein AM to fluorescent calcein (530 nm). The second dye, EthD-1 enters dead cells with damaged membranes and undergoes an enhancement of fluorescence upon binding of nucleic acids (600 nm). EthD-1 is excluded by the intact plasma membrane of intact living cells. By scanning the microtiter plate with a fluorescent plate reader using these two wavelengths (e.g., "Cytofluor," Millipore, Houston, Tex.), and taking the differential values, cells can be automatically scored in percent alive or dead. Simple automation through use of any robotic or other mechanized system of microplate handling and analysis is thus feasible. Efficient primary screens for new compounds, as well as secondary screens for known GABA-active (or other receptor) compounds is thereby made possible.

The present invention offers a radical change from the cumbersome methods previously in use to screen for pesticides. Importantly, the method of the present invention can be carried out in microtiter plates (e.g., Costar 96-well plates available from various vendors such as BioRad, Richmond, Calif.). Because of these features, the method of the present invention is highly amenable to automation.

In one preferred embodiment of the above assay methods, the cells are insect cells which are not established cell lines (i.e., the cells have been isolated from field-collected insects). In this embodiment, the action of potential GABA agonists and antagonists is observed in primary neuronal cultures from laboratory or field samples of insects.

In another embodiment of the above assay methods, the cells are vertebrate cells which are not established cell lines (i.e., the cells have been isolated from a vertebrate species, including humans and other animals such as livestock or wildlife). In this embodiment, the action of potential GABA agonists and antagonists is observed.

In another embodiment of the above assay methods, the cells are stable, vertebrate cell lines which have been transfected or transformed to express mutant GABA receptors. In this embodiment, the action of potential GABA agonists and antagonists is observed.

In another preferred embodiment of the above assay methods, the cells are stable, insect cell lines which have been transfected or transformed to express mutant GABA receptors. In this embodiment, the action of potential GABA agonists and antagonists is observed.

In another preferred embodiment of the above assay methods, the cells are insect cells which are not established cell lines but are primary neuronal cultures, which have been transfected or transformed to express mutant GABA receptors. In this embodiment, the action of potential GABA agonists and antagonists is observed.

In another embodiment of the above assay methods, the cells are vertebrate cells which are not established cell lines but are primary neuronal cultures, which have been transfected or transformed to express mutant GABA receptors. In this embodiment, the action of potential GABA agonists and antagonists is observed.

In one embodiment of the present invention, differential toxicities of various pesticides may be evaluated with various cell types. In this embodiment, the action of pesticides on harmful insects is compared with the action on mammals. Microplates containing cells from the test animals (e.g., mosquitoes and livestock) are tested for their resistance/susceptibility to any number of pesticides in the screening assay described above.

In one preferred embodiment, the first screening assay format is used. Thus, if the mosquitoes are resistant to the action of the pesticide (e.g., it is not a GABA agonist), the mosquito cells will live because the toxin will be prevented from entering the cells. If the mosquitoes are susceptible to the action of the pesticide (e.g., it is a GABA agonist), the toxin will enter the cells and cause cell death. The same test methods are also performed on the vertebrate (e.g., livestock) cells. The results observed for the vertebrate cells are compared with those observed for the mosquito cells in order to determine whether the pesticide is effective against the insect pest to be killed and safe for use near livestock.

In another embodiment, the second screening assay format is used. In this assay, if the mosquitoes are resistant to the action of the pesticide (i.e., it is a GABA antagonist), the cells will live, as the toxin will be prevented from entering them. In contrast, if the mosquitoes are susceptible to the pesticide (i.e., it is not a GABA antagonist), the cells will die due to the entry of toxin. The same test procedures are then used on the vertebrate (e.g., livestock) cells. The results observed for the vertebrate cells are compared with those observed for the mosquito cells in order to determine whether the pesticide is effective against the insect pest to be killed and safe for use near cattle. The results observed for the vertebrate cells are compared with those observed for the mosquito cells in order to determine whether the pesticide is effective against the insect pest to be killed and safe for use near livestock.

In another embodiment, cells from two insect species, varieties or strains (e.g., insect pests are compared with beneficial insects) are tested to assess their comparative resistance and/or susceptibility to any number of pesticides in the screening assay described above.

In one embodiment, the first screening assay format is used. Thus, if the pests (e.g., mosquitoes) are resistant to the action of the pesticide (e.g., it is not a GABA agonist), the mosquito cells will live because the toxin will be prevented from entering the cells. If the mosquitoes are susceptible to the action of the pesticide (e.g., it is a GABA agonist), the toxin will enter the cells and cause cell death. The same test methods are conducted on the cells of the beneficial insect. The results observed for the beneficial insect cells are compared with those observed for the mosquito cells in order to determine whether the pesticide is effective against the insect pest to be killed and safe for in the presence of beneficial insects.

In another embodiment, the second screening assay format is used. In this assay, if the mosquitoes are resistant to the action of the pesticide (i.e., it is a GABA antagonist), the cells will live, as the toxin will be prevented from entering them. In contrast, if the mosquitoes are susceptible to the pesticide (i.e., it is not a GABA antagonist), the cells will die due to the entry of toxin. The test methods are also conducted on the beneficial insect (e.g., ladybug) cells. The results observed for the beneficial insect cells are then compared with those observed for the pest (e.g., mosquito) cells in order to determine whether the pesticide is effective against the insect pest to be killed and safe for use near the beneficial insects.

These embodiments may be used in any combination appropriate for the field situation involved. For example, the results for harmful and beneficial insects may be compared with those obtained for livestock which are maintained near the location of pesticide application. These methods are also contemplated to screen for resistance and/or susceptibility of wildlife to pesticides in order to avoid destruction of wildlife in adjacent habitats via pesticide drift, etc.

This invention contemplates the creation of resistance and susceptibility to pesticides. In one preferred embodiment, insertion of the gene encoding the normal GABA receptor (SEQ ID NO:2), renders the cell or animal susceptible to the action of pesticides which act as GABA agonists.

In another preferred embodiment, insertion of the gene encoding a mutant GABA receptor (SEQ ID NO:3, 5 or 7), renders the cell or animal resistant to the action of pesticides which act as GABA antagonists.

The present invention also contemplates the genotyping of various harmful and beneficial insects. For example, the identification by the present invention that the mutation which confers cyclodiene resistance is conserved between Drosophila, mosquitoes, and beetles has broad implications concerning the genetic basis of insecticide resistance and the potential use of the resistance gene as a selectable marker in genetic transformation in non-drosophilid insects. This is due to the semi-dominant nature of cyclodiene resistance which allows for ready selection of an inserted susceptible or resistant copy of the gene and thus makes it an ideal marker for genetic transformation.

This invention contemplates the use of PCR and allele-specific amplification to detect resistant and susceptible alleles in field and laboratory organisms. For example, two cyclodiene resistance alleles have been identified in *D. melanogaster* and *D. simulans* by PCR amplification of specific alleles (PASA). By placing the allele specific mutation at the 3' end of an oligonucleotide, poor amplification of other alleles, but specific amplification of the matching allele, can be achieved due to mismatch between the DNA template and the primer. This technique has several advantages over the monitoring technique which relies upon the detection of a restriction enzyme polymorphism caused by resistance associated mutations. It also distinguishes between the resistant alleles. The use of allele-specific oligonucleotides allows detection of specific resistance alleles, genotyping of individual insects, and is applicable to other resistance mechanisms associated with point mutations.

Under particular magnesium concentrations, PCR amplification of specific cyclodiene insecticide resistance alleles can be achieved using pairs of primers one of which carries the resistance associated single base substitutions at its 3' end. PASA has been used for the detection of single base pair mutations in a wide range of genes, but this is the first time is has been used to detect mutations associated with insecticide resistance.

This technique has a number of advantages over the detection of a resistance associated restriction enzyme polymorphism in PCR amplified DNA (PCR/REN), previously used to genotype Drosophila. Firstly, PASA allows for the detection of resistance associated nucleotide substitutions that are not associated with restriction enzyme polymorphisms. Secondly, PASA allows for the determination of the frequency of different resistance alleles whereas PCR/REN only establishes overall resistance gene frequency.

In order to guard against false negative results (i.e., failure of PCR reaction being classified as absence of allele) a second set of allele independent primers can be added to the reaction. Thus two products are now made, one allele specific and one allele independent. The presence of the allele independent product therefore serves as a negative control to ensure that DNA was added, and that successful amplification was performed by PCR. Further, when morphologically similar species are present field, the addition of a second primer set to the PASA reaction can therefore not only serve as an internal control against the failure of the reaction to amplify but also verifies that DNA from the correct species is being amplified. This overcomes the previous necessity, with some biochemical monitoring techniques, to simultaneously conduct a different assay in order to confirm species identity.

In some sibling species showing high levels of nucleotide conservation, like *D. melanogaster* and *D. simulans*, the allele independent primers (and in these species the allele dependent primer for allele 1) may work in both species. Thus, as *D. melanogaster* and *D. simulans* co-exist in the field, are difficult to easily separate morphologically, and both possess resistance, PASA is effective in measuring total allele frequencies in both species. In this situation, where species separation may require an additional PCR reaction or close morphological examination, measurement of combined resistance frequencies in both species may be the most suitable alternative. The possibility of allele independent primers working in other species commonly found together in field samples should thus be investigated on a case by case basis.

The major disadvantage of PASA over PCR/REN is that more than one reaction must be performed on an individual in order to obtain a genotype (i.e., SS, $R_1S$, $R_1R_1$ or $R_1R_2$ etc. where $R_1$ and $R_2$ represent different resistance alleles). Further, knowledge of all resistant alleles present is necessary in order to screen with the correct primers. In contrast with PCR/REN, genotypes can be distinguished by the number of products after a single restriction enzyme digest.

Successful resistance monitoring schemes must be able both to detect resistance and to follow the frequency of different resistance alleles as resistance increases. PASA can only be used for resistance alleles of known nucleotide sequence. PCR/REN can detect a number of different single base pair substitutions but provides little information about individual allele frequencies.

Thus, when a resistance associated enzyme polymorphism is available, as is present with cyclodiene resistance in Drosophila, both techniques should be used in combination. Thus, PCR/REN can be used to determine resistance frequency and PASA to identify the particular alleles involved. If the combined frequencies of the different resistance alleles detected by PASA do not equal the total frequency of resistance monitored by PCR/REN, then new resistance alleles must be present in the population which should be identified and sequenced in order to design new PASA primers.

EXPERIMENTAL

The following examples are provided in order to demonstrate and further illustrate certain aspects of the present invention. The susceptible Drosophila strains in the following examples may be obtained from the Department of Biology, Indiana University Bloomington, Ind. The examples are not to be construed as limiting the invention.

EXAMPLE 1

The present invention describes the cloning of an invertebrate GABA receptor, and thus provides the unique ability to manipulate the resistance status of an insect via genetic transformation. This example describes the isolation and sequencing of the normal Drosophila GABA receptor.

More specifically, FIG. 1 depicts the EcoR1 restriction map of the chromosomal walk through the polytene subregion of *D. melanogaster* which contains the cyclodiene resistance locus according to the invention. The extent of the overlapping cosmids in the walk are shown below the restriction map (in kb). The solid boxes represent the location of chromosomal breakpoints uncovering the resistant phenotype and sequences in the direction of the arrows extending from the boxes are deleted. Breakpoints without arrows correspond to inversions or insertions. The remaining breakpoints of these rearrangements lie outside the cloned region.

Figure 2:
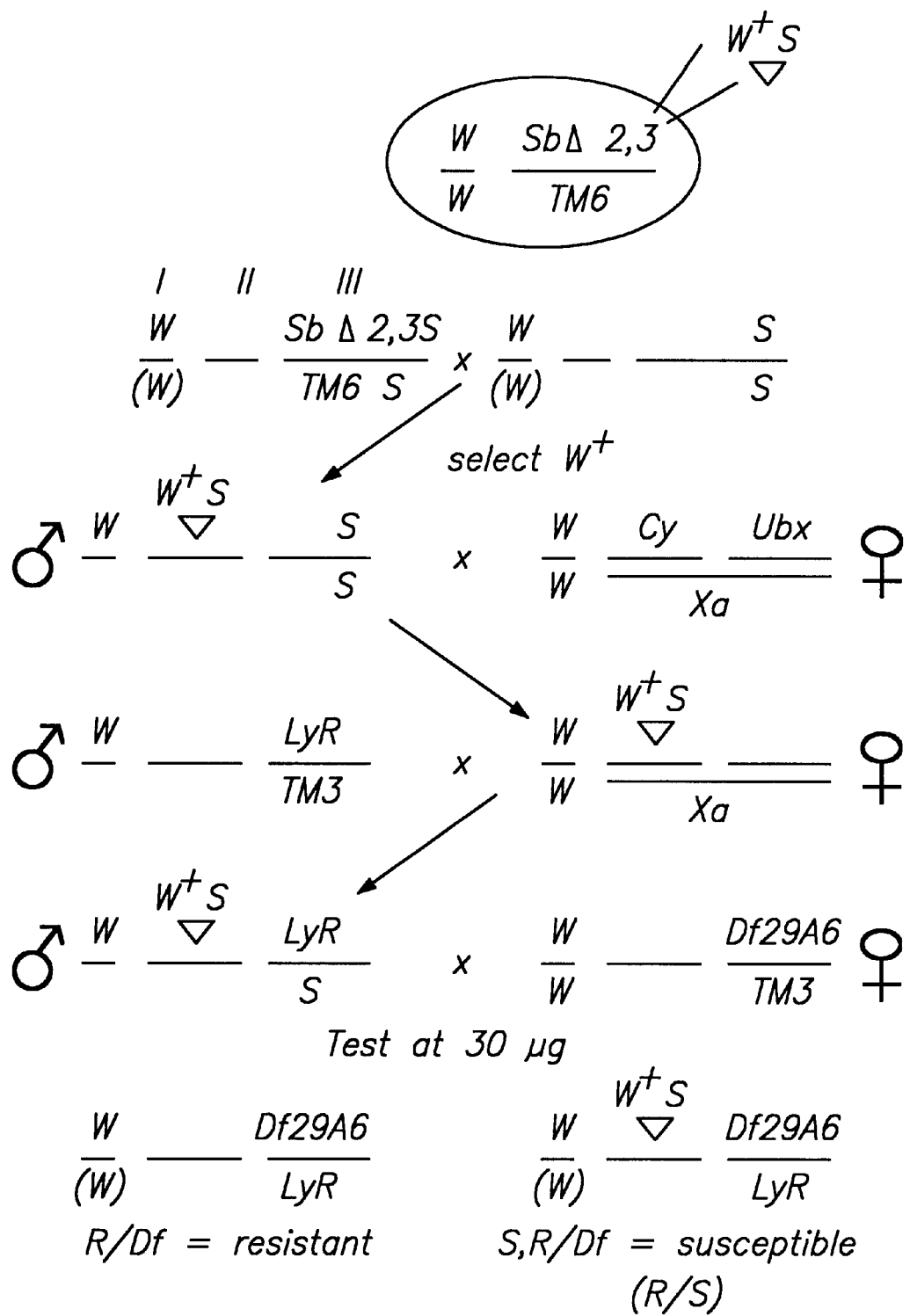
FIG. 2 depicts crosses used to rescue cyclodiene insecticide susceptibility.

More specifically, FIG. 2 depicts the crosses used to rescue cyclodiene insecticide susceptibility via P-element-mediated germline transformation. As depicted, embryos containing an endogenous source of transposase (Δ2,3) were injected with a cosmid carrying a susceptible copy of the gene and a copy of the mini-white eye color gene as a selectable marker. Successful $G_0$ transformants with red eyes ($w^+$) were subsequently crossed into flies hemizygous for resistance and a deficiency uncovering the resistance gene Df(3L)29A6. These flies carrying the $w^+S$ insert (transferred DNA) are susceptible to a dose of 30 μg dieldrin, whereas their siblings without the insert are resistant to this dose.

In order to more precisely localize the gene within the 200 kb of DNA isolated from the 66F subregion, new chromosomal rearrangements were induced using γ irradiation and screened for those uncovering the resistance gene. Chromosomal rearrangements were generated by exposing male SS flies with multiply marked third chromosomes (*rucuca* strain) to 4,000 rads of radiation in a γ radiation (cesium)

source, and then outcrossing these R/R (Rdl$^R$/Rdl$^R$) females. New rearrangements uncovering resistance were screened for by exposing their progeny at a dose of 30 μg dieldrin, at which only R/Df (Rdl$^R$/Df) flies will survive (all the expected RS progeny will die at this dose level except for any R/– flies wherein "–" is any new rearrangement uncovering the resistance gene), survivors were crossed to In(3LR) TM3/Sb and maintained as a balanced stock (Df/In(3LR) TM3).

Approximately 50,000 flies were screened. For screening, 20 ml glass scintillation vials were coated internally with 30 μg of dieldrin in acetone and rolled until dry. Twenty to thirty flies per vial were added and mortality was recorded after 24 hours at 25° C..

Procedures for the purification of DNA from phage, plasmids or cosmids, the transfer of nucleic acids to Zetabind filters (CUNO Life Sciences, Meriden, Conn.) and the hybridization of primer extended probes to filter blots were based upon well established techniques. See Sambrook et al., eds., *Molecular Cloning*, 2d ed., (Cold Spring Harbor Laboratory, 1989). Genomic DNA from rearrangement stocks was purified from approximately 100 adult Drosophila and the DNA was then transferred to filters by vacuum blotting for 1 hour. Cosmids were isolated from a library constructed of DNA from susceptible flies (strain iso-1) in a modified CosPer vector. DNA was cut with SauIIIA, size selected (30–45 kb inserts of genomic DNA) and cloned into the BamH1 site of the polylinker. The presence of Not1 sites flanking the cloning site, a rare restriction site in Drosophila, allows for easy insert isolation. The absence of Xba1, Hpa1 and EcoR1 sites in the vector facilitates the identification of cosmid and fragments for chromosomal walking. Bender et al., J. Mol. Biol., 168:17 (1983).

In situ hybridization of cosmid DNA labeled with biotinylated dUTP to salivary gland polytene chromosomes from the strain CantonS was performed. Roberts, (ed.), *Drosophila: A Practical Approach*, (IRL Press, Ltd., Oxford, 1986). Salivary glands were dissected from Drosophila larvae, squashed on glass slides, denatured with sodium hydroxide, and dehydrated with ethanol. Biotinylated cosmid DNA was then added, allowed to hybridize with the DNA of the chromosome overnight, washed with a solution of phosphate buffered saline and detergent (Tween), and treated with horseradish peroxidase to detect specific staining as a brown mark.

The cDNA's were isolated from a library made from RNA from 12–24 hour old embryos. Restriction fragments of the candidate cDNA isolates were subcloned into Bluescript (Stratagene, La Jolla, Calif.) and sequenced as a double stranded template using well known protocols. Sanger et. al., Proc. Natl. Acad. Sci. USA 74:5463 (1977).

P element mediated germline transformation was conducted using DNA from cosmid 6, purified by spermine precipitation and at a concentration of 1 μg/μl. The DNA was injected into 600 embryos of a w,Δ2,3Sb/TM6 strain, where Δ2,3 supplies an endogenous source of transposase (Robertson et al. Genetics 118:461, 1988). Of 50 fertile G$_0$ flies mated to a P-element free white eyed strain w$^{1118}$, one yielded progeny with red eye color (w$^+$) conferred by expression of the mini-white gene of the cosmid.

Using the breakpoints generated, that were known to break in or near the resistance gene, the gene was cloned via a chromosomal walk through the 66F subregion, and then by localizing the gene within the walk by using chromosomal rearrangement breakpoints which uncovered the resistant gene. The walk was initiated from a phage clone, λ121, derived from a Maniatis library. This clone, in situ, hybridized to polytene chromosome bands 66F1,2 and was thus used to screen the cosmid library as an initiation point for the walk. The initial direction of the walk was established by in situ hybridization back to polytene chromosomes and subsequent steps were isolated as described above. A map of the complete walk is given in FIG. 1.

The single breakpoint positions of four rearrangements (FIG. 1) were located within the walk by probing whole genomic Southern blots of the rearrangement strains with gel purified fragments from cosmid steps of the walk. When a probe is used that spans a rearrangement breakpoint, it was observed that either one or two novel bands with respect to the parent strain appeared. One novel band indicates a deficiency breakpoint, whereas two novel bands indicate either an insertion or an inversion of a stretch of chromosome. Restriction fragments were electrophoresed on low melting temperature agarose (Sea-plaque®, FMC BioProducts, Rockland, Me.) and then excised from the gel. DNA was labeled with $^{32}$P by primer extension with a multi-prime kit (Amersham, Arlington Heights, Ill.).

The cytology of these four new rearrangements was also examined. Three of these rearrangements breakpoints were within cosmid 6 and gave two new recombinant bands on a genomic Southern blot, indicating that either they were inversions or insertions. The cytology of the first revealed it to be a simple inversion, In(3L) Rdl-11, with breakpoints at 63E-F and 66F. The second, Rdl-20, is a complex rearrangement with one breakpoint within 66F and at least three others outside the subregion. The third, Rdl-1, is not cytologically visible. The remaining fourth rearrangement, Df(3L)Rdl-2, shows only one recombinant band on a Southern within cosmid 2 and is cytologically apparent as a small deletion of only one darkly staining polytene band 66F5 within the subregion.

Both of the cytologically visible rearrangements, In(3L) Rdl-11 and Rdl-20, have only one breakpoint within 66F and others at independent locations outside the region. Their breakpoints within cosmid 6 must, therefore, mark the location of the gene.

As both of the cytologically visible rearrangements giving two new recombinant bands on a Southern with probes from cosmid 6 have only one breakpoint within 66F, this cluster of breakpoints which disrupts the gene must therefore mark its location. In order to determine whether cosmid 6 contained a functional copy of the gene for cyclodiene resistance, P-element germline transformation with this cosmid was carried out. Following successful isolation of a w$^+$ transformant, linkage to the insert to the second chromosome was established after crossing male G$_0$ progeny to a stock bearing markers on the second and third chromosomes (FIG. 2). Since the cosmid library was made from a susceptible strain, the w$^+$Rdl$^S$ insert was crossed into flies hemizygous for resistance and carrying the original deficiency Df(3L)29A6 uncovering sequence. Those flies carrying the insert were effectively restored to an Rdl$^R$/Rdl$^S$ genotype and were susceptible to a dose of 30 μg dieldrin (93% mortality, n=221, corresponding to an expected Rdl$^R$/Rdl$^S$ mortality of 100%). In contrast, their siblings without the insert were resistant (7% mortality, n=214, corresponding to the expected Rdl$^R$/Df(3L)29A6 mortality of 15%).

In order to isolate and sequence the GABA cDNA, the 10 kb EcoR1 restriction fragment from cosmid 6, which spans two (R1 and R20) of the three clustered rearrangement breakpoints, was used to screen a cDNA library maintained in *E. coli* made from RNA collected from 0–12 and 12–24 hour embryos. *E. coli* were plated at a density of approximately 3000 per 14 cm diameter agar plate. Colonies were transferred to nylon filters and screened with the $^{32}$P-labelled 10 kb EcoR1 fragment as a probe. Positive clones were isolated by further re-screening. DNA was prepared and the inserts restriction mapped (i.e., fragments were aligned by size after cutting with restriction enzymes and electrophoresis). From fourteen independently isolated cDNA clones which hybridize to this fragment, one was isolated, NB14.1, which spanned all three rearrangement breakpoints, as shown by probing blots of restriction digests of candidate cDNA's with gel purified cosmid restriction fragments corresponding to the locations of the breakpoints. Restriction fragments from this cDNA were subcloned into the vector Bluescript (Stratagene, La Jolla, Calif.) and sequenced by double stranded sequencing using Sequenase enzyme (U.S. Biochemicals, Cleveland, Ohio). Primers from the T3 and T7 promoters of the vector were used to initiate sequencing and any gaps in the sequence thus generated were bridged by primers synthesized from the novel sequence. This cDNA is shown in SEQ ID NO:2. Without the upstream primer, the cDNA sequence of SEQ ID NO:9 begins at base no. 91 (i.e., at codon ATG).

The invention also encompasses fragments of the above sequence which have substantially the same biological reactivity and function as the whole sequence.

Sequence analysis of this cDNA reveals one long open reading frame (ORF) of 606 amino acids. The ORF has three closely spaced methionine residues at its amino terminus (corresponding to compatible nucleotides 91, 106, and 124 in the above sequence), two of which closely match the consensus for translation start sites in Drosophila. In the absence of more conclusive experimental data, it is believed that the first of these methionines is the putative translation start. The sequence of this ORF (depicted in the following amino acid sequence) was used to scan databases of DNA and protein sequences, revealing highest homology to several vertebrate GABA receptor subunits.

When aligned with the polypeptide sequences of three bovine and rat GABA receptor beta subunits (Ymer et al., EMBO J., 8:1665 (1989)), the Drosophila sequence shares a minimum of 26% identity with all of the other six receptor subunits. It also shows conservation of a cystine bridge (a pair of cysteine residues some 13 amino acids apart) and four transmembrane regions which are conserved motifs shared by all the members of the gene superfamily to which GABA receptors belong. Olsen and Tobin, supra.

Figure 3:
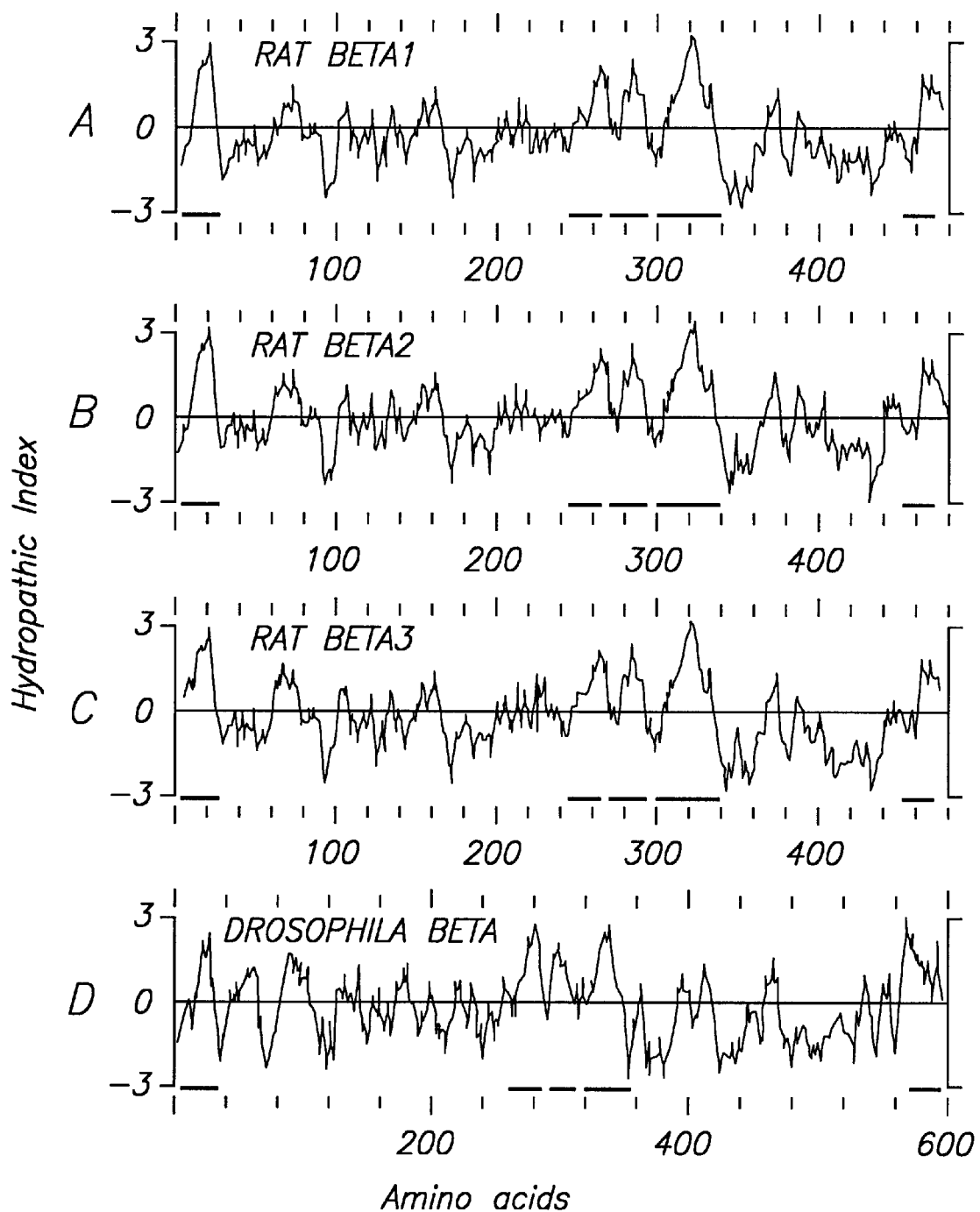
FIG. 3 depicts a comparison of the hydropathy profiles between rat and insect amino acid sequences.

A further indication that the cDNA NB14.1 encodes a GABA receptor is obtained by comparison of the hydropathy profiles shown in FIG. 3. As indicated, the four hydrophobic domains presumed to span the membrane are present in homologous positions within the insect sequence, and also, a hydrophobic region has been maintained at the amino terminus in the Drosophila sequence, matching the presumed signal sequence from vertebrate clones. Schofield et al., Nature 328:221 (1987).

In order to confirm that a copy of the insecticide resistance gene had been cloned, resistant flies were transformed to susceptibility using the cloned copy of the susceptible gene contained in cosmid 6 (FIG. 2). The cosmid vector contains a copy of the mini white gene which encodes for red eye color and P-element repetitive ends to allow for reintroduction into the genome. As R/– (where "–" is any rearrangement uncovering resistance) can survive a dose of 30 µg of dieldrin and R/S flies cannot, it was postulated that introducing a cloned copy of S (cosmid 6) back into R/– flies would cause an effectively R/–;S genotype which would behave as R/S, and the flies would die at this dose, provided that cosmid 6 contains a functional copy of the susceptible gene.

Cesium chloride banded DNA from cosmid 6 was spermine precipitated and then injected into dechorionated embryos at a concentration of 1 µg/µl. Adults collected after maturation of surviving embryos were crossed to a standard white eyed strain, w$^{1118}$, and their progeny searched for w$^+$ (red eyed) flies, an indication that the flies contained a successful incorporation and expression of the gene in the germ line. An insertion of cosmid 6 on chromosome II was obtained and the insert was then crossed into R/– flies where "–" was the original deficiency uncovering resistance Df(3L)29A6. These flies died at 30 µg dieldrin (93% mortality out of 221 flies), whereas their siblings without cosmid 6 were resistant (7% mortality out of 214 flies).

Thus, this experiment shows definite proof that cosmid 6 contains a functional copy of the gene conferring susceptibility to cyclodiene insecticides, and also shows the successful expression of a cloned copy of this gene in living flies.

EXAMPLE 2

This invention contemplates both the identification and creation of nucleic acid and amino acid changes responsible for the expression of resistance. This example describes the nucleic acid and amino acid changes responsible for the expression of resistance in Drosophila.

Various Drosophila strains were used in this example. Table 1 indicates the geographic sources of *D. melanogaster* and *D. simulans* resistant and susceptible to cyclodiene insecticides and percentage of *D. melanogaster* strains possessing an EcoRI restriction site near the resistance-associated mutation (this ECoRI site is absent in susceptible and resistant *D. simulans*).

Strains showing resistance were made homozygous after two to four generations of selection until all flies could survive a dose of 30 µg of dieldrin, which kills all RS and SS genotypes and allows 85% survival of RR flies. ffrench-Constant et al., Econ. Entomol., 83:1733, (1990). Strains were assumed to be homozygous for resistance only when bioassays showed not more than 15% mortality at 30 µg dieldrin. In several cases, isofemale susceptible strains were also established from the same areas. These field-collected and isofemale strains were used in the initial identification of the resistance-associated mutation, but studies of linkage to other restriction-site markers in *D. melanogaster* were done with isochromsomal lines to ensure that only a single chromosome was being analyzed.

Isochromosomal lines of *D. melanogaster* (for both resistance and suceptibility) were initiated by crossing males from the candidate strains with Df(3L)29A6 Sb$^+$/Tm3 Sb females. Sb$^+$ males and female offspring were collected as virgins and mated inter se. Their offspring were tested with 30 µg dieldrin to assure that they were resistant to 1 µg to assure that they were suspectable as appropriate.

TABLE 1

| Origin of strain | Resistant lines no. | Resistant lines EcoRI, % | Susceptible lines no. | Susceptible lines EcoRI, % |
|---|---|---|---|---|
| *D. melanogaster* | | | | |
| Laboratory (Oregon-R, Canton-S, Iso-1) | 0 | | 3 | 0 |
| North America | 27 | 93 | 16 | 16 |
| Maryland, USA (3 sites) | 8 | 88 | 3 | 17 |
| New York, USA (2 sites) | 3 | 83 | 0 | |
| Ontario, Canada | 1 | 100 | 0 | |
| Florida, USA | 11 | 95 | 6 | 0 |
| California, USA (3 sites) | 4 | 100 | 7 | 21 |
| South America (Guyana) | 4 | 100 | 3 | 17 |
| Hawaii | 0 | | 8 | 38 |
| Australia | | | | |
| New South Wales (2 sites) | 2 | 100 | 4 | 38 |
| Africa | 15 | 100 | 16 | 56 |
| Kenya (5 sites) | 7 | 100 | 8 | 50 |
| Mali | 8 | 100 | 7 | 71 |
| Brazzaville | 0 | | 1 | 50 |
| Europe | 0 | | 33 | 12 |
| France (2 sites) | 0 | | 25 | 16 |
| Poland | 0 | | 8 | 0 |
| *D. simulans* | | | | |
| North America | | | | |
| Maryland, USA | 0 | | 1 | |
| California, USA (7 sites) | 8 | | 16 | |
| Mexico | 0 | | 1 | |
| Panama | 0 | | 1 | |
| South America | | | | |
| (Columbia, 2 sites) | 0 | | 2 | |
| Hawaii | 0 | | 1 | |
| Australia (Melbourne) | 0 | | 1 | |
| Asia (Japan) | 1 | | 5 | |
| Africa (Kenya, 11 sites) | 1 | | 10 | |
| Europe (France) | 0 | | 1 | |

The laboratory strains Oregon-R, Canton-S, In(2LR)CyO/Inv(2LR)Gla and white$^{1118}$ were used as susceptible standards. The susceptible strain Iso-1 (isogenic for all three chromosomes) is the strain from which the genomic DNA encompassing the resistance gene was initially isolated.

The nucleotide sequence of the complete open reading frame of the resistant Rld$^{MD-RR}$ allele was determined by direct PCR-based sequencing of the RNA (RNA/PCR). RNA/PCR was done by using PCR primers derived from the susceptible allele (SEQ ID NO:10 AND SEQ ID NO:11). Rdl sequences were amplified from cDNA made from the total RNA of 12- to 24-hour old Rdl$^{MD-RR}$ Drosophila embryos. For cDNA synthesis, approximately 20 μg of RNA was added to a 50 μl reaction containing 1000 units of reverse transcriptase, 5 units of RNAsin, 10 μM random primers, 0.2 mM dNTPs, and 1 mM dithiothreitol in reverse transcriptase buffer (Bethesda Research Laboratories, Gaithersburg, Md.). For PCR, approximately 600 ng of cDNA was added to a 50 μl reaction containing 0.2 μM of each primer, 5 mM dNTPs, 2.5 mM MgCl$_2$ and 0.25 units of Taq polymerase. Amplification was done for 40 cycles. Each cycle was comprised of denaturation for 1 minute at 94° C., annealing for 1 minute at 55° C., and extension for 2 minutes at 72° C. Products were sequenced directly by using Taq polymerase (Promega, Madison, Wis.).

Figure 4:
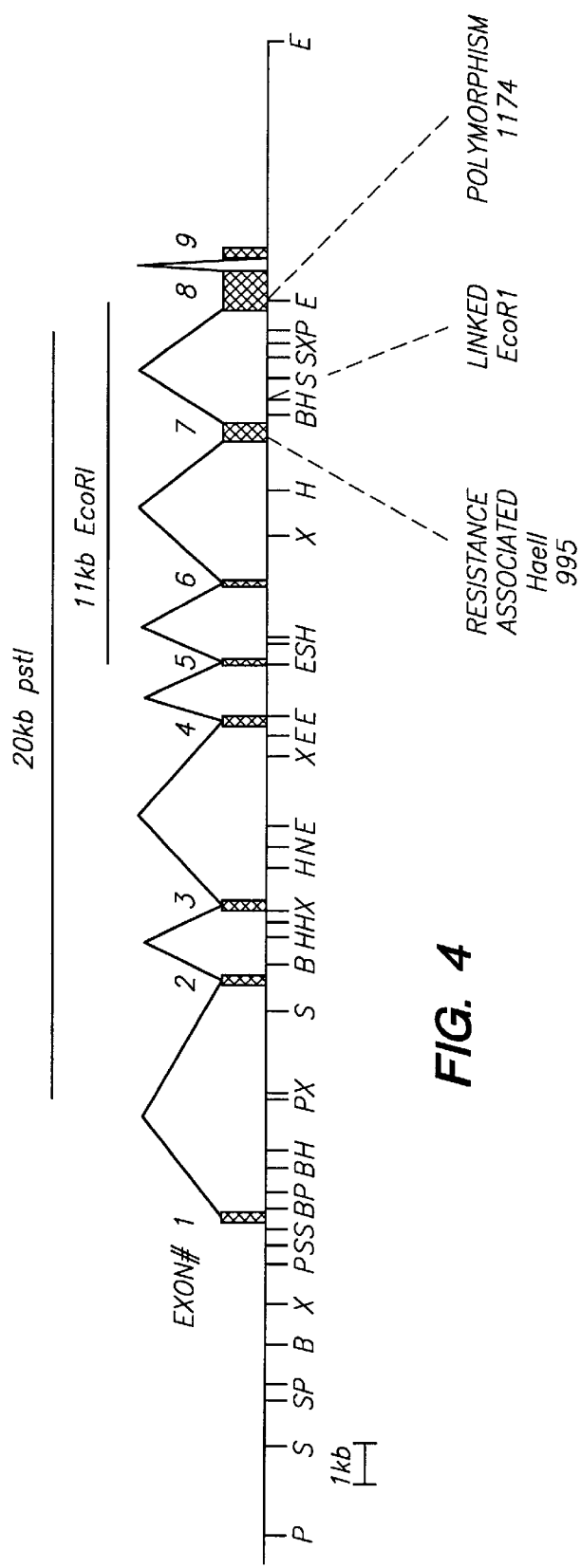
FIG. 4 shows the location of the HaeII restriction enzyme site associated with cyclodiene insecticide resistance in the Rdl locus, a linked EcoR1 site, and an unrelated polymorphism.

Genomic DNA corresponding to most of the resistance locus of the GABA$_A$ receptor gene was cloned from strain Rdl$^{MD-RR}$ in a 20-kb Pst I fragment (see FIG. 4). This figure shows the location of the Hae II restriction site associated with cyclodiene insecticide resistance in the Rdl locus, a linked EcoRI site, and an unrelated polymorphism (numbers refer to nucleotide positions in the cDNA). Positions of exons in Rdl cDNA are shown a restriction map of genomic DNA. Restriction fragments are referred to as: E, EcoRI; S, Sac I; B, BamHI; X, Xho I; H, HindIII; P, Pst I; and N, Not I.

Genomic DNA was prepared from the resistant strain and banded on a cesium chloride gradient. Sambrook et al., supra. DNA was digested to completion with Pst I and size-fractionated on a sodium chloride gradient; the 20-kb fraction was cloned into Pst I-cut Bluescript (Stratagene, La Jolla, Calif.) as a subgenomic library. A clone corresponding to most of the Rdl locus was isolated by screening this library with a radiolabeled 11-kb EcoRI restriction fragment from the susceptible allele (FIG. 4). DNA for Southern blotting or restriction endonuclease (REN)/PCR was prepared from either 50 flies or one individual by standard procedures. Sambrook et al., supra.

For REN/PCR, approximately 50 ng of genomic DNA was added to a 50 μl reaction containing 0.2 mM dNTPs, and 0.25 units of Taq polymerase. PCR was performed for 35 cycles with 1-minute denaturation at 94° C., 1-minute annealing at 50° C., and 1-minute extension at 72° C. PCR products were cleaned by a single phenol/chloroform extraction before digestion with restriction enzymes.

Two single base-pair differences were detected in the Rdl$^{MD-RR}$ allele of *D. melanogaster* compared with susceptible cDNA NB14.1. Both changes result in an amino acid replacement of Ala to Ser in exon 7 (G to T at nt 995) and Met to Ile in exon 8 (G to A at nt 1174)(SEQ ID NO:5 AND SEQ ID NO:6). To confirm that these were not artifacts from PCR, the corresponding regions of genomic DNA from the resistant Rdl$^{MD-RR}$ strain were also sequenced. Of these two amino acid substitutions detected in Rdl$^{MD-RR}$, only the Ala-to Ser mutation is directly correlated with resistance, as Met to Ile is sometimes absent in resistant species.

Figure 5:
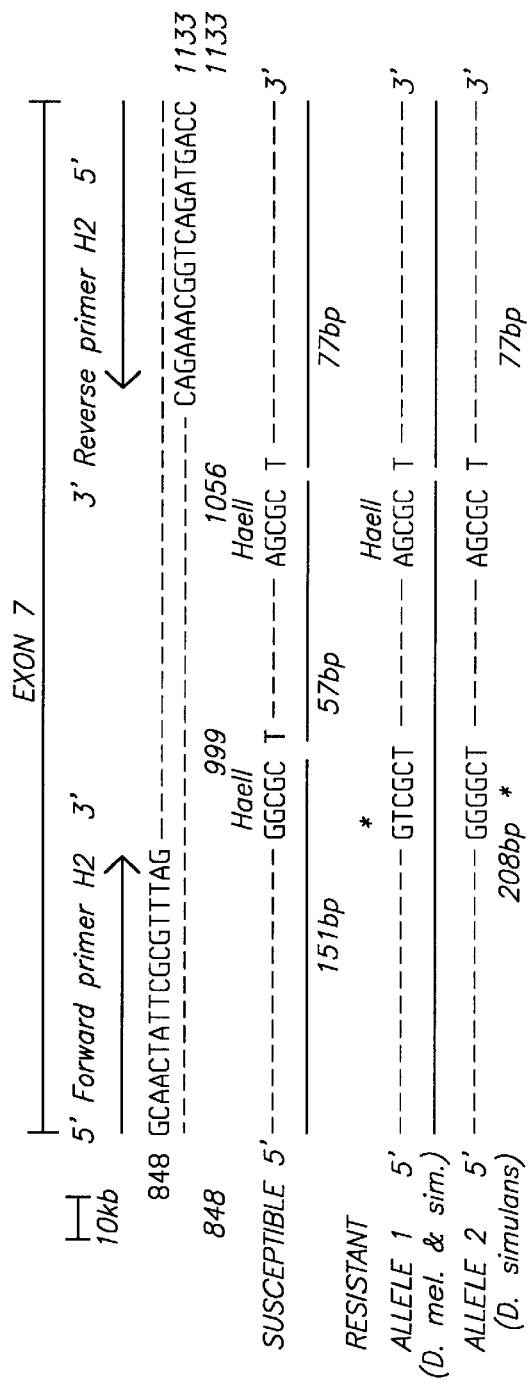
FIG. 5 shows the location and sequence of the resistance-associated HaeII site within exon 7 of the $GABA_A$ receptor cDNA in susceptible and two cyclodiene insecticide resistant alleles of Drosophila.

This region of the Rdl gene was also sequenced from a number of resistant *D. simulans* strains. Although some possessed the same nucleotide substitution as *D. melanogaster,* others showed a different substitution within the same codon, a C to G at nt 996 (alleles 1 and 2, respectively in FIG. 5)(SEQ ID NO:7 and SEQ ID NO:8). In this second allele, glycine, instead of serine, substitutes for alanine (Ala to Gly) in exon 7.

The single base pair substitutions at position 995 or 996 in exon 7 both result in the loss of a Hae II restriction site in the resistant allele. Therefore, the loss of this restriction enzyme site serves as a marker of the resistance phenotype.

Figure 6:
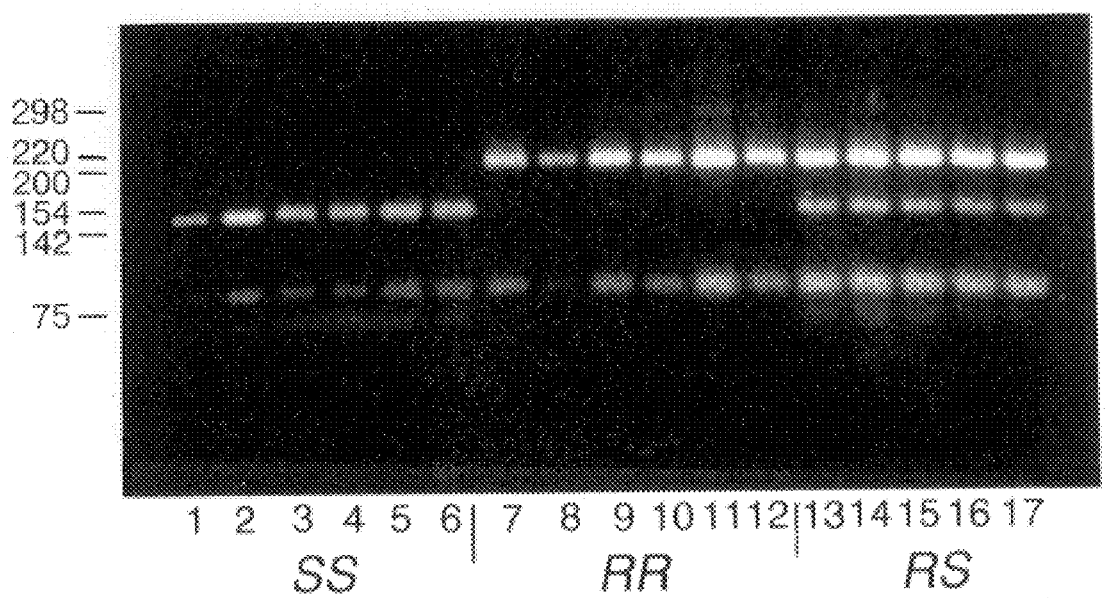
FIG. 6 shows the PCR products from exon 7 of the Rdl gene digested with HaeII.

Loss of the Hae II site can also result from a variety of other silent substitutions and, in addition, detect as-yet-undiscovered susceptible alleles. When a PCR product encompassing exon 7 is digested with Hae II, SS strains should yield three products (151, 77, and 57 bp), but RR strains yield only two products (208 and 77 bp) as shown in FIG. 6. This figure shows the location and sequence of the resistance-associated Hae II site within exon 7 of the GABA$_A$ receptor cDNA in susceptible and two cyclodiene insecticide-resistant alleles of Drosophila. Allele 1 is found in both *D. melanogaster* (mel) and *D. simulans* (sim), and allele 2 is found in *D. simulans* only. An asterisk indicates the two alternative single-nucleotide substitutions in the resistant alleles that destroy one of the two Hae II sites found in exon 7 of the susceptible sequence. Also indicated are the PCR primers used (SEQ ID NO:10 AND SEQ ID NO:11)

and the sizes of the Hae II restriction enzyme products in susceptible and resistant flies.

PCR/REN products (using the primers shown in FIG. 5) cut with Hae II from a number of SS, RR, and heterogeneous strains confirmed this prediction; SS strains yielded three products, RR strains yield only two products; and the segregating lines show all four products (FIG. 6). This figure shows the PCR products (the sizes of the products are labeled in bp) from exon 7 of the Rdl gene digested with Hae II. Drosophila are homozygous susceptible SS (lanes 1–6), homozygous resistant RR (lanes 7–12), and heterozygous RS (lanes 13–17) for cyclodiene insecticide resistance. Results were identical to those shown for the 58 RR and the 122 SS strains of *D. melanogaster* and *D. simulans* described in Table 1. *D. melanogaster* strains used were homozygous susceptible (SS) (Lanes: 1, OregonR; 2, CantonS; 3, Iso-1; 4, white$^{1118}$; 5, CyO/Gla) homozygous resistant (RR)(lanes: 7, Easton, Md.; 8, Rochester, N.Y., 1988; 9, Vineland, Ontario, Canada; 10, Rochester, N.Y., 1990; 11, Newfield, N.Y.), and heterozygous (RS) from an Fl cross of RR stocks in lanes 7–11 with OregonR (SS) (lanes 13–17 in respective order). *D. simulans* strains used were homozygous susceptible (SS); Riverside, Calif. (lane 6) and homozygous resistant (RR), Davis, Calif. (lane 12).

Blind testing of 48 RR and 83 SS lines of *D. melanogaster* by both PCR/REN and insecticide bioassay revealed that this restriction enzyme site was invariably lost in resistant strains but was present in all susceptible lines. The only ambiguities observed related to the detection of heterozygotes by the DNA diagnostic within strains not completely selected to homozygosity by insecticide selection; these cases were reconfirmed by insecticide bioassay. Loss of the Hae II site was also directly associated with resistance in the closely related species *D. simulans,* being absent from all 10 RR and present in all 39 SS lines examined.

Figure 7:
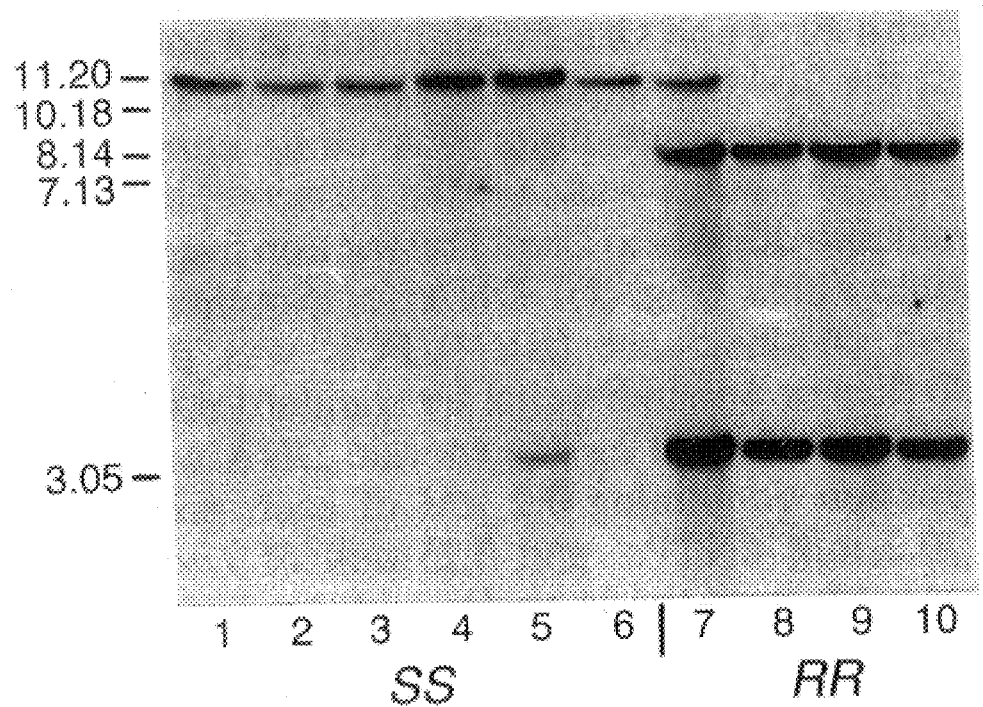
FIG. 7 is an autoradiograph of a Southern blot of genomic D. melanogaster strains which are homozygous susceptible and homozygous resistant for cyclodiene insecticide resistance.

A restriction enzyme polymorphism closely linked to resistance was initially detected during Southern blotting of a number of resistant and susceptible strains. When the small number of strains first examined from North America were probed with an 11-kb Eco RI fragment (FIG. 4) from the locus, SS flies yielded an 11-kb fragment (lanes 1–4, and 6; lanes: 1, Riverside, Calif.; 2, Davis, Calif.; 3, CantonS; 4, OregonR; 6, Newfiled no. 2 NY), but RR strains showed a 3.1- and an 8-kb fragment (lanes 8–10; lanes: 8, Easton, Md.; 9, Rochester, N.Y.; 10, Vineland, Ontario, Canada) due to a novel Eco RI site. Strains segregating for resistance and susceptibility showed all three fragments of 11, 8 and 3.1 kb (FIG. 7, lanes 5 [Newfield no. 1] and 7 [Newfield no. 30]). Sizes of the restriction fragments are shown in kb.

Figure 8:
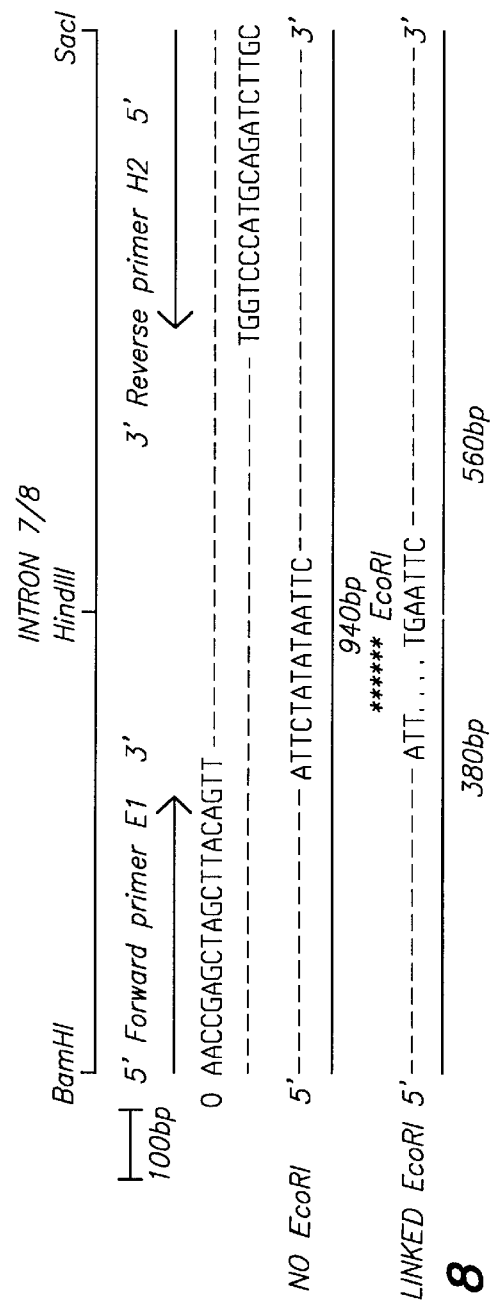
FIG. 8 shows the location and sequence of a polymorphic EcoR1 restriction site closely linked with resistance and the PCR primers used in its location within intron 7/8 of the Rdl gene.

The polymorphism was located in a neighboring intron (between exons 7 and 8) by restriction mapping, only approximately 700 bp from the resistance-associated mutation in the genomic DNA (FIG. 4). The nucleotide sequence encompassing this polymorphism was determined by sequencing genomic DNA from the susceptible (Iso-1) and resistant Rdl$^{MD-RR}$) strains (FIG. 8). This figure shows the location and sequence of a polymorphic EcoRI restriction site closely linked with resistance and of the PCR primers used in its location, within intron ⅞ of the Rdl gene. Nucleotides absent or substituted to create the novel EcoRI site in the resistant flies are indicated by an asterisk.

Figure 9:
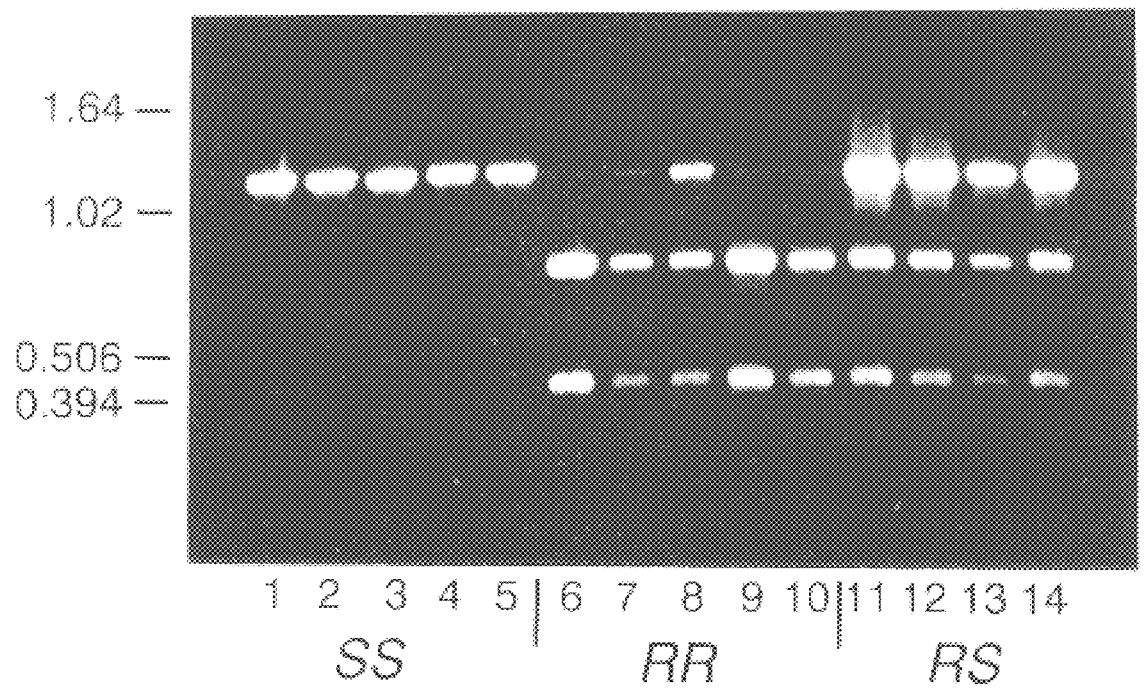
FIG. 9 shows the PCR products from intron 7/8 of the Rdl gene, digested with EcoR1 for homozygous susceptible and homozygous resistant, and heterogeneous D. melanogaster strains.

The actual distance of the EcoRI site from the resistance-associated mutation based on sequencing data was 770 bp. To detect this polymorphism by PCR/REN, primers flanking the region were made (FIG. 8; SEQ ID NO:12 and SEQ ID NO:13). When the PCR/REN products from this region were cut with EcoRI, SS strains homozygous for the absence of the novel EcoRI site yield only a single (940 bp) product, RR strains homozygous for its presence yield two fragments (560 and 380 bp), and heterozygous strains segregating for both alleles show all three products (940, 560, and 380 bp) (FIG. 9). This figure shows the PCR products from amplification of intron ⅞ of the Rdl gene, digested with EcoRI for homozygous susceptible (SS), homozygous resistant (RR), and heterogeneous (RS) *D. melanogaster.* Resistant flies without the EcoRI site as illustrated by lane 8, which is RR, but heterozygous for the EcoRI site, were found in only three of the 48 RR strains examined. The size of the products are labelled in bp. *D. melanogaster* strains used were homozygous susceptible (SS) (lanes: 1, OregonR; 2, CantonS; 3, Iso-1; 4, white$^{1118}$; 5 CyO/Gla), homozygous resistant (RR)(lanes: 6, Easton, Md.; 7, Vineland, Ontario, Canada; 8, Newfield, N.Y.; 9, Rochester, N.Y. 1990; 10, Rochester, N.Y. 1988), and heterogeneous (RS) from an F1 cross of RR stocks in lanes 6–9 with OregonR (SS) (lanes 11–14, in respective order).

The frequency of the EcoRI site in the SS lines ranged from 12–56% when averaged by continent (Table 1). In contrast, the EcoRI site was almost always present in RR lines. Of the 48 RR lines of *D. melanogaster* examined, only two isofemale lines (Queenstown 3, Md. and Apopka 6, Fla.) were homozygous for lack of the site, and one strain (Newfield, N.Y.) was heterogenous.

EXAMPLE 3

The cloning of cDNA's from the GABA$_A$ locus allows for functional expression of mRNA derived from this and other subunit cDNA templates in various cell types. This example describes expression of normal and mutated GABA receptors in the Xenopus oocyte expression system.

In the Xenopus oocyte expression system, oocytes removed from ovaries of adult Xenopus are arrested at the first meiotic prophase. Because each oocyte is fairly large and has a large nucleus, it is technically easy to inject foreign DNA into the oocyte nucleus. Typically, 20–40 nl is injected through a finely drawn glass capillary. The endogenous Xenopus RNA polymerases transcribe this injected exogenous DNA. Mertz and Gurdon, Proc. Natl. Acad. Sci. USA 74:1502 (1977). The exogenous DNA is assembled into chromatin, but there is no replication of injected duplex DNA in the oocyte. Gargilo and Worcel, J. Mol. Biol., 170:699 (1983); Ryoji and Worcel, Cell 37:21 (1984). Single-stranded DNA (e.g., DNA obtained by cloning in M13 vectors), is converted to duplex form within the oocyte nucleus. The Xenopus oocyte also efficiently translates mRNA injected into its cytoplasm.

The large size of the oocytes makes it relatively easy to insert electrodes into the oocytes in order to measure the electrophysiological responses (i.e., patch clamp electrophysiology) to neurotransmitters (e.g., GABA) and related substances. Various studies have shown that this Xenopus expression system is feasible for expression of foreign DNA. Kreig and Melton, EMBO J 4:3464 (1985); Masu et al., Nature 329:836 (1987); Wilson et al., Cell 47:589 (1986); see also, Old and Primrose, *Principles of Gene Manipulation,* 4th ed. (Blackwell Scientific Publications, Oxford, 1989)(pp. 296–302).

In the system of the present invention, messenger RNA produced from cDNA template, (both messenger RNA and cDNA template are considered to be part of the present invention), is injected into Xenopus eggs which then express the protein. By patch clamp electrophysiology experiments, one can then determine whether the cell is expressing the protein (measured by electrical impulses) and whether this expression can be altered by the compound of interest.

Injection of relatively high concentrations of wild-type (Rdl$_s$) mRNA alone (>50 n/oocyte), synthesized in vitro from cDNA 14.1, resulted in the appearance of GABA-evoked currents with a reversal potential of −20 to −25 mv (similar to that previously described for chloride channels). The GABA response was dose-dependent, with a threshold varying from 0.5 to 100 $\mu$M GABA, and maximum current ranging from 50 nA to >5 $\mu$A (oocytes were voltage clamped at −60 mV with a 2-electrode amplifier). Similar currents were elicited by the GABA$_A$ agonist muscimol.

Currents were recorded in 96 mM NaCl, 2 mM Kcl, 1.8 mM MgCl$_2$, and 5 mM Hepes. Recordings were made 1–5 days after injection. PTX, GABA, muscimol hydrobromide and (−)-bicuculline methiodide were dissolved in saline. Dieldrin was dissolved in DMSO (dimethylsulfoxide), then diluted to a final concentration of 0.1% DMSO. The single base pair substitution of GCG (alanine) to TCG (serine) was introduced into the sensitive cDNA 14.1 by subcloning in a restriction fragment from the insensitive cDNA. The region containing the mutation was then amplified by PCR from total embryonic RNA from Rdl$^{R-MD}$ flies and subsequently digested with EcoRV and Acc1. This restriction fragment was then cloned into the sensitive cDNA 14.1 cut with the same enzymes to yield the Ala to Ser mutant construct. The presence of the mutation was confirmed by sequencing.

FIG. 10 shows the currents recorded under voltage clamp conditions (−60 mv) from oocytes injected with (a, b, c) wild-type 14.1 cDNA, and (d, e) Ala to Ser mutant. FIG. 10(a) shows the responses of a single oocyte to GABA (10 $\mu$M), muscimol (10 $\mu$M) and bicuculline (100 $\mu$M, with 10 $\mu$M GABA). In FIGS. 10(b–e), the left column shows currents measured in response to 50 $\mu$M GABA (the approximate EC$_{50}$; concentration required to elicit 50% of the GABA response) and the right column shows the effect on these currents of 1 $\mu$M PTX or 10 $\mu$M dieldrin.

In order to test the effect of the resistance-associated Ala to Ser mutation, this substitution was introduced into the sensitive cDNA (as discussed above). As shown in FIG. 10, channels expressed from this mutant were apparently identical to the wild-type channels in their response to GABA and muscimol, but differed in their response to PTX and dieldrin. Pharmacological comparisons were made using thirty oocytes injected with each type of RNA. These oocytes were obtained from a number of different frogs and showed considerable variability in their response to GABA. However, oocytes expressing RNA derived from the Ala>Ser mutant showed consistently lower sensitivity to PTX and dieldrin (FIGS. 10b–e). As shown by this figure, in oocytes injected with RNA derived from the wild-type "sensitive" cDNA, application of 1 $\mu$M PTX blocked more than 70% of the GABA response (FIG. 10b); this concentration of PTX had little effect in oocytes injected with RNA derived from the Ala to Ser mutant (FIG. 10d). It was necessary to increase the PTX concentration to 100 $\mu$M to obtain a similar degree of block, indicating that the mutation induces approximately 100 fold reduction in sensitivity. This is in agreement with the estimate of 100-fold reduction in sensitivity observed in cultured Rdl$^{R-MD}$ neurons under whole cell patch clamp.

However, GABA-evoked currents were not blocked by the GABA receptor antagonist bicuculline (FIG. 10a). Bicuculline insensitive GABA receptors have been described previously in insects. Lummis, Comp. Biochem. Physiol., 95:1 (1990), and similar insensitivity has also been observed in the recently identified GABA receptors in vertebrate retina, termed GABA$_C$ receptors. Feigenspan et al., Nature 361:159 (1993); Qian and Dowling, Nature 361:162 (1993).

The sensitivity to the cyclodiene insecticide dieldrin was also reduced. Thus, 10 $\mu$M dieldrin caused >75% block of the GABA response in oocytes expressing the wild-type "sensitive" cDNA (FIG. 10c), but had little effect on those expressing the insensitive mutant cDNA (FIG. 10e). Further increase of the dieldrin concentration was not possible due to its limited solubility, but a comparison of the effects of lower doses suggests that the mutation confers 50–100 fold loss of sensitivity to dieldrin. Insensitivity to this concentration of dieldrin is consistent with previous suction electrode recordings taken from the larval central nerve cord of Rdl$^{R-MD}$. Bloomquist et al., Pestic. Sci., 32:463 (1991). Although resistance levels for both PTX and dieldrin may be lower than those observed in bioassays with adult flies, this can be explained by the difficulty of killing more than 50% of homozygous resistant flies in contact bioassays at any dose. Pribilla et al., EMBO J., 11:4305 (1992).

Figure 11:
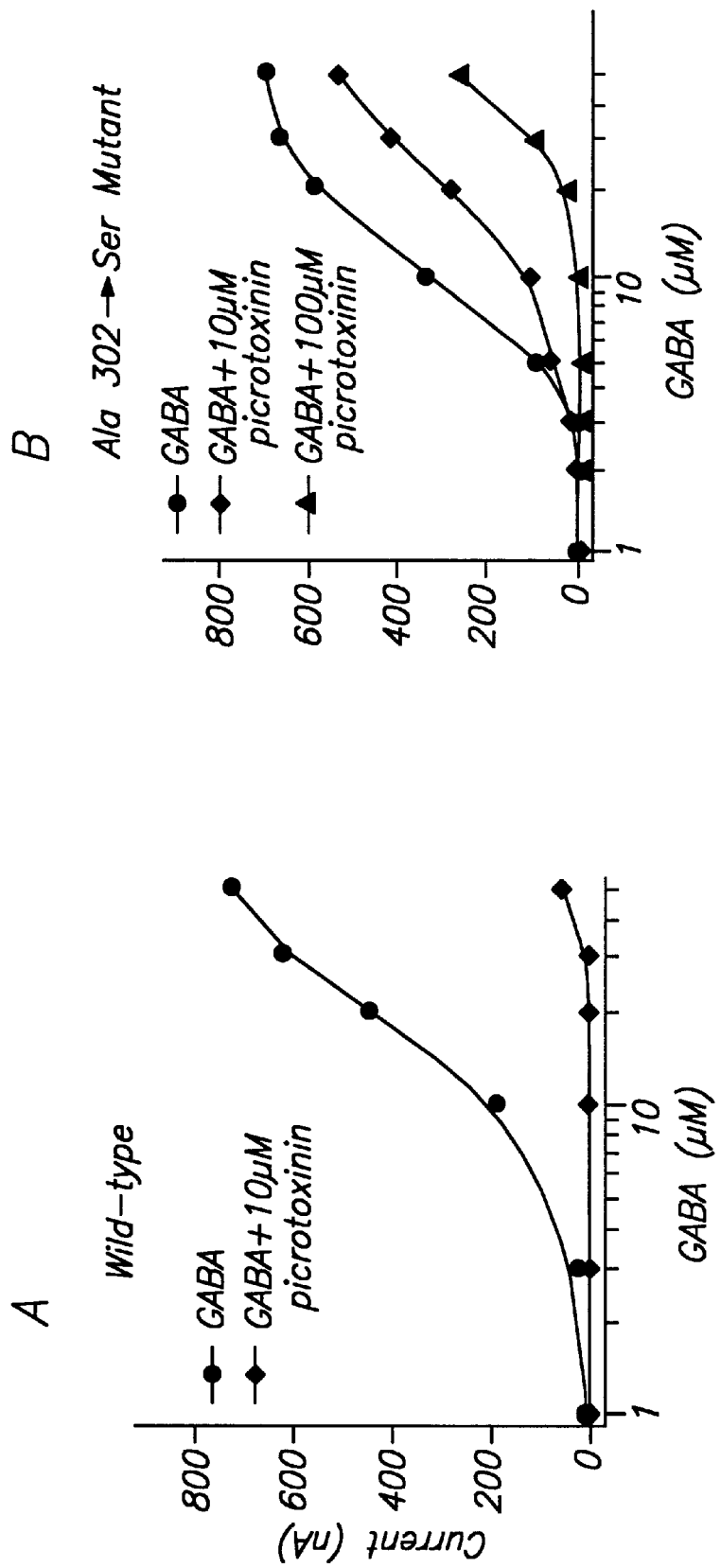
FIG. 11(A) of FIG. 11 shows the dose-response curve observed for individual Xenopus oocytes injected with normal GABA receptor cDNA, and exposed to varying concentrations of GABA and PTX.
FIG. 11(B) of FIG. 11 shows the dose-response curve observed for individual Xenopus oocytes injected with mutant GABA receptor cDNA, and exposed to varying concentrations of GABA and PTX.

Additional oocytes were tested by finding the rough EC$_{50}$ for GABA, then applying one or more concentrations of PTX or dieldrin (some oocytes were treated with more than one concentration). This experiment involved perfusing the oocytes with GABA until maximum response was obtained, then washed out for 5 min. before application of the next higher concentration. Subsequently, PTX or dieldrin was perfused for 10 min., then mixtures of GABA and PTX were applied. At the end of the experiment, the preparation was washed with saline for 20 min. and the response to a high dose of GABA measured. In all experiments, the response to GABA recovered by at least 50% during washing. Complete dose-response curves were obtained for three oocytes of each type, and were similar in shape despite differences in the threshold concentration for the GABA effect. These dose response curves are shown in FIG. 11. Twenty-five of 30 oocytes had a GABA EC$_{50}$ between 10 and 50 $\mu$M, as shown in Table 2.

Figure 12:
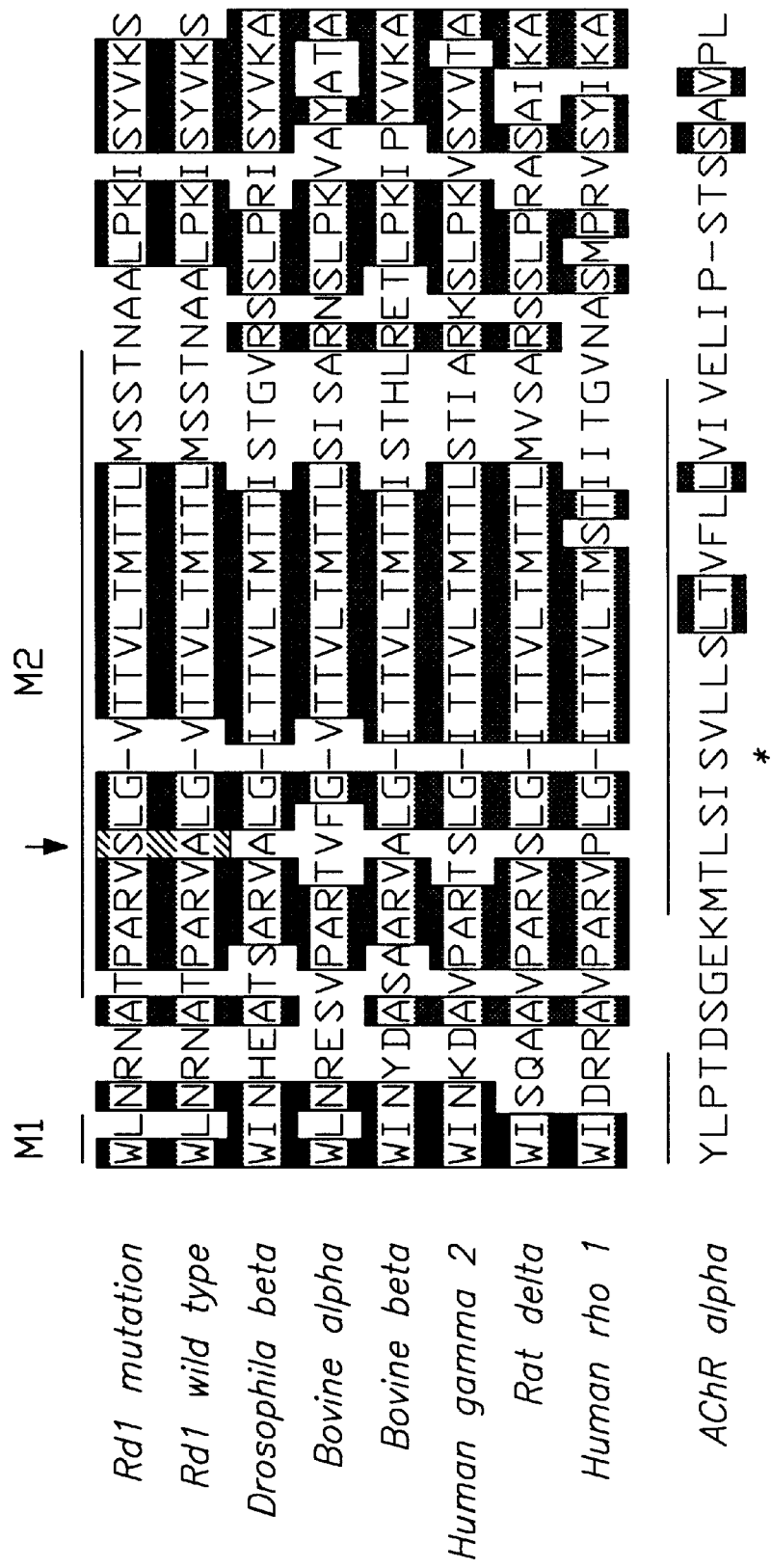
FIG. 12 shows the alignment of various $GABA_A$ receptor subtype amino acid sequences and a nicotinic acetylcholine receptor (AChR)α-subunit sequence.

The location of the substitution at the cytoplasmic (inner) end of M2 in Rdl is analogous (FIG. 12) to the location of the inner polar site of the nicotinic acetylcholine receptor (AChR).

TABLE 2

| | | Reduction In GABA response (%) (mean (s.d.)) | | | | | | |
|---|---|---|---|---|---|---|---|---|
| | | 1 $\mu$M PTX | | 10 $\mu$M PTX | | 50 $\mu$M PTX | | 10 $\mu$M dieldrin | |
| GABA EC$_{50}$ | | Wt | Mutant | Wt | Mutant | Wt | Mutant | Wt | Mutant |
| 10 $\mu$M | | 73 (15) | 8 (10) | 96 (4) | 61 (14) | 96 (5) | 75 (28) | 78 (4) | 23 (21) |
| | | n = 3 | n = 6 | n = 3 | n = 7 | n = 4 | n = 3 | n = 2 | n = 3 |

TABLE 2-continued

| | Reduction In GABA response (%) (mean (s.d.)) | | | | | | | |
|---|---|---|---|---|---|---|---|---|
| | 1 μM PTX | | 10 μM PTX | | 50 μM PTX | | 10 μM dieldrin | |
| GABA EC$_{50}$ | Wt | Mutant | Wt | Mutant | Wt | Mutant | Wt | Mutant |
| 50 μM | 78 (12) n = 9 | 8 (7) n = 7 | 90 (13) n = 6 | 48 (6) n = 4 | 97 (5) n = 5 | 56 (6) n = 5 | 80 (6) n = 4 | 12 (11) n = 6 |

EXAMPLE 4

This experiment describes the plasmid constructs and transfection conditions used with Chinese hamster ovary (CHO-Pro-3) cells.

The plasmid pMSG-14 is constructed by ligating the 2.0 SalI fragment containing the entire Drosophila gene from pBS 14.1 into the SalI site of the expression vector pMSG (Pharmacia, Piscataway, N.J.). The orientation of the Rdl gene is then determined by restriction analysis. To construct pMSG-4.1, the plasmid pBS 4.1 is double digested with DraI and SalI, and the resulting 2.0 kb fragment containing the Rdl gene is ligated into pMSG which has been double digested with SmaI and SalI. These DraI and SmaI digestions result in blunt ends producing compatible ends for proper ligation. Genes cloned into the expression vector pMSG are expressed from the glucocorticoid-inducible promoter present in the mouse mammary tumor virus long terminal repeat (MMTV LTR). The pMSG also contains the E. coli xanthine-guanine phosphoribosyltransferase gene, which provides a marker for selection of stable transformants. Plasmids are purified using a Magic™ Maxipreps kit (Promega, Madison, Wis.), and concentrations are measured spectrophotometrically.

CHO-Pro-3 cells were maintained in F-12 medium (GIBCO, Grand Island, N.Y.) containing 10% heat-inactivated fetal bovine serum at 37° C. in 5% $CO_2$. For transfection, exponentially growing cells are trypsinized, and seeded at 1×10$^5$ cells per plate in 60 mm culture dishes. Upon reaching 30–50% confluence (after approximately 24 hours), the cells are washed twice with PBS, and transfection media containing 10 μg DNA, 25 μl Lipofectin (GIBCO, Grand Island, N.Y.) and 2 ml serum-free F-12 is added to the plates. After 6 hours, the transfection medium is replaced with F-12 medium containing 10% fetal bovine serum. Following a 48-hour post-transfection recovery, the transfected cells are trypsinized and seeded at 1×10$^5$ cells per 60 mm dish. For selection, the growth medium is supplemented with xanthine (0.25 mg/ml), mycophenolic acid (5 μg/ml) and 1× HT supplement (GIBCO BRL). Resistant colonies appear 5–10 days after selection. Individual colonies transformed with either pMSG-14.1 or pMSG-4.1 are isolated and maintained in selective growth media. Rdl expression, in response to dexamethasone, is determined by electrophysiology data and by analysis of mRNA expression.

EXAMPLE 5

As noted above, the present invention contemplates the identification (i.e., diagnosis) of insecticide resistance through use of PCR amplification and specific alleles. This experiment describes the specific identification of cyclodiene resistance in D. melanogaster and D. simulans by PCR amplification of specific alleles.

The origins of resistant and susceptible strains of D. melanogaster and D. simulans, and the preparation of genomic DNA from single flies or strains of flies of known genotype were previously described. ffrench-Constant, Proc. Natl. Acad. Sci., USA 90:1957 (1993). In the accompanying figures, the strains of D. melanogaster are numbered as follows: 1, Maryland; 2, North Carolina; 3–6, Davis, Calif.; 7, Rochester 1988, N.Y.; 8, Rochester 1990, N.Y.; 9, Newfield, N.Y.; 10, Vineland, Ontario; 11–12, Kenya, Africa; 13, Guyana; 14–15, New South Wales, Australia; 16–18, Bamako, Mali; 19–29, Apopka, Fla.; 30–31, Kenya, Africa; 32, Guyana; 33, Fairfield, Australia; 34–36, Kenya, Africa; 37, Guyana; 38, Kenya; 39, Guyana; 40, Mali, Africa; 41–46, Queenstown, Md. Strains of D. simulans are numbered: 1, Davis, Calif.; 2, Kenya, Africa; 3, Piru, Calif.; 4, Gridly, Calif.; 5, La Conchita, Calif.; 6, Japan; 7, Soda Lake, Calif.; 8, Templeton, Calif.; 9, Watsonville, Calif.; 10, Salis, Md.; 11, Riverside.

Figures 13, 18:
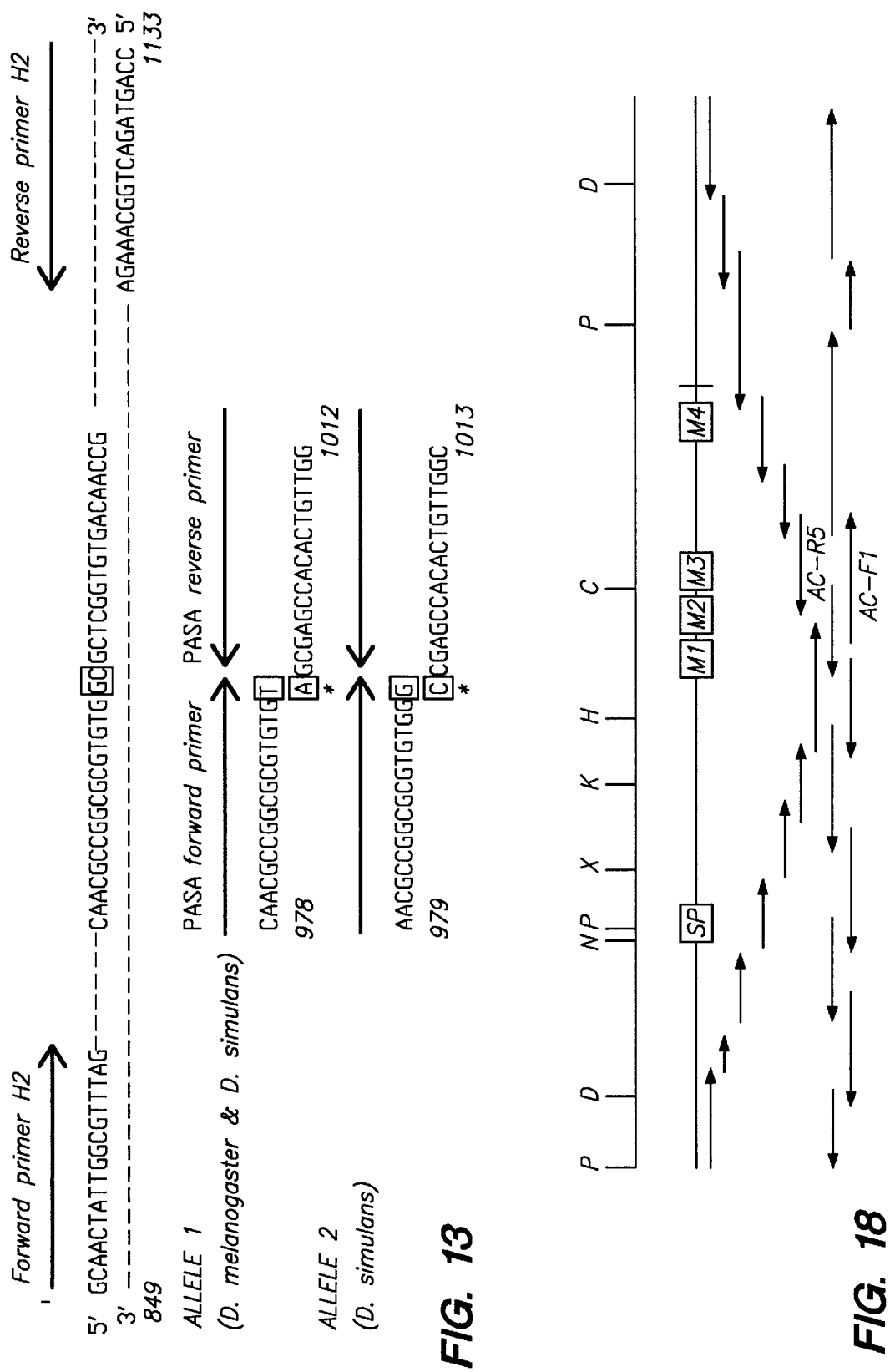
FIG. 13 is a schematic which shows the location of allele-specific primers used in the PCR amplification of resistant D. melanogaster and D. simulans.
FIG. 18 is a schematic diagram of the predicted amino acid sequence of the cDNA clone 2.1.3.

Allele specific PCR primers were made by placing the specific single base mutation at the 3' end of the oligonucleotide. Primers were made in both the forward and the reverse orientations in order to maximize the chances of finding a primer capable of discriminating between alleles. The allele specific primers and the sequences from which they were chosen are shown in FIG. 13. In FIG. 13, the positions of bases substituted in resistance-associated mutations are boxed and the positions of the allele specific nucleotides at the 3' ends of the PASA primers are indicated by an asterisk. As described below, PCR was performed between these primers and flanking primers known to be nested within exon 7 of Rdl which contains the resistance associated mutation.

In order to guard against false negative results (i.e., failure of the PCR reaction or omission of sample DNA) where absence of product could lead to misclassification, a second set of primers (F12 [SEQ ID NO:14] and P16 [SEQ ID NO:15]) which make a 406 bp product independent of resistance status of the DNA under examination was used.

Figure 14:
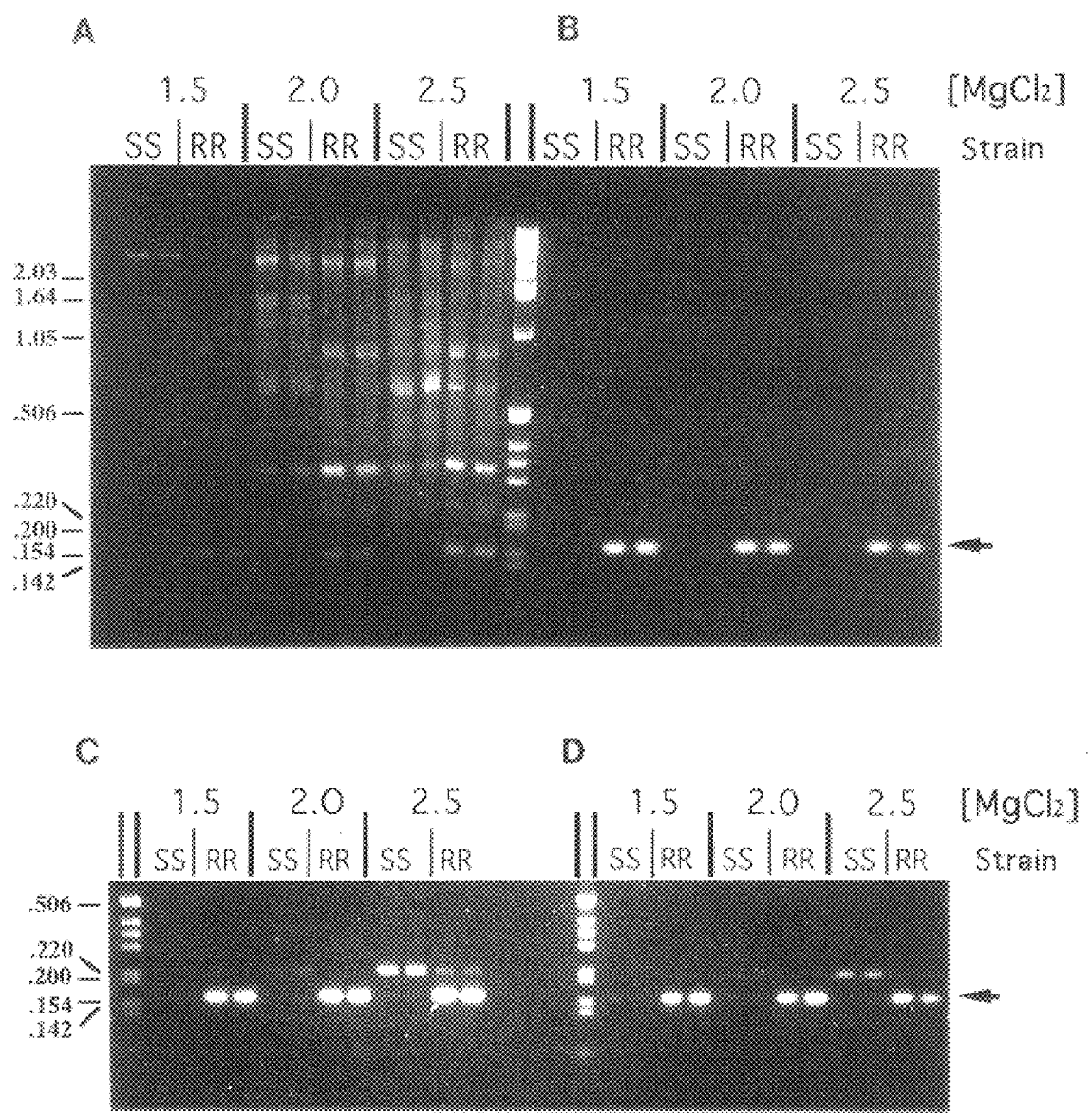
FIG. 14 shows the results for PASA PCR of resistant and susceptible D. melanogaster and D. simulans strains at a range of $MgCl_2$ concentrations.

For PCR approximately 100 ng of genomic DNA was added to a 50 μl reaction containing 0.2 μM of the allele specific primer and the allele independent primer on the same strand, 0.2 mM dNTPs and 1.5 units of Taq polymerase. PCR was performed for 30 cycles and with 1' denaturation at 94° C., 2' annealing at 50° C. and 3' extension at 72° C. The concentration of magnesium in the reaction was varied (1.5, 2.0 or 2.5 mM $MgCl_2$) in order to determine the conditions under which specific resistance alleles were amplified. PCR products were electrophoresed in a 4% agarose gel and visualized by staining with ethidium bromide (FIG. 14).

In most cases, either the forward or the reverse primer gave stronger discrimination between susceptible DNA and specific resistance alleles. Further, one of the primers was often associated with a large amount of non-specific products (FIGS. 14a, b). FIGS. 14(a) and 14(b) show the PASA products from D. simulans homozygous susceptible SS(Riverside) and homozygous resistant RR (allele 2, Africa); products are shown from both forward (14a) and reverse (14b) allele specific primers at a range of $MgCl_2$ concentrations (1.5 to 2.5 mM). FIG. 14(c) shows the PASA PCR products from homozygous susceptible SS and resistant RR (S; OregonR, R; Maryland) D. melanogaster at the same $MgCl_2$ concentration range. FIG. 14(d) shows the PASA PCR products for D. simulans (S; Riverside, R; Davis) allele 1, tested at the same $MgCl_2$ concentration range.

Whereas specific amplification of the resistant allele (FIG. 14, arrow) alone is achieved at a range of $MgCl_2$ concentrations with the reverse primer, the forward primer amplifies a number of secondary larger products at all $MgCl_2$ concentrations. The optimal magnesium concentrations for discriminating each allele with the primer of choice (forward or reverse) in each species was 1.5 mM $MgCl_2$ (FIGS. 14c,d). At higher than optimal concentrations, secondary non-specific, products begin to appear, particularly in the susceptible samples.

Figure 15:
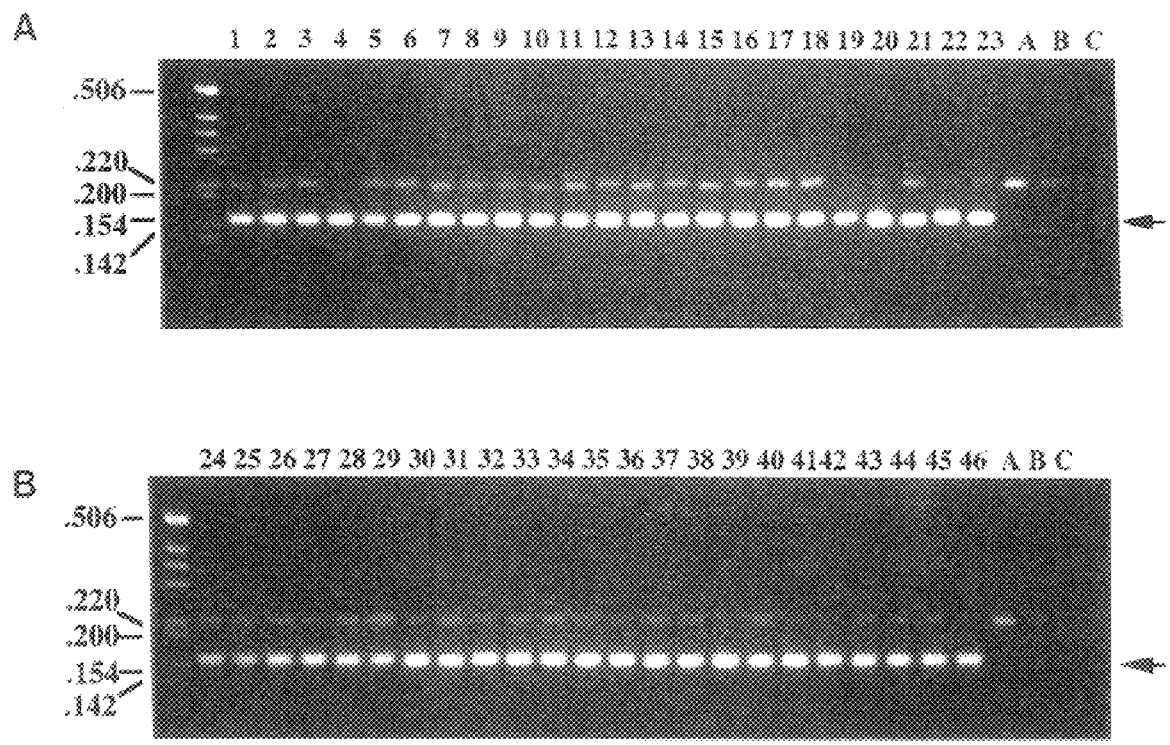
FIG. 15 shows the PASA PCR products from homozygous *D. melanogaster* strains.

FIG. 15 shows the PASA PCR products from homozygous resistant strains of D. melanogaster from around the world. Strain numbers refer to the collecting locations previously given. The position of the resistance associated PASA product is indicated by an arrow. The controls were: in lane A, a standard susceptible strain (OregonR); in lane B, resistance allele from D. simulans; and in lane C, no DNA. Size markers are shown in kb. As indicated, the specific resistance allele 1 could be detected in all of the 46 strains of D. melanogaster examined (FIG. 15) and either allele 1 or 2 could be detected in the ten strains of D. simulans (FIG. 16).

Figure 16:
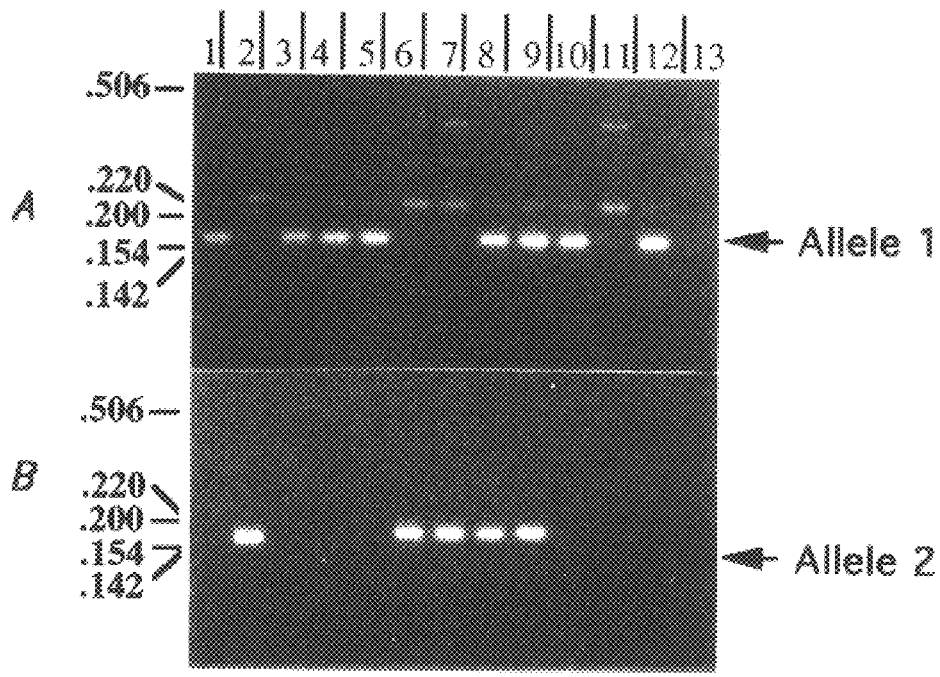
FIG. 16 shows the results of PCR amplification for resistant alleles 1 and 2 of *D. simulans*.

FIG. 16 shows the amplification of cyclodiene resistance allele 1 (top panel) and allele 2 (bottom panel) from homozygous resistant D. simulans (lanes 1–10). Strain numbers are those previously indicated. Control lanes (FIG. 16) show that each allele specific primer does not amplify any other resistant or susceptible allele, and that no product is formed in the absence of Drosophila DNA.

Figure 17:
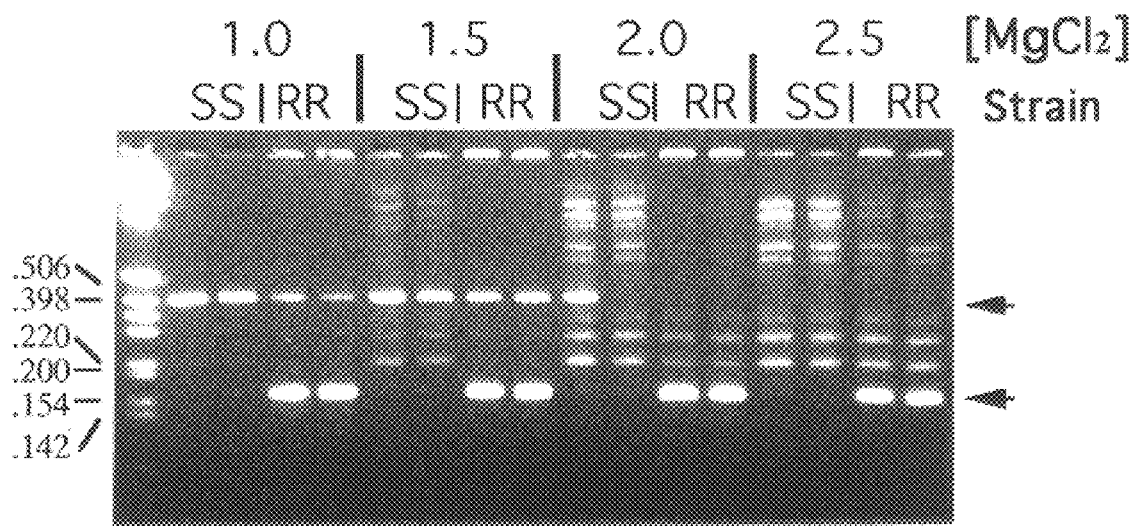
FIG. 17 shows the results of PCR amplification using nested primers.

FIG. 17 shows the results produced with inclusion of a second set of allele independent PCR primers in PASA products from homozygous susceptible (oregonR) and resistant R (Maryland) D. melanogaster, at a range of $MgCl_2$ concentrations (1.0 to 2.5 mM)(size markers are in kb). The position of the resistance associated PASA product is indicated by the lower arrow and the allele independent control product by the upper arrow. For simultaneous use of a second primer set, the distinguishing $MgCl_2$ concentration is 1.0 mM. Thus, the use of the second set of allele independent primers successfully produced a second product whose appearance was independent of resistance status but is also obviously similarly dependent on magnesium concentration.

EXAMPLE 6

In order to determine whether the methods of the present invention are applicable to harmful insects, this experiment describes the successful cloning of an Rdl homolog from A. aegypti by means of a low stringency screen with the Drosophila probe. The conservation of resistance in Drosophila and other insects such as A. aegypti permits the use of the probes, primers, amplification, screening formats, and other aspects of the present invention for detection of pesticide resistance in genera other than Drosophila.

The mosquito cDNA clone (2.1.3) was isolated from a library constructed of RNA extracted from adult A. aegypti. RNA was polyA and size selected for messages greater than 2 kb. The cDNA library was constructed in the vector λGT10 and screened at low stringency (16 hour hybridization at 50° C. in 10% dextran sulfate, 0.5M $NaPO_4$, 5% SDS, 0.001 M EDTA, and 36 µg/ml single stranded salmon sperm DNA; two washes at room temperature in 2× SSC and 0.5% SDS for 5 minutes; two washes at 50° C. in 2× SSC and 1% SDS for 30 minutes), with a gel purified restriction fragment (0.76 kb EcoR1 fragment isolated in low melting temperature agarose (Sea-plaque®, FMC BioProducts, Rockland, Me.) and radio-labelled with $^{32}P$ by primer extension) from the Drosophila Rdl clone which contains the first three of the highly conserved membrane spanning regions M1–3. DNA sequencing was carried out by the dideoxy chain termination method using the Sequenase kit (United States Biochemical) and 18-mer oligonucleotides synthesized in an Applied Biosystems (Foster City, Calif.) DNA synthesizer as primers.

Analysis of the cDNA clone 2.1.3 is illustrated in FIG. 18, which gives a schematic diagram of the predicted amino acid sequence and shows the position of the signal peptide (SP) and the four predicted membrane-spanning hydrophobic sequences (M1–4). Above is shown a restriction map, with the following: P, PstI; D, DraI; N, NarI; X, XbaI; K, KpnI; H, HindIII; C, ClaI. Below, the positions of the individual sequencing runs on both strands of the DNA are shown by arrows. The location of sequences derived from the PCR primers (AC-F1 and AC-R5) used in amplification of the region containing the resistance associated mutation are also given.

The predicted amino acid sequence of the mosquito cDNA was aligned and compared with that of Drosophila, using the GAP program in the UW-GCG package. The results are shown in FIG. 19. The alanine residue substituted by a serine in the resistant strain is boxed. The signal cleavage site predicted from alignment of Rdl with vertebrate GABA receptors is shown by an arrow above the sequence. The two locations showing alternative splicing of two exons of the same size (a or b, and c or d) are indicated by arrows below the sequence. The proposed membrane-spanning hydrophobic sequences are indicated by solid bars and the β structural loop flanked by cysteines is indicated by a broken line. Vertical lines indicate amino acid identity, single and double dots between residues indicate conservative changes and dots within the sequence indicate gaps.

Northern blotting was performed with polyA RNA selected from adult mosquitoes according to standard procedures. See Sambrook et al., supra.

The resistance associated mutation was sequenced from the cyclodiene resistant strain Isla Verde. The Liverpool susceptible strain was used for comparison. Following PCR, the products were cloned into the pCRII vector (Invitrogen, La Jolla, Calif.) using the manufacturer's instructions and sequenced. The PCR primers used (ACF1 [SEQ ID NO:16] and ACR5 [SEQ ID NO:17]) were predicted to be internal to exon 7 of the mosquito gene (see FIG. 18), by analogy with the genomic organization of the Drosphila gene.

A restriction map of the mosquito clone 2.1.3 and the strategy used to sequence it are shown in FIG. 18. The predicted amino acid sequence of the mosquito cDNA is compared to that of D. melanogaster Rdl in FIG. 19. The two sequences were shown to have 87% identity. The two locations in the extracellular domain which show alternative splicing of two exons of equal size in Drosophila (termed 'a' or 'b', and 'c' or 'd'), carry sequences nearly identical to Drosophila exons a and C. The sequence of the membrane spanning regions (M1–4) is almost identical, with only one conservative amino acid substitution in M1. The sequence of the presumed extracellular domain is also nearly identical with only four substitutions. In contrast, the presumed intracellular domain is much shorter in the mosquito.

Northern analysis of polyA selected RNA from adult mosquitoes showed a transcript size of approximately 10 kb. This is consistent with the large transcript size observed for Drosophila Rdl of approximately 8 kb.

Figure 20:
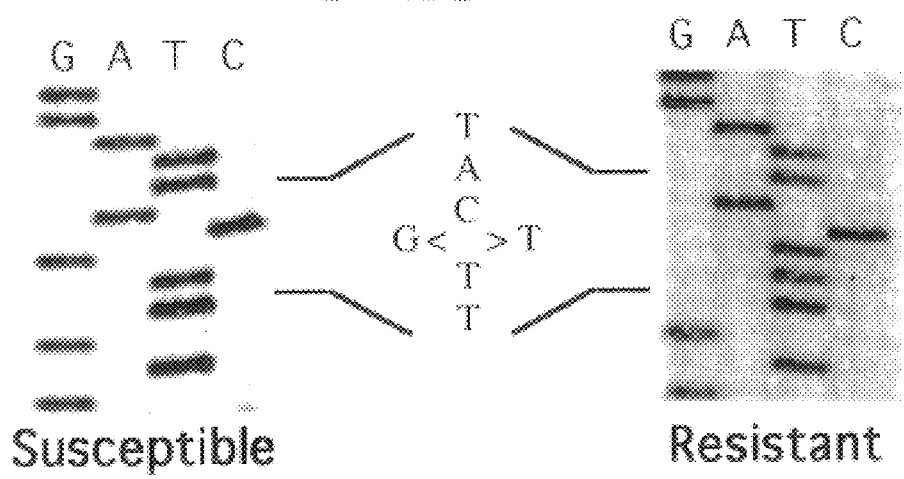
FIG. 20 shows the sequencing of PCR-derived clones from cyclodiene resistant and susceptible *A. aegypti* and the significant nucleotide change.

This PCR-based sequencing of the second membrane spanning region of the Rdl homolog from the resistant mosquito strain showed a single base pair substitution of a G to a T at nucleotide position 885, thus replacing an alanine (GCA) with a serine (TCA). The mutation is illustrated in FIG. 20. This is exactly the same mutation as found in resistant *D. melanogaster*, which was proven to be functionally involved in conferring insensitivity of expressed chloride ion channels to picrotoxin and dieldrin.

Thus, the conservation of the GABA receptor between insects facilitates its use as a selectable marker in genetic transformation of insects of various genera.

EXAMPLE 7

This example describes the genotyping of three insect pests. Degenerate primers were used in PCR to isolate sequences from the pest insect Rdl homologues corresponding to the location of the resistance-associated mutation in Drosophila. The pest insects were chosen so as to represent different orders (Lepidoptera, Diptera, Coleoptra, and Dictyoptera), and included susceptible and resistant strains of cockroaches (*Periplaneta americana*), house flies (*Musca domestica*) and red flour beetle (*Tribolium castaneum*). Susceptible cockroaches were a standard strain maintained in the laboratory and resistant strains were collected from Miami in 1990 and Jacksonville, Fla. in 1988. Susceptible house flies were from a standard laboratory strain S+ and resistant flies were Dieldrin-R, a dieldrin-selected strain maintained for 20 years in the laboratory. Production of the isogenic susceptible (Lab-S) and resistant (lin-R) red flour beetle strains has been described elsewhere. Beeman and Stuart, J. Econ. Entomol., 83:1745 (1990). A number of susceptible insects were also examined for which no resistant counterparts were analyzed. These included corn rootworms (French Laboratory), *Heliothis virescens* and *H. zea*, both from long-established laboratory colonies. Western corn rootworm of both diapausing and non-diapausing varieties were examined.

Figure 21:
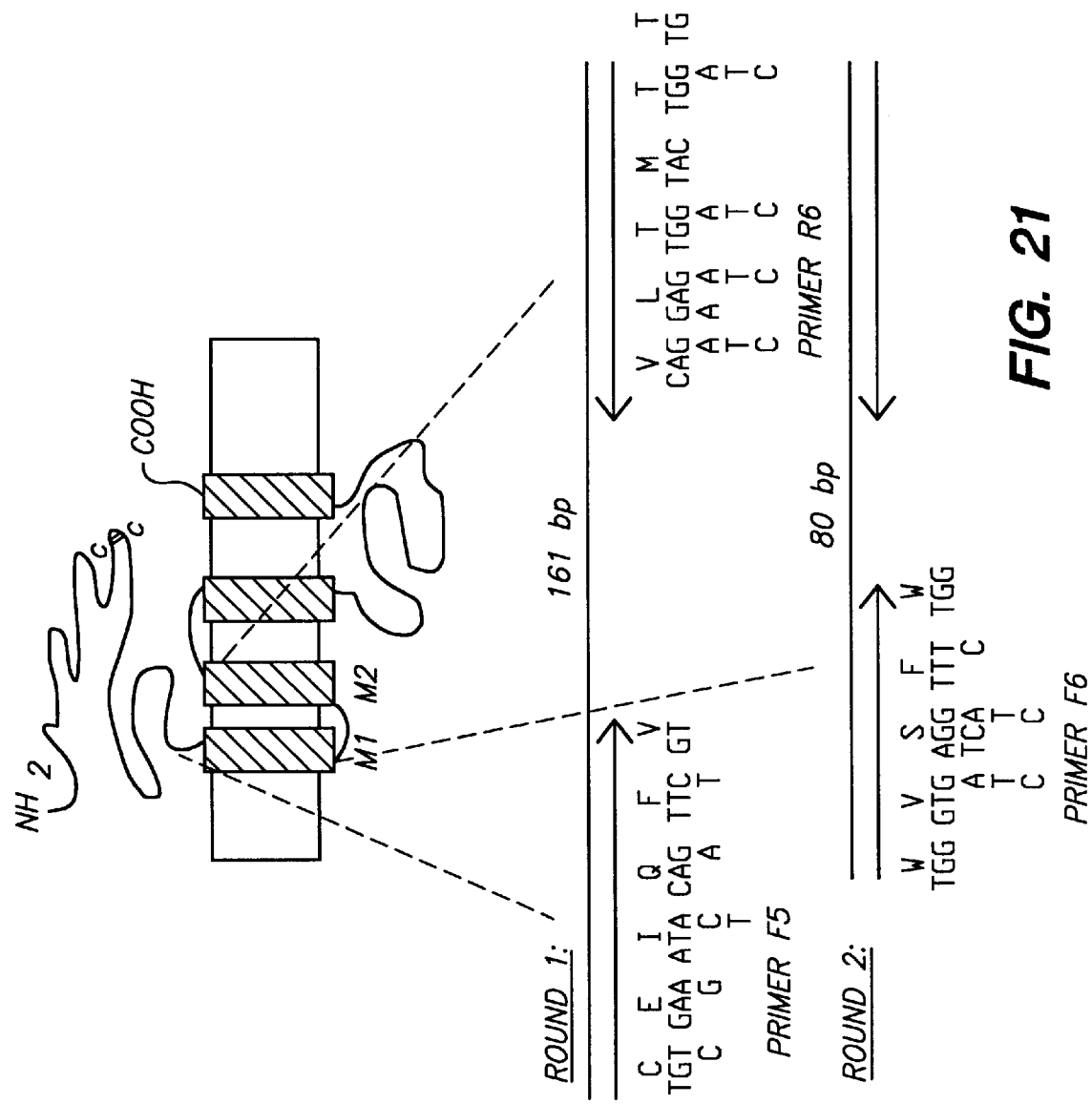
FIG. 21 shows the location of the degenerate PCR primers used to amplify the section of Rdl containing the resistance in Drosophila.

FIG. 21 shows the location of the degenerate PCR primers used to amplify the section of Rdl containing the resistance associated mutation in Drosophila. These primers were based on regions of conserved amino acid sequence between Rdl of *D. melanogaster* and the homolog from *A. aegypti*. Thompson et al., FEBS Lett., (accepted for publication). A schematic diagram of the Rdl GABA subunit is shown and dotted lines show the relative locations of the different PCR primers.

Degenerate primers from exon 7 of *D. melanogaster* were used to directly amplify approximately 50–250 ng of genomic DNA extracted from the insects as previously described. ffrench-Constant et al., Proc. Natl. Acad. Sci. USA 90:1957 (1993). Two rounds of amplification were performed. In the first round, primers just 5' to M1 (F5, 48-fold degenerate; SEQ ID NO:18) and within M2 (R6, 512-fold degenerate; SEQ ID NO:19) were used to amplify a 161 bp product. Following gel isolation (4% agarose) of this first round product, a smaller 80 bp section of DNA was amplified from within the product using one of the same first round primers (R6; SEQ ID NO:17) and a third novel primer (F6, 128-fold degenerate; SEQ ID NO:20) within M1. The product from the second round of amplification contains the most intracellular part of M2, the region carrying the resistance-associated mutation in *D. melanogaster*. The second PCR product was cloned and sequenced from susceptible and resistant strains of three insect pests.

First round PCR products were gel purified by excision from the agarose gel, freezing, spinning and then adding 1 μl of the supernatant to the second round reaction. Second round PCR products were cloned into the pCRII vector (Invitrogen, La Jolla, Calif.) and sequenced with Sequenase II (Bethesda Research Laboratories, Gaithersburg, Md.) as double-stranded templates, using Sp6 and T7 primers within the vector, according to the manufacturer's instructions.

Figure 22:
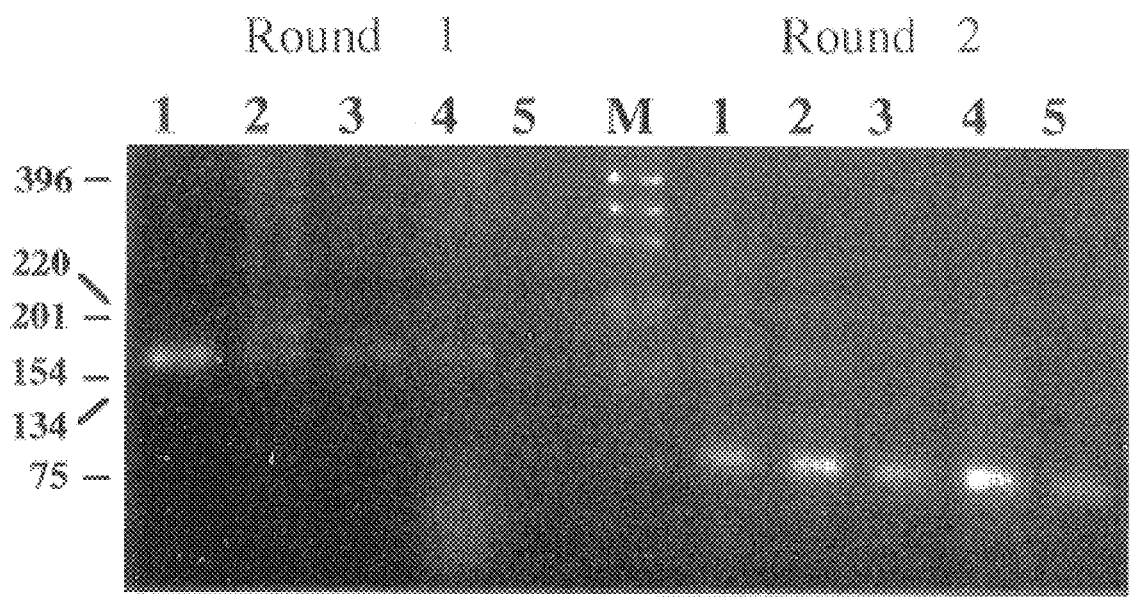
FIG. 22 shows the Rdl PCR amplification products from genomic DNA of different insect species containing the resistance associated mutation.

Sequencing of second round PCR products shows that the region connecting M1 and M2 is extremely conserved in different insect species (See FIG. 22). The only amino acid residue showing consistent variations is asparagine-295 (ffrench-Constant et al., Proc. Natl. Acad. Sci. USA 88:7209, 1991) which is sometimes replaced by aspartic acid. The same variation in this amino acid position is also present in some vertebrate $GABA_A$ receptor subtypes. ffrench-Constant et al., Proc. Natl. Acad. Sci. USA 90:1957 (1993). Analysis of three homozygous susceptible (SS) and resistant (RR) strains of pest insects shows that exactly the same single base pair substitution (G>T) as found in *D. melanogaster*, causing the replacement of an alanine with a serine (GCN>TCN, where N is A,C,T or G), is found in other cyclodiene resistant insects.

FIG. 22 shows Rdl PCR amplification products from genomic DNA of different insect species, from the region containing the resistance associated mutation in Drosophila. Lane 1 is a positive control (*D. melanogaster* NB14.1 Rdl cDNA); Lane 2 is *P. americana*, Jacksonville; Lane 3 is *M. domestica*, S+4; Lane 4 is *M. domestics*, Dieldrin-R; and Lane 5 is *T. castaneum*, Lab-S. Molecular markers are shown in bp. Products in round 2 appear to be increased in size in lanes 1–5, due to anomalous "frowning" of the gel.

FIG. 23 shows the nucleotide sequences and deduced amino acid sequence of the 80 bp product from a) cyclodiene susceptible insects and b) three cyclodiene susceptible (S) and resistant (R) strains compared with the two alleles found in Drosophila. Allele one, found in both *D. melanogaster* and *D. simulans*, contains the resistance associated mutation Ala to Ser (A>S). Allele 2, found only in *D. simulans*, is associated with the substitution Ala to Gly (A>G). All three pest species examined carried the same Ala>Ser mutation as allele 1 in Drosophila. Arrows below the nucleotide sequences indicate which base pair has been mutated and the corresponding amino acid substitution is shown in single letter code. Some nucleotide degeneracy is found at third base positions; K, G or T; M, A or C; R, A or G; S, C or G; W, A or T; Y, C or T.

From the above descriptions and examples, it should be clear that the methods and reagents of the present invention represent an easy, reliable method to determine the safety and efficacy of new compounds, including insecticides. The present invention also provides a rapid method of diagnosing insecticide resistance in field or laboratory collections of insects. The methods are amenable to screening insecticides in an in vitro assay prior to any field testing.

What is claimed is:

1. A purified and isolated nucleic acid encoding an invertebrate GABA receptor, wherein said nucleic acid sequence is selected from the group consisting of SEQ ID NOS: 3, 5, and 7.

2. A non-Drosophila host cell containing a functional DNA sequence selected from the group consisting of SEQ ID NOS: 3, 5, and 7, which renders said host cell capable of expressing an invertebrate GABA receptor.

3. The non-Drosophila host cell of claim 2, wherein said cell is an insect cell.

4. The non-Drosophila host cell of claim 3, wherein said cell is a mosquito cell.

5. The host cell of claim 3, wherein said host cell is within a living insect.

6. The host cell of claim 2, wherein said host cell is eukaryotic.

7. The non-Drosophila host cell of claim 2, wherein said cell is a mammalian cell.

8. The non-Drosophila host cell of claim 7, wherein said cell is a hamster cell.

9. The non-Drosophila host cell of claim 2, wherein said cell is an amphibian cell.

10. The non-Drosophila host cell of claim 9, wherein said cell is a Xenopus cell.

* * * * *

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 637 amino acids
      (B) TYPE: amino acid
      (D) TOPOLOGY: unknown (ii) MOLECULE TYPE: peptide (vi) ORIGINAL SOURCE:
      (A) ORGANISM: Drosophila melanogaster (viii) POSITION IN GENOME:
      (A) CHROMOSOME/SEGMENT: III; polytene subregion 66F
      (B) MAP POSITION: approximately map unit 26

(xi) SEQUENCE DESCRIPTION: SEQ ID NO:1:

```
Ser Leu Leu Val Leu Phe Ala Glu Ala Gln Asn Lys Arg Ser Thr Leu
 1               5                  10                  15

Gly Pro Ala Pro Pro Pro Pro Lys Thr His Ser Thr Thr Met
            20                  25                  30

Ser Asp Ser Lys Met Asp Lys Leu Ala Arg Met Ala Pro Leu Pro Arg
            35                  40                  45

Thr Pro Leu Leu Thr Ile Trp Leu Ala Ile Asn Met Ala Leu Ile Ala
    50                  55                  60

Gln Glu Thr Gly His Lys Arg Ile His Thr Val Gln Ala Ala Thr Gly
65                  70                  75                  80

Gly Gly Ser Met Leu Gly Asp Val Asn Ile Ser Ala Ile Leu Asp Ser
                85                  90                  95

Phe Ser Val Ser Tyr Asp Lys Arg Val Arg Pro Asn Tyr Gly Gly Pro
                100                 105                 110

Pro Val Glu Val Gly Val Thr Met Tyr Val Leu Ser Ile Ser Ser Val
        115                 120                 125

Ser Glu Val Leu Met Asp Phe Thr Leu Asp Phe Tyr Phe Arg Gln Phe
130                 135                 140

Trp Thr Asp Pro Arg Leu Ala Tyr Arg Lys Arg Pro Gly Val Glu Thr
145                 150                 155                 160

Leu Ser Val Gly Ser Glu Phe Ile Lys Asn Ile Trp Val Pro Asp Thr
                165                 170                 175

Phe Phe Val Asn Glu Lys Gln Ser Tyr Phe His Ile Ala Thr Thr Ser
                180                 185                 190

Asn Glu Phe Ile Arg Val His His Ser Gly Ser Ile Thr Arg Ser Ile
                195                 200                 205

Arg Leu Thr Ile Thr Ala Ser Cys Pro Met Asn Leu Gln Tyr Phe Pro
        210                 215                 220

Met Asp Arg Gln Leu Cys His Ile Glu Ile Glu Ser Phe Gly Tyr Thr
225                 230                 235                 240

Met Arg Asp Ile Arg Tyr Phe Trp Arg Asp Gly Leu Ser Ser Val Gly
                245                 250                 255

Met Ser Ser Glu Val Glu Leu Pro Gln Phe Arg Val Leu Gly His Arg
                260                 265                 270

Gln Arg Ala Thr Glu Ile Asn Leu Thr Thr Gly Asn Tyr Ser Arg Leu
                275                 280                 285
```

```
Ala Cys Glu Ile Gln Phe Val Arg Ser Met Gly Tyr Tyr Leu Ile Gln
    290                 295                 300

Ile Tyr Ile Pro Ser Gly Leu Ile Val Val Ile Ser Trp Val Ser Phe
305                 310                 315                 320

Trp Leu Asn Arg Asn Ala Thr Pro Ala Arg Val Ala Leu Gly Val Thr
                325                 330                 335

Thr Val Leu Thr Met Thr Thr Leu Met Ser Ser Thr Asn Ala Ala Leu
            340                 345                 350

Pro Lys Ile Ser Tyr Val Lys Ser Ile Asp Val Tyr Leu Gly Thr Cys
        355                 360                 365

Phe Val Met Val Phe Ala Ser Leu Leu Glu Tyr Ala Thr Val Gly Tyr
370                 375                 380

Met Ala Lys Arg Ile Gln Met Arg Lys Gln Arg Phe Met Ala Ile Gln
385                 390                 395                 400

Lys Ile Ala Glu Gln Lys Lys Gln Gln Leu Asp Gly Ala Asn Gln Gln
                405                 410                 415

Gln Ala Asn Pro Asn Pro Asn Ala Asn Val Gly Gly Pro Gly Gly Val
                420                 425                 430

Gly Val Gly Pro Gly Gly Pro Gly Pro Gly Gly Val Asn Val
            435                 440                 445

Gly Val Gly Met Gly Met Gly Pro Glu His Gly His Gly His Gly His
        450                 455                 460

His Ala His Ser His Gly His Pro His Ala Pro Lys Gln Thr Val Ser
465                 470                 475                 480

Asn Arg Pro Ile Gly Phe Ser Asn Ile Gln Gln Asn Val Gly Thr Arg
                485                 490                 495

Gly Cys Ser Ile Val Gly Pro Leu Phe Gln Glu Val Arg Phe Lys Val
            500                 505                 510

His Asp Pro Lys Ala His Ser Lys Gly Gly Thr Leu Glu Asn Thr Val
        515                 520                 525

Asn Gly Gly Arg Gly Gly Pro Gln Ser His Gly Pro Gly Pro Gly Gln
530                 535                 540

Gly Gly Gly Pro Pro Gly Gly Gly Gly Gly Gly Gly Gly Gly Gly
545                 550                 555                 560

Pro Pro Glu Gly Gly Gly Asp Pro Glu Ala Ala Val Pro Ala His Leu
                565                 570                 575

Leu His Pro Gly Lys Val Lys Lys Asp Ile Asn Lys Leu Leu Gly Ile
                580                 585                 590

Thr Pro Ser Asp Ile Asp Lys Tyr Ser Arg Ile Val Phe Pro Val Cys
        595                 600                 605

Phe Val Cys Phe Asn Leu Met Tyr Trp Ile Ile Tyr Leu His Val Ser
        610                 615                 620

Asp Val Val Ala Asp Asp Leu Val Leu Leu Gly Glu Glu
625                 630                 635
```

(2) INFORMATION FOR SEQ ID NO:2:

(i) SEQUENCE CHARACTERISTICS:
        (A) LENGTH: 2066 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:2:

AAGCTTGCTT GTTCTTTTTG CAGAAGCTCA GAATAAACGC TCAACTTTGG GACCTGCACC    60

```
CCCCCCCCCC CCCCCCAAAA CACACAGCAC CACCATGAGT GATTCAAAAA TGGACAAGCT      120

GGCCCGGATG GCGCCCCTGC CCCGCACACC GCTGCTAACC ATCTGGCTGG CCATCAACAT      180

GGCCCTGATT GCACAGGAAA CGGGCCACAA ACGGATCCAT ACAGTGCAAG CGGCGACTGG      240

CGGTGGCAGC ATGCTGGGTG ACGTAAACAT ATCCGCTATT CTCGACTCCT TTAGTGTTAG      300

TTACGACAAA AGAGTAAGAC CCAATTACGG TGGTCCCCCT GTGGAGGTTG GCGTCACAAT      360

GTATGTCCTC AGTATCAGTT CGGTTTCGGA AGTTCTAATG GACTTCACAT TGGATTTTTA      420

CTTTCGTCAA TTTTGGACCG ATCCTCGTTT AGCGTATAGA AAACGACCTG GTGTAGAAAC      480

ACTATCGGTT GGATCAGAGT TCATTAAGAA TATTTGGGTA CCTGACACCT TTTTTGTAAA      540

TGAAAAACAA TCATATTTTC ACATTGCAAC AACCAGTAAT GAATTCATAC GTGTGCATCA      600

TTCTGGATCG ATAACAAGAA GTATTAGATT GACTATAACC GCATCGTGTC CGATGAATCT      660

ACAATATTTC CCCATGGATC GCCAGCTGTG CCACATTGAA ATCGAAAGCT TCGGTTACAC      720

GATGCGAGAT ATCCGATATT TCTGGAGAGA TGGACTGAGT AGTGTTGGCA TGAGCAGTGA      780

GGTCGAACTA CCGCAGTTCC GAGTTTTGGG ACACAGGCAG AGGGCGACCG AAATAAACCT      840

AACCACAGGC AACTATTCGC GTTTAGCCTG CGAAATTCAG TTCGTGCGTT CGATGGGCTA      900

CTACCTTATA CAAATCTACA TACCCTCTGG ACTGATCGTT GTTATATCAT GGGTATCATT      960

TTGGCTCAAT CGCAATGCAA CGCCGGCGCG TGTGGCGCTC GGTGTGACAA CCGTGTTGAC     1020

AATGACCACT TTGATGTCGT CAACAAATGC AGCGCTGCCA AGATTTCGT ACGTCAAATC      1080

GATTGACGTC TATCTGGGAA CATGCTTCGT TATGGTCTTT GCCAGTCTAC TGGAATACGC     1140

CACGGTCGGC TACATGGCAA AACGAATTCA AATGCGAAAA CAAAGATTTA TGGCGATCCA     1200

AAAGATAGCC GAACAGAAAA AGCAACAGCT CGACGGAGCG AACCAACAGC AGGCGAATCC     1260

CAATCCCAAT GCAAATGTGG GCGGACCCGG AGGAGTGGGC GTTGGACCCG GCGGACCCGG     1320

AGGACCCGGT GGCGGGGTCA ATGTGGGCGT CGGTATGGGC ATGGGACCGG AACATGGCCA     1380

CGGGCATGGA CACCACGCCC ACAGCCATGG ACATCCGCAT GCGCCCAAGC AAACAGTGAG     1440

TAACCGCCCA ATCGGCTTTT CCAATATCCA ACAAAACGTT GGTACGCGCG GTTGCTCGAT     1500

AGTGGGACCC TTGTTCCAGG AGGTGAGATT CAAGGTCCAC GACCCGAAGG CCCACTCCAA     1560

GGGCGGAACG CTGGAGAATA CGGTGAATGG CGGACGCGGT GGTCCGCAAT CGCATGGACC     1620

GGGTCCGGGC CAAGGCGGCG GACCGCCCGG CGGTGGCGGA GGCGGTGGAG GCGGGGGCGG     1680

ACCGCCCGAG GGCGGTGGCG ATCCGGAGGC AGCGGTTCCA GCCCATCTCC TACATCCGGG     1740

AAAAGTAAAA AAGGACATCA ACAAGCTGCT GGGCATCACG CCCTCCGACA TCGACAAGTA     1800

CTCACGCATC GTGTTCCCCG TGTGCTTTGT GTGCTTCAAC CTGATGTACT GGATCATTTA     1860

CCTGCATGTC AGCGACGTGG TCGCCGATGA TCTGGTGCTT CTGGGCGAGG AGTAGAGCGT     1920

CGTACTCAAG CGGCGCAAGT AGTCGAGGGC GTGGCCCAAG GACACAGGAG TGAACAGCGC     1980

GCGAGAGAGT CAAACTTGGC AGGGCACTGA AAAACCACAC AAAAAATAGA AAAAAAAAA     2040

AAACGAATGC TGCGGCCGCC GAATTC                                         2066
```

(2) INFORMATION FOR SEQ ID NO:3:

(i) SEQUENCE CHARACTERISTICS:
        (A) LENGTH: 2066 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:3:

```
AAGCTTGCTT GTTCTTTTTG CAGAAGCTCA GAATAAACGC TCAACTTTGG GACCTGCACC        60
CCCCCCCCCC CCCCCCAAAA CACACAGCAC CACCATGAGT GATTCAAAAA TGGACAAGCT       120
GGCCCGGATG GCGCCCCTGC CCCGCACACC GCTGCTAACC ATCTGGCTGG CCATCAACAT       180
GGCCCTGATT GCACAGGAAA CGGGCCACAA ACGGATCCAT ACAGTGCAAG CGGCGACTGG       240
CGGTGGCAGC ATGCTGGGTG ACGTAAACAT ATCCGCTATT CTCGACTCCT TTAGTGTTAG       300
TTACGACAAA AGAGTAAGAC CCAATTACGG TGGTCCCCCT GTGGAGGTTG GCGTCACAAT       360
GTATGTCCTC AGTATCAGTT CGGTTTCGGA AGTTCTAATG GACTTCACAT TGGATTTTTA       420
CTTTCGTCAA TTTTGGACCG ATCCTCGTTT AGCGTATAGA AAACGACCTG GTGTAGAAAC       480
ACTATCGGTT GGATCAGAGT TCATTAAGAA TATTTGGGTA CCTGACACCT TTTTTGTAAA       540
TGAAAAACAA TCATATTTTC ACATTGCAAC AACCAGTAAT GAATTCATAC GTGTGCATCA       600
TTCTGGATCG ATAACAAGAA GTATTAGATT GACTATAACC GCATCGTGTC CGATGAATCT       660
ACAATATTTC CCCATGGATC GCCAGCTGTG CCACATTGAA ATCGAAAGCT TCGGTTACAC       720
GATGCGAGAT ATCCGATATT TCTGGAGAGA TGGACTGAGT AGTGTTGGCA TGAGCAGTGA       780
GGTCGAACTA CCGCAGTTCC GAGTTTTGGG ACACAGGCAG AGGGCGACCG AAATAAACCT       840
AACCACAGGC AACTATTCGC GTTTAGCCTG CGAAATTCAG TTCGTGCGTT CGATGGGCTA       900
CTACCTTATA CAAATCTACA TACCCTCTGG ACTGATCGTT GTTATATCAT GGGTATCATT       960
TTGGCTCAAT CGCAATGCAA CGCCGGCGCG TGTGTCGCTC GGTGTGACAA CCGTGTTGAC      1020
AATGACCACT TTGATGTCGT CAACAAATGC AGCGCTGCCA AGATTTCGT ACGTCAAATC       1080
GATTGACGTC TATCTGGGAA CATGCTTCGT TATGGTCTTT GCCAGTCTAC TGGAATACGC      1140
CACGGTCGGC TACATGGCAA AACGAATTCA AATGCGAAAA CAAAGATTTA TGGCGATCCA      1200
AAAGATAGCC GAACAGAAAA AGCAACAGCT CGACGGAGCG AACCAACAGC AGGCGAATCC      1260
CAATCCCAAT GCAAATGTGG GCGGACCCGG AGGAGTGGGC GTTGGACCCG GCGGACCCGG      1320
AGGACCCGGT GGCGGGGTCA ATGTGGGCGT CGGTATGGGC ATGGGACCGG AACATGGCCA      1380
CGGGCATGGA CACCACGCCC ACAGCCATGG ACATCCGCAT GCGCCCAAGC AAACAGTGAG      1440
TAACCGCCCA ATCGGCTTTT CCAATATCCA ACAAAACGTT GGTACGCGCG GTTGCTCGAT      1500
AGTGGGACCC TTGTTCCAGG AGGTGAGATT CAAGGTCCAC GACCCGAAGG CCCACTCCAA      1560
GGGCGGAACG CTGGAGAATA CGGTGAATGG CGGACGCGGT GGTCCGCAAT CGCATGGACC      1620
GGGTCCGGGC CAAGGCGGCG GACCGCCCGG CGGTGGCGGA GGCGGTGGAG GCGGGGGCGG      1680
ACCGCCCGAG GGCGGTGGCG ATCCGGAGGC AGCGGTTCCA GCCCATCTCC TACATCCGGG      1740
AAAAGTAAAA AAGGACATCA ACAAGCTGCT GGGCATCACG CCCTCCGACA TCGACAAGTA      1800
CTCACGCATC GTGTTCCCCG TGTGCTTTGT GTGCTTCAAC CTGATGTACT GGATCATTTA      1860
CCTGCATGTC AGCGACGTGG TCGCCGATGA TCTGGTGCTT CTGGGCGAGG AGTAGAGCGT      1920
CGTACTCAAG CGGCGCAAGT AGTCGAGGGC GTGGCCCAAG GACACAGGAG TGAACAGCGC      1980
GCGAGAGAGT CAAACTTGGC AGGGCACTGA AAAACCACAC AAAAAATAGA AAAAAAAAA       2040
AAACGAATGC TGCGGCCGCC GAATTC                                            2066
```

(2) INFORMATION FOR SEQ ID NO:4:

(i) SEQUENCE CHARACTERISTICS:
        (A) LENGTH: 637 amino acids
        (B) TYPE: amino acid
        (D) TOPOLOGY: unknown (ii) MOLECULE TYPE: peptide (xi) SEQUENCE DESCRIPTION: SEQ ID NO:4:

```
Ser Leu Leu Val Leu Phe Ala Glu Ala Gln Asn Lys Arg Ser Thr Leu
1               5                   10                  15

Gly Pro Ala Pro Pro Pro Pro Lys Thr His Ser Thr Thr Met
            20              25                  30

Ser Asp Ser Lys Met Asp Lys Leu Ala Arg Met Ala Pro Leu Pro Arg
        35                  40                  45

Thr Pro Leu Leu Thr Ile Trp Leu Ala Ile Asn Met Ala Leu Ile Ala
    50                  55                  60

Gln Glu Thr Gly His Lys Arg Ile His Thr Val Gln Ala Ala Thr Gly
65                  70                  75                  80

Gly Gly Ser Met Leu Gly Asp Val Asn Ile Ser Ala Ile Leu Asp Ser
                85                  90                  95

Phe Ser Val Ser Tyr Asp Lys Arg Val Arg Pro Asn Tyr Gly Gly Pro
                100                 105                 110

Pro Val Glu Val Gly Val Thr Met Tyr Val Leu Ser Ile Ser Ser Val
                115                 120                 125

Ser Glu Val Leu Met Asp Phe Thr Leu Asp Phe Tyr Phe Arg Gln Phe
130                 135                 140

Trp Thr Asp Pro Arg Leu Ala Tyr Arg Lys Arg Pro Gly Val Glu Thr
145                 150                 155                 160

Leu Ser Val Gly Ser Glu Phe Ile Lys Asn Ile Trp Val Pro Asp Thr
                165                 170                 175

Phe Phe Val Asn Glu Lys Gln Ser Tyr Phe His Ile Ala Thr Thr Ser
                180                 185                 190

Asn Glu Phe Ile Arg Val His His Ser Gly Ser Ile Thr Arg Ser Ile
                195                 200                 205

Arg Leu Thr Ile Thr Ala Ser Cys Pro Met Asn Leu Gln Tyr Phe Pro
                210                 215                 220

Met Asp Arg Gln Leu Cys His Ile Glu Ile Glu Ser Phe Gly Tyr Thr
225                 230                 235                 240

Met Arg Asp Ile Arg Tyr Phe Trp Arg Asp Gly Leu Ser Ser Val Gly
                245                 250                 255

Met Ser Ser Glu Val Glu Leu Pro Gln Phe Arg Val Leu Gly His Arg
                260                 265                 270

Gln Arg Ala Thr Glu Ile Asn Leu Thr Thr Gly Asn Tyr Ser Arg Leu
                275                 280                 285

Ala Cys Glu Ile Gln Phe Val Arg Ser Met Gly Tyr Tyr Leu Ile Gln
                290                 295                 300

Ile Tyr Ile Pro Ser Gly Leu Ile Val Val Ile Ser Trp Val Ser Phe
305                 310                 315                 320

Trp Leu Asn Arg Asn Ala Thr Pro Ala Arg Val Ser Leu Gly Val Thr
                325                 330                 335

Thr Val Leu Thr Met Thr Thr Leu Met Ser Ser Thr Asn Ala Ala Leu
                340                 345                 350

Pro Lys Ile Ser Tyr Val Lys Ser Ile Asp Val Tyr Leu Gly Thr Cys
                355                 360                 365

Phe Val Met Val Phe Ala Ser Leu Leu Glu Tyr Ala Thr Val Gly Tyr
                370                 375                 380

Met Ala Lys Arg Ile Gln Met Arg Lys Gln Arg Phe Met Ala Ile Gln
385                 390                 395                 400

Lys Ile Ala Glu Gln Lys Lys Gln Gln Leu Asp Gly Ala Asn Gln Gln
```

```
                    405                 410                 415
Gln Ala Asn Pro Asn Pro Asn Ala Asn Val Gly Gly Pro Gly Gly Val
            420                 425                 430

Gly Val Gly Pro Gly Gly Pro Gly Gly Pro Gly Gly Val Asn Val
        435                 440                 445

Gly Val Gly Met Gly Met Gly Pro Glu His His Gly His Gly His
        450                 455                 460

His Ala His Ser His Gly His Pro His Ala Pro Lys Gln Thr Val Ser
465                 470                 475                 480

Asn Arg Pro Ile Gly Phe Ser Asn Ile Gln Gln Asn Val Gly Thr Arg
                485                 490                 495

Gly Cys Ser Ile Val Gly Pro Leu Phe Gln Glu Val Arg Phe Lys Val
            500                 505                 510

His Asp Pro Lys Ala His Ser Lys Gly Gly Thr Leu Glu Asn Thr Val
        515                 520                 525

Asn Gly Gly Arg Gly Gly Pro Gln Ser His Gly Pro Gly Pro Gly Gln
530                 535                 540

Gly Gly Gly Pro Pro Gly Gly Gly Gly Gly Gly Gly Gly Gly Gly Gly
545                 550                 555                 560

Pro Pro Glu Gly Gly Asp Pro Glu Ala Ala Val Pro Ala His Leu
            565                 570                 575

Leu His Pro Gly Lys Val Lys Lys Asp Ile Asn Lys Leu Leu Gly Ile
            580                 585                 590

Thr Pro Ser Asp Ile Asp Lys Tyr Ser Arg Ile Val Phe Pro Val Cys
            595                 600                 605

Phe Val Cys Phe Asn Leu Met Tyr Trp Ile Ile Tyr Leu His Val Ser
            610                 615                 620

Asp Val Val Ala Asp Asp Leu Val Leu Leu Gly Glu Glu
625                 630                 635

(2) INFORMATION FOR SEQ ID NO:5:

(i) SEQUENCE CHARACTERISTICS:
        (A) LENGTH: 2066 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:5:

AAGCTTGCTT GTTCTTTTTG CAGAAGCTCA GAATAAACGC TCAACTTTGG GACCTGCACC      60

CCCCCCCCCC CCCCCCAAAA CACACAGCAC CACCATGAGT GATTCAAAAA TGGACAAGCT     120

GGCCCGGATG GCGCCCCTGC CCCGCACACC GCTGCTAACC ATCTGGCTGG CCATCAACAT     180

GGCCCTGATT GCACAGGAAA CGGGCCACAA ACGGATCCAT ACAGTGCAAG CGGCGACTGG     240

CGGTGGCAGC ATGCTGGGTG ACGTAAACAT ATCCGCTATT CTCGACTCCT TTAGTGTTAG     300

TTACGACAAA AGAGTAAGAC CCAATTACGG TGGTCCCCCT GTGGAGGTTG GCGTCACAAT     360

GTATGTCCTC AGTATCAGTT CGGTTTCGGA AGTTCTAATG GACTTCACAT GGATTTTTA      420

CTTTCGTCAA TTTTGGACCG ATCCTCGTTT AGCGTATAGA AAACGACCTG GTGTAGAAAC     480

ACTATCGGTT GGATCAGAGT TCATTAAGAA TATTTGGGTA CCTGACACCT TTTTTGTAAA     540

TGAAAAACAA TCATATTTTC ACATTGCAAC AACCAGTAAT GAATTCATAC GTGTGCATCA     600

TTCTGGATCG ATAACAAGAA GTATTAGATT GACTATAACC GCATCGTGTC CGATGAATCT     660

ACAATATTTC CCCATGGATC GCCAGCTGTG CCACATTGAA ATCGAAAGCT TCGGTTACAC     720
```

```
GATGCGAGAT ATCCGATATT TCTGGAGAGA TGGACTGAGT AGTGTTGGCA TGAGCAGTGA      780

GGTCGAACTA CCGCAGTTCC GAGTTTTGGG ACACAGGCAG AGGGCGACCG AAATAAACCT      840

AACCACAGGC AACTATTCGC GTTTAGCCTG CGAAATTCAG TTCGTGCGTT CGATGGGCTA      900

CTACCTTATA CAAATCTACA TACCCTCTGG ACTGATCGTT GTTATATCAT GGGTATCATT      960

TTGGCTCAAT CGCAATGCAA CGCCGGCGCG TGTGTCGCTC GGTGTGACAA CCGTGTTGAC     1020

AATGACCACT TTGATGTCGT CAACAAATGC AGCGCTGCCA AGATTTCGT ACGTCAAATC      1080

GATTGACGTC TATCTGGGAA CATGCTTCGT TATGGTCTTT GCCAGTCTAC TGGAATACGC     1140

CACGGTCGGC TACATGGCAA AACGAATTCA AATACGAAAA CAAAGATTTA TGGCGATCCA     1200

AAAGATAGCC GAACAGAAAA AGCAACAGCT CGACGGAGCG AACCAACAGC AGGCGAATCC     1260

CAATCCCAAT GCAAATGTGG GCGGACCCGG AGGAGTGGGC GTTGGACCCG GCGGACCCGG     1320

AGGACCCGGT GGCGGGGTCA ATGTGGGCGT CGGTATGGGC ATGGGACCGG AACATGGCCA     1380

CGGGCATGGA CACCACGCCC ACAGCCATGG ACATCCGCAT GCGCCCAAGC AAACAGTGAG     1440

TAACCGCCCA ATCGGCTTTT CCAATATCCA ACAAAACGTT GGTACGCGCG GTTGCTCGAT     1500

AGTGGGACCC TTGTTCCAGG AGGTGAGATT CAAGGTCCAC GACCCGAAGG CCCACTCCAA     1560

GGGCGGAACG CTGGAGAATA CGGTGAATGG CGGACGCGGT GGTCCGCAAT CGCATGGACC     1620

GGGTCCGGGC CAAGGCGGCG GACCGCCCGG CGGTGGCGGA GGCGGTGGAG GCGGGGGCGG     1680

ACCGCCCGAG GGCGGTGGCG ATCCGGAGGC AGCGGTTCCA GCCCATCTCC TACATCCGGG     1740

AAAAGTAAAA AAGGACATCA ACAAGCTGCT GGGCATCACG CCCTCCGACA TCGACAAGTA     1800

CTCACGCATC GTGTTCCCCG TGTGCTTTGT GTGCTTCAAC CTGATGTACT GGATCATTTA     1860

CCTGCATGTC AGCGACGTGG TCGCCGATGA TCTGGTGCTT CTGGGCGAGG AGTAGAGCGT     1920

CGTACTCAAG CGGCGCAAGT AGTCGAGGGC GTGGCCCAAG GACACAGGAG TGAACAGCGC     1980

GCGAGAGAGT CAAACTTGGC AGGGCACTGA AAAACCACAC AAAAAATAGA AAAAAAAAAA     2040

AAACGAATGC TGCGGCCGCC GAATTC                                          2066

(2) INFORMATION FOR SEQ ID NO:6:

(i) SEQUENCE CHARACTERISTICS:
        (A) LENGTH: 637 amino acids
        (B) TYPE: amino acid
        (D) TOPOLOGY: unknown (ii) MOLECULE TYPE: peptide (xi) SEQUENCE DESCRIPTION: SEQ ID NO:6:

Ser Leu Leu Val Leu Phe Ala Glu Ala Gln Asn Lys Arg Ser Thr Leu
1               5                   10                  15

Gly Pro Ala Pro Pro Pro Pro Pro Lys Thr His Ser Thr Thr Met
            20                  25                  30

Ser Asp Ser Lys Met Asp Lys Leu Ala Arg Met Ala Pro Leu Pro Arg
        35                  40                  45

Thr Pro Leu Leu Thr Ile Trp Leu Ala Ile Asn Met Ala Leu Ile Ala
    50                  55                  60

Gln Glu Thr Gly His Lys Arg Ile His Thr Val Gln Ala Ala Thr Gly
65                  70                  75                  80

Gly Gly Ser Met Leu Gly Asp Val Asn Ile Ser Ala Ile Leu Asp Ser
                85                  90                  95

Phe Ser Val Ser Tyr Asp Lys Arg Val Arg Pro Asn Tyr Gly Gly Pro
            100                 105                 110
```

-continued

```
Pro Val Glu Val Gly Val Thr Met Tyr Val Leu Ser Ile Ser Ser Val
            115                 120                 125

Ser Glu Val Leu Met Asp Phe Thr Leu Asp Phe Tyr Phe Arg Gln Phe
    130                 135                 140

Trp Thr Asp Pro Arg Leu Ala Tyr Arg Lys Arg Pro Gly Val Glu Thr
145                 150                 155                 160

Leu Ser Val Gly Ser Glu Phe Ile Lys Asn Ile Trp Val Pro Asp Thr
                165                 170                 175

Phe Phe Val Asn Glu Lys Gln Ser Tyr Phe His Ile Ala Thr Thr Ser
            180                 185                 190

Asn Glu Phe Ile Arg Val His His Ser Gly Ser Ile Thr Arg Ser Ile
        195                 200                 205

Arg Leu Thr Ile Thr Ala Ser Cys Pro Met Asn Leu Gln Tyr Phe Pro
    210                 215                 220

Met Asp Arg Gln Leu Cys His Ile Glu Ile Glu Ser Phe Gly Tyr Thr
225                 230                 235                 240

Met Arg Asp Ile Arg Tyr Phe Trp Arg Asp Gly Leu Ser Ser Val Gly
                245                 250                 255

Met Ser Ser Glu Val Glu Leu Pro Gln Phe Arg Val Leu Gly His Arg
            260                 265                 270

Gln Arg Ala Thr Glu Ile Asn Leu Thr Thr Gly Asn Tyr Ser Arg Leu
        275                 280                 285

Ala Cys Glu Ile Gln Phe Val Arg Ser Met Gly Tyr Tyr Leu Ile Gln
    290                 295                 300

Ile Tyr Ile Pro Ser Gly Leu Ile Val Val Ile Ser Trp Val Ser Phe
305                 310                 315                 320

Trp Leu Asn Arg Asn Ala Thr Pro Ala Arg Val Ser Leu Gly Val Thr
                325                 330                 335

Thr Val Leu Thr Met Thr Thr Leu Met Ser Ser Thr Asn Ala Ala Leu
            340                 345                 350

Pro Lys Ile Ser Tyr Val Lys Ser Ile Asp Val Tyr Leu Gly Thr Cys
        355                 360                 365

Phe Val Met Val Phe Ala Ser Leu Leu Glu Tyr Ala Thr Val Gly Tyr
    370                 375                 380

Met Ala Lys Arg Ile Gln Ile Arg Lys Gln Arg Phe Met Ala Ile Gln
385                 390                 395                 400

Lys Ile Ala Glu Gln Lys Lys Gln Gln Leu Asp Gly Ala Asn Gln Gln
                405                 410                 415

Gln Ala Asn Pro Asn Pro Asn Ala Asn Val Gly Gly Pro Gly Gly Val
            420                 425                 430

Gly Val Gly Pro Gly Gly Pro Gly Pro Gly Gly Val Asn Val
        435                 440                 445

Gly Val Gly Met Gly Met Gly Pro Glu His Gly His Gly His Gly His
    450                 455                 460

His Ala His Ser His Gly His Pro His Ala Pro Lys Gln Thr Val Ser
465                 470                 475                 480

Asn Arg Pro Ile Gly Phe Ser Asn Ile Gln Gln Asn Val Gly Thr Arg
                485                 490                 495

Gly Cys Ser Ile Val Gly Pro Leu Phe Gln Glu Val Arg Phe Lys Val
            500                 505                 510

His Asp Pro Lys Ala His Ser Lys Gly Gly Thr Leu Glu Asn Thr Val
        515                 520                 525

Asn Gly Gly Arg Gly Gly Pro Gln Ser His Gly Pro Gly Pro Gly Gln
    530                 535                 540
```

```
Gly Gly Gly Pro Pro Gly Gly Gly Gly Gly Gly Gly Gly
545             550             555             560

Pro Pro Glu Gly Gly Asp Pro Glu Ala Ala Val Pro Ala His Leu
            565             570             575

Leu His Pro Gly Lys Val Lys Lys Asp Ile Asn Lys Leu Gly Ile
            580             585             590

Thr Pro Ser Asp Ile Asp Lys Tyr Ser Arg Ile Val Phe Pro Val Cys
            595             600             605

Phe Val Cys Phe Asn Leu Met Tyr Trp Ile Ile Tyr Leu His Val Ser
            610             615             620

Asp Val Val Ala Asp Asp Leu Val Leu Leu Gly Glu Glu
625             630             635

(2) INFORMATION FOR SEQ ID NO:7:

(i) SEQUENCE CHARACTERISTICS:
        (A) LENGTH: 2066 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:7:

AAGCTTGCTT GTTCTTTTTG CAGAAGCTCA GAATAAACGC TCAACTTTGG GACCTGCACC      60

CCCCCCCCCC CCCCCCAAAA CACACAGCAC CACCATGAGT GATTCAAAAA TGGACAAGCT     120

GGCCCGGATG GCGCCCCTGC CCCGCACACC GCTGCTAACC ATCTGGCTGG CCATCAACAT     180

GGCCCTGATT GCACAGGAAA CGGGCCACAA ACGGATCCAT ACAGTGCAAG CGGCGACTGG     240

CGGTGGCAGC ATGCTGGGTG ACGTAAACAT ATCCGCTATT CTCGACTCCT TTAGTGTTAG     300

TTACGACAAA AGAGTAAGAC CCAATTACGG TGGTCCCCCT GTGGAGGTTG GCGTCACAAT     360

GTATGTCCTC AGTATCAGTT CGGTTTCGGA AGTTCTAATG GACTTCACAT TGGATTTTTA     420

CTTTCGTCAA TTTTGGACCG ATCCTCGTTT AGCGTATAGA AAACGACCTG GTGTAGAAAC     480

ACTATCGGTT GGATCAGAGT TCATTAAGAA TATTTGGGTA CCTGACACCT TTTTTGTAAA     540

TGAAAAACAA TCATATTTTC ACATTGCAAC AACCAGTAAT GAATTCATAC GTGTGCATCA     600

TTCTGGATCG ATAACAAGAA GTATTAGATT GACTATAACC GCATCGTGTC CGATGAATCT     660

ACAATATTTC CCCATGGATC GCCAGCTGTG CCACATTGAA ATCGAAAGCT TCGGTTACAC     720

GATGCGAGAT ATCCGATATT TCTGGAGAGA TGGACTGAGT AGTGTTGGCA TGAGCAGTGA     780

GGTCGAACTA CCGCAGTTCC GAGTTTTGGG ACACAGGCAG AGGGCGACCG AAATAAACCT     840

AACCACAGGC AACTATTCGC GTTTAGCCTG CGAAATTCAG TTCGTGCGTT CGATGGGCTA     900

CTACCTTATA CAAATCTACA TACCCTCTGG ACTGATCGTT GTTATATCAT GGGTATCATT     960

TTGGCTCAAT CGCAATGCAA CGCCGGCGCG TGTGGGGCTC GGTGTGACAA CCGTGTTGAC    1020

AATGACCACT TTGATGTCGT CAACAAATGC AGCGCTGCCA AAGATTTCGT ACGTCAAATC    1080

GATTGACGTC TATCTGGGAA CATGCTTCGT TATGGTCTTT GCCAGTCTAC TGGAATACGC    1140

CACGGTCGGC TACATGGCAA AACGAATTCA AATGCGAAAA CAAAGATTTA TGGCGATCCA    1200

AAAGATAGCC GAACAGAAAA AGCAACAGCT CGACGGAGCG AACCAACAGC AGGCGAATCC    1260

CAATCCCAAT GCAAATGTGG GCGGACCCGG AGGAGTGGGC GTTGGACCCG GCGGACCCGG    1320

AGGACCCGGT GGCGGGGTCA ATGTGGGCGT CGGTATGGGC ATGGGACCGG AACATGGCCA    1380

CGGGCATGGA CACCACGCCC ACAGCCATGG ACATCCGCAT GCGCCCAAGC AAACAGTGAG    1440
```

```
TAACCGCCCA ATCGGCTTTT CCAATATCCA ACAAAACGTT GGTACGCGCG GTTGCTCGAT    1500

AGTGGGACCC TTGTTCCAGG AGGTGAGATT CAAGGTCCAC GACCCGAAGG CCCACTCCAA    1560

GGGCGGAACG CTGGAGAATA CGGTGAATGG CGGACGCGGT GGTCCGCAAT CGCATGGACC    1620

GGGTCCGGGC AAGGCGGCG  GACCGCCCGG CGGTGGCGGA GGCGGTGGAG GCGGGGGCGG    1680

ACCGCCCGAG GGCGGTGGCG ATCCGGAGGC AGCGGTTCCA GCCCATCTCC TACATCCGGG    1740

AAAAGTAAAA AAGGACATCA ACAAGCTGCT GGGCATCACG CCCTCCGACA TCGACAAGTA    1800

CTCACGCATC GTGTTCCCCG TGTGCTTTGT GTGCTTCAAC CTGATGTACT GGATCATTTA    1860

CCTGCATGTC AGCGACGTGG TCGCCGATGA TCTGGTGCTT CTGGGCGAGG AGTAGAGCGT    1920

CGTACTCAAG CGGCGCAAGT AGTCGAGGGC GTGGCCCAAG GACACAGGAG TGAACAGCGC    1980

GCGAGAGAGT CAAACTTGGC AGGGCACTGA AAAACCACAC AAAAAATAGA AAAAAAAAA    2040

AAACGAATGC TGCGGCCGCC GAATTC                                          2066
```

(2) INFORMATION FOR SEQ ID NO:8:

(i) SEQUENCE CHARACTERISTICS:
        (A) LENGTH: 637 amino acids
        (B) TYPE: amino acid
        (D) TOPOLOGY: unknown (ii) MOLECULE TYPE: peptide (xi) SEQUENCE DESCRIPTION: SEQ ID NO:8:

```
Ser Leu Leu Val Leu Phe Ala Glu Ala Gln Asn Lys Arg Ser Thr Leu
 1               5                  10                  15

Gly Pro Ala Pro Pro Pro Pro Lys Thr His Ser Thr Thr Met
             20                  25                  30

Ser Asp Ser Lys Met Asp Lys Leu Ala Arg Met Ala Pro Leu Pro Arg
         35                  40                  45

Thr Pro Leu Leu Thr Ile Trp Leu Ala Ile Asn Met Ala Leu Ile Ala
     50                  55                  60

Gln Glu Thr Gly His Lys Arg Ile His Thr Val Gln Ala Ala Thr Gly
65                  70                  75                  80

Gly Gly Ser Met Leu Gly Asp Val Asn Ile Ser Ala Ile Leu Asp Ser
                 85                  90                  95

Phe Ser Val Ser Tyr Asp Lys Arg Val Arg Pro Asn Tyr Gly Gly Pro
            100                 105                 110

Pro Val Glu Val Gly Val Thr Met Tyr Val Leu Ser Ile Ser Ser Val
        115                 120                 125

Ser Glu Val Leu Met Asp Phe Thr Leu Asp Phe Tyr Phe Arg Gln Phe
    130                 135                 140

Trp Thr Asp Pro Arg Leu Ala Tyr Arg Lys Arg Pro Gly Val Glu Thr
145                 150                 155                 160

Leu Ser Val Gly Ser Glu Phe Ile Lys Asn Ile Trp Val Pro Asp Thr
                165                 170                 175

Phe Phe Val Asn Glu Lys Gln Ser Tyr Phe His Ile Ala Thr Thr Ser
            180                 185                 190

Asn Glu Phe Ile Arg Val His His Ser Gly Ser Ile Thr Arg Ser Ile
        195                 200                 205

Arg Leu Thr Ile Thr Ala Ser Cys Pro Met Asn Leu Gln Tyr Phe Pro
    210                 215                 220

Met Asp Arg Gln Leu Cys His Ile Glu Ile Glu Ser Phe Gly Tyr Thr
225                 230                 235                 240

Met Arg Asp Ile Arg Tyr Phe Trp Arg Asp Gly Leu Ser Ser Val Gly
```

```
                        245                 250                 255
Met Ser Ser Glu Val Glu Leu Pro Gln Phe Arg Val Leu Gly His Arg
                260                 265                 270

Gln Arg Ala Thr Glu Ile Asn Leu Thr Thr Gly Asn Tyr Ser Arg Leu
            275                 280                 285

Ala Cys Glu Ile Gln Phe Val Arg Ser Met Gly Tyr Tyr Leu Ile Gln
        290                 295                 300

Ile Tyr Ile Pro Ser Gly Leu Ile Val Val Ile Ser Trp Val Ser Phe
305                 310                 315                 320

Trp Leu Asn Arg Asn Ala Thr Pro Ala Arg Val Gly Leu Gly Val Thr
                325                 330                 335

Thr Val Leu Thr Met Thr Thr Leu Met Ser Ser Thr Asn Ala Ala Leu
                340                 345                 350

Pro Lys Ile Ser Tyr Val Lys Ser Ile Asp Val Tyr Leu Gly Thr Cys
            355                 360                 365

Phe Val Met Val Phe Ala Ser Leu Leu Glu Tyr Ala Thr Val Gly Tyr
        370                 375                 380

Met Ala Lys Arg Ile Gln Met Arg Lys Gln Arg Phe Met Ala Ile Gln
385                 390                 395                 400

Lys Ile Ala Glu Gln Lys Lys Gln Gln Leu Asp Gly Ala Asn Gln Gln
                405                 410                 415

Gln Ala Asn Pro Asn Pro Asn Ala Asn Val Gly Gly Pro Gly Gly Val
                420                 425                 430

Gly Val Gly Pro Gly Gly Pro Gly Pro Gly Gly Val Asn Val
            435                 440                 445

Gly Val Gly Met Gly Met Gly Pro Glu His Gly His Gly His Gly His
        450                 455                 460

His Ala His Ser His Gly His Pro His Ala Pro Lys Gln Thr Val Ser
465                 470                 475                 480

Asn Arg Pro Ile Gly Phe Ser Asn Ile Gln Gln Asn Val Gly Thr Arg
                485                 490                 495

Gly Cys Ser Ile Val Gly Pro Leu Phe Gln Glu Val Arg Phe Lys Val
            500                 505                 510

His Asp Pro Lys Ala His Ser Lys Gly Gly Thr Leu Glu Asn Thr Val
        515                 520                 525

Asn Gly Gly Arg Gly Gly Pro Gln Ser His Gly Pro Gly Pro Gly Gln
530                 535                 540

Gly Gly Gly Pro Pro Gly Gly Gly Gly Gly Gly Gly Gly Gly Gly Gly
                550                 555                 560

Pro Pro Glu Gly Gly Asp Pro Glu Ala Ala Val Pro Ala His Leu
            565                 570                 575

Leu His Pro Gly Lys Val Lys Lys Asp Ile Asn Lys Leu Leu Gly Ile
        580                 585                 590

Thr Pro Ser Asp Ile Asp Lys Tyr Ser Arg Ile Val Phe Pro Val Cys
            595                 600                 605

Phe Val Cys Phe Asn Leu Met Tyr Trp Ile Ile Tyr Leu His Val Ser
        610                 615                 620

Asp Val Val Ala Asp Asp Leu Val Leu Leu Gly Glu Glu
625                 630                 635
```

(2) INFORMATION FOR SEQ ID NO:9:

(i) SEQUENCE CHARACTERISTICS:
        (A) LENGTH: 1970 base pairs
        (B) TYPE: nucleic acid (C) STRANDEDNESS: single
(D) TOPOLOGY: unknown (ii) MOLECULE TYPE: cDNA (xi) SEQUENCE DESCRIPTION: SEQ ID NO:9:

| | | | | | |
|---|---|---|---|---|---|
| ATGAGTGATT | CAAAAATGGA | CAAGCTGGCC | CGGATGGCGC | CCCTGCCCCG | CACACGCGTG | 60 |
| CTAACCATCT | GGCTGGCCAT | CAACATGGCC | CTGATTGCAC | AGGAAACGGG | CCACAAACGG | 120 |
| ATCCATACAG | TGCAAGCGGC | GACTGGCGGT | GGCAGCATGC | TGGGTGACGT | AAACATATCC | 180 |
| GCTATTCTCG | ACTCCTTTAG | TGTTAGTTAC | GACAAAAGAG | TAAGACCCAA | TTACGGTGGT | 240 |
| CCCCCTGTGG | AGGTTGGCGT | CACAATGTAT | GTCCTCAGTA | TCAGTTCGGT | TTCGGAAGTT | 300 |
| CTAATGGACT | TCACATTGGA | TTTTTACTTT | CGTCAATTTT | GGACCGATCC | TCGTTTAGCG | 360 |
| TATAGAAAAC | GACCTGGTGT | AGAAACACTA | TCGGTTGGAT | CAGAGTTCAT | TAAGAATATT | 420 |
| TGGGTACCTG | ACACCTTTTT | TGTAAATGAA | ACAATCATA  | TTTTCACATT | GCAACAACCA | 480 |
| GTAATGAATT | CATACGTGTG | CATCATTCTG | GATCGATAAC | AAGAAGTATT | AGATTGACTA | 540 |
| TAACCGCATC | GTGTCCGATG | AATCTACAAT | ATTTCCCCAT | GGATCGCCAG | CTGTGCCACA | 600 |
| TTGAAATCGA | AAGCTTCGGT | TACACGATGC | GAGATATCCG | ATATTTCTGG | AGAGATGGAC | 660 |
| TGAGTAGTGT | TGGCATGAGC | AGTGAGGTCG | AACTACCGCA | GTTCCGAGTT | TTGGGACACA | 720 |
| GGCAGAGGGC | GACCGAAATA | AACCTAACCA | CAGGCAACTA | TTCGCGTTTA | GCCTGCGAAA | 780 |
| TTCAGTTCGT | GCGTTCGATG | GGCTACTACC | TTATACAAAT | CTACATACCC | TCTGGACTGA | 840 |
| TCGTTGTTAT | ATCATGGGTA | TCATTTTGGC | TCAATCGCAA | TGCAACGCCG | GCGCGTGTGG | 900 |
| CGCTCGGTGT | GACAACCGTG | TTGACAATGA | CCACTTTGAT | GTCGTCAACA | AATGCAGCGC | 960 |
| TGCCAAAGAT | TTCGTACGTC | AAATCGATTG | ACGTCTATCT | GGGAACATGC | TTCGTTATGG | 1020 |
| TCTTTGCCAG | TCTACTGGAA | TACGCCACGG | TCGGCTACAT | GGCAAACGA  | ATTCAAATGC | 1080 |
| GAAAACAAAG | ATTTATGGCG | ATCCAAAGAT | AGCCGAACAG | AAAAAGCAAC | AGCTCGACGG | 1140 |
| AGCGAACCAA | CAGCAGGCGA | ATCCCAATCC | CAATGCAAAT | GTGGGCGGAC | CCGGAGGAGT | 1200 |
| GGGCGTTGGA | CCCGGCGGAC | CCGGAGGACC | CGGTGGCGGG | GTCAATGTGG | GCGTCGGTAT | 1260 |
| GGGCATGGGA | CCGGAACATG | GCCACGGGCA | TGGACACCAC | GCCCACAGCC | ATGGACATCC | 1320 |
| GCATGCGCCC | AAGCAAACAG | TGAGTAACCG | CCCAATCGGC | TTTTCCAATA | TCCAACAAAA | 1380 |
| CGTTGGTACG | CGCGGTTGCT | CGATAGTGGG | ACCCTTGTTC | CAGGAGGTGA | GATTCAAGGT | 1440 |
| CCACGACCCG | AAGGCCCACT | CCAAGGGCGG | AACGCTGGAG | AATACGGTGA | ATGGCGGACG | 1500 |
| CGGTGGTCCG | CAATCGCATG | GACCGGGTCC | GGGCCAAGGC | GGCGGACCGC | CCGGCGGTGG | 1560 |
| CGGAGGCGGT | GGAGGCGGGG | GCGGACCGCC | CGAGGGCGGT | GGCGATCCGG | AGGCAGCGGT | 1620 |
| TCCAGCCCAT | CTCCTACATC | CGGGAAAAGT | AAAAAAGGAC | ATCAACAAGC | TGCTGGGCAT | 1680 |
| CACGCCCTCC | GACATCGACA | AGTACTCACG | CATCGTGTTC | CCCGTGTGCT | TTGTGTGCTT | 1740 |
| CAACCTGATG | TACTGGATCA | TTTACCTGCA | TGTCAGCGAC | GTGGTCGCCG | ATGATCTGGT | 1800 |
| GCTTCTGGGC | GAGGAGTAGA | GCGTCGTACT | CAAGCGGCGC | AAGTAGTCGA | GGGCGTGGCC | 1860 |
| CAAGGACACA | GGAGTGAACA | GCGCGCGAGA | GAGTCAAACT | TGCGAGGGCA | CTGAAAAACC | 1920 |
| ACACAAAAAA | TAGAAAAAAA | AAAAAACGA  | ATGCTGCGGC | CGCCGAATTC | | 1970 |

(2) INFORMATION FOR SEQ ID NO:10:

(i) SEQUENCE CHARACTERISTICS:
(A) LENGTH: 18 base pairs
(B) TYPE: nucleic acid
(C) STRANDEDNESS: single (D) TOPOLOGY: unknown (xi) SEQUENCE DESCRIPTION: SEQ ID NO:10:

GCAACTATTC GCGTTTAG                                                     18

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: single
        (D) TOPOLOGY: unknown (xi) SEQUENCE DESCRIPTION: SEQ ID NO:11:

CAGAAACGGT CAGATGACC                                                    19

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (xi) SEQUENCE DESCRIPTION: SEQ ID NO:12:

AACCGAGCTA GCTTACAGTT                                                   20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (xi) SEQUENCE DESCRIPTION: SEQ ID NO:13:

TGGTCCCATG CAGATCTTGC                                                   20

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: unknown (xi) SEQUENCE DESCRIPTION: SEQ ID NO:14:

ATACGCCACG GTCGGCTA                                                     18

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: unknown (xi) SEQUENCE DESCRIPTION: SEQ ID NO:15:

CGTTGGACCT TGAATCTC                                                     18

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: unknown -continued (xi) SEQUENCE DESCRIPTION: SEQ ID NO:16:

CATATCGTGG GTATCATT                                                        18

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: unknown (xi) SEQUENCE DESCRIPTION: SEQ ID NO:17:

CAGACTGGCA AATACCAT                                                        18

(2) INFORMATION FOR SEQ ID NO:18:

(i) SEQUENCE CHARACTERISTICS:
        (A) LENGTH: 17 base pairs
        (B) TYPE: nucleic acid
        (C) STRANDEDNESS: single
        (D) TOPOLOGY: unknown (xi) SEQUENCE DESCRIPTION: SEQ ID NO:18:

TGTGAAATAC AGTTCGT                                                         17

(2) INFORMATION FOR SEQ ID NO:19:

(i) SEQUENCE CHARACTERISTICS:
        (A) LENGTH: 17 base pairs
        (B) TYPE: nucleic acid
        (C) STRANDEDNESS: single
        (D) TOPOLOGY: unknown (xi) SEQUENCE DESCRIPTION: SEQ ID NO:19:

CAGGAGTGGT ACTGGTG                                                         17

(2) INFORMATION FOR SEQ ID NO:20:

(i) SEQUENCE CHARACTERISTICS:
        (A) LENGTH: 15 base pairs
        (B) TYPE: nucleic acid
        (C) STRANDEDNESS: single
        (D) TOPOLOGY: unknown (xi) SEQUENCE DESCRIPTION: SEQ ID NO:20:

TGGGTGAGGT TTTGG                                                           15